US009193721B2

(12) United States Patent
Combs et al.

(10) Patent No.: US 9,193,721 B2
(45) Date of Patent: Nov. 24, 2015

(54) FUSED DERIVATIVES AS PI3Kδ INHIBITORS

(75) Inventors: Andrew P. Combs, Kennett Square, PA (US); Richard B. Sparks, Wilmington, DE (US); Eddy W. Yue, Landenberg, PA (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 685 days.

(21) Appl. No.: 13/085,643

(22) Filed: Apr. 13, 2011

(65) Prior Publication Data
US 2011/0281884 A1  Nov. 17, 2011

Related U.S. Application Data

(60) Provisional application No. 61/324,143, filed on Apr. 14, 2010, provisional application No. 61/425,085, filed on Dec. 20, 2010.

(51) Int. Cl.
*C07D 471/04* (2006.01)
*A61K 31/52* (2006.01)
*C07D 473/34* (2006.01)
*C07D 473/26* (2006.01)

(52) U.S. Cl.
CPC ............ *C07D 471/04* (2013.01); *C07D 473/26* (2013.01)

(58) Field of Classification Search
CPC ........................... C07D 473/34; C07D 473/26
USPC .......................... 544/277; 514/263.21, 263.22
See application file for complete search history.

(56) References Cited

U.S. PATENT DOCUMENTS

| | | |
|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmermann |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 * | 2/2009 | Langkopf et al. .......... 514/263.2 |
| 7,528,143 B2 | 5/2009 | Noronha et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

Camps, Montserrat. Nat. Med. 2005, 11(9): 936-43.*

(Continued)

*Primary Examiner* — Golam M M Shameem
*Assistant Examiner* — Laura Daniel
(74) *Attorney, Agent, or Firm* — Fish & Richardson P.C.

(57) ABSTRACT

The present invention provides fused derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

39 Claims, No Drawings

(56) References Cited

U.S. PATENT DOCUMENTS

| | | |
|---|---|---|
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0312979 A1 | 12/2011 | Li et al. |
| 2012/0157430 A1 | 6/2012 | Li et al. |
| 2013/0029982 A1 | 1/2013 | Castro et al. |
| 2013/0059835 A1 | 3/2013 | Li et al. |
| 2013/0261101 A1 | 10/2013 | Combs et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121222 A1 | 5/2014 | Li et al. |
| 2014/0275127 A1 | 9/2014 | Combs et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011136925 | 7/2011 |
| RU | 2233842 | 8/2004 |
| SU | 1712359 | 2/1992 |
| WO | WO 93/16076 | 8/1993 |
| WO | WO 93/22291 | 11/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |

(56) References Cited

FOREIGN PATENT DOCUMENTS

| | | |
|---|---|---|
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/151930 | 10/2013 |

OTHER PUBLICATIONS

Barber, Domingo. Nat. Med. 2005, 11(9):933-5.*
Crabbe, Tom. TRENDS in Biochemical Sciences. 2007. 32(10): 450-56.*
MedicineNet, 2004.<http://www.medterms.com>.*
WebMD. Lung Disease & Respiratory Health Center: Lung Disease Overview, May 23, 2014 <http://www.webmd.com/lung/lung-diseases-overview>.*
WebMD. Lung Disease & Respiratory Health Center: ARDS, May 21, 2014. <http://www.webmd.com/lung/ards-acute-respiratory-distress-syndrome?page=2>.*
WebMD. Osteoarthritis Health Center: Osteoarthritis-prevention, Apr. 9, 2013. <http://www.webmd.com/osteoarthritis/tc/osteoarthritis-prevention>.*
WebMD. Psoriasis Health Center: Psoriasis-prevention, Jan. 9, 2012. <http://www.webmd.com/skin-problems-and-treatments/psoriasis/psoriasis-prevention>.*
WebMD. Bladder Cancer Health Center: Bladder Cancer-Prevention. Apr. 30, 2013 <http://www.webmd.com/cancer/bladder-cancer/bladder-cancer-prevention>.*
"Angiogenesis." Merriam-Webster.com. Merriam-Webster, n.d. Web. Jun. 16, 2014. <http://www.merriam-webster.com/dictionary/angiogenesis>.*
WebMD. Arthritis Health Center: What is Inflammation? Jul. 6, 2012 <http://www.webmd.com/arthritis/about-inflammation?page=2>.*
Martelli, Alberto. Expert Opin Investig Drugs (2009) 18(9) 1333-1349.*
"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.
Ali, et al., "Essential role for the p110δ phosphoinositide 3-kinase in the allergic response," Nature. 2004, 431(7011):1007-11.
Allen, et al., "Synthesis of C-6 substituted pyrazolo[1,5-a]pyridines with potent activity against herpesviruses," Bioorganic & Medicinal Chemistry (2006), 14(4), 944-954.
Bader, et al., "Cancer-specific mutations in PIK3CA are oncogenic in vivo," Proc Natl Acad Sci U S A. 2006, 103(5):1475-9.
Barber, et al., "PI3Kγ inhibition blocks glomerulonephritis and extends lifespan in a mouse model of systemic lupus," Nat Med. 2005, 11(9):933-5.
Barragan et al., "Protein Kinases in the Regulation of Apoptosis in B-cell Chronic Lymphocytic Leukemia," Leukemia and Lymphoma, 2003, 44(11):1865-1870.
Belema, et al., "Synthesis and structure-activity relationship of imidazo(1,2-a)thieno(3,2-e)pyrazines as IKK-β inhibitors," Bioorganic & Medicinal Chemistry Letters (2007), 17(15), 4284-4289.
Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.
Bennasar, et al., "Generation and Intermolecular Reactions of 2-Indolylacyl Radicals," Organic Letters (2001), 3(11), 1697-1700, CODEN: ORLEF7; ISSN: 1523-7060.
Berge et al., "Pharmaceutical Salts," J Pharma Sci, 1977, 66(1):1-19.
Bergman, et al., "Synthesis of indolocarbazole quinones; potent aryl hydrocarbon receptor ligands," Tetrahedron (2002), 58(7), 1443-1452.
Bhovi, et al., "1,3-dipolar cycloaddition reaction: Synthesis and antimicrobial activity of some new3-ethoxycarbonyl-5-methoxy-6-bromo-2-triazolylmethylindoles," Indian Journal of Heterocyclic Chemistry (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," Monatshefte fuer Chemie (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Boger, et al., "First and Second Generation Total Synthesis of the Teicoplanin Aglycon," JACS, 123(9), 1862-1871, 2001.
Bringmann, et al., "Novel concepts in directed biaryl synthesis. Part 65. Synthesis and structure of a novel twofold lactone-bridged ternaphthyl," Tetrahedron Letters (1998), 39(12), 1545-1548 CODEN: TELEAY; ISSN: 0040-4039.
Brock et al., "Roles of Gβδ in membrane recruitment and activation of p110δ/p101 phosphoinositide 3-kinaseγ," J Cell Biol., 2003, 160(1):89-99.
Brown, et al., "Small molecule inhibitors of IgE synthesis," Bioorganic & Medicinal Chemistry Letters (2006), 16(17), 4697-4699.

(56) References Cited

OTHER PUBLICATIONS

Camps, et al., "Blockade of PI3Kγ suppresses joint inflammation and damage in mouse models of rheumatoid arthritis," Nat Med. 2005, 11(9):936-43.
Cantley, "The Phosphoinositide 3-Kinase Pathway," Science, (2002) 296 (5573):1655-7.
Chai, et al., "Synthesis and in vitro anti-hepatitis B virus activities of some ethyl 6-bromo-5-hydroxy-1H-indole-3-carboxylates,"*Bioorganic & Medicinal Chemistry* (2006), 14(4), 911-917.
Clayton, et al., "A Crucial Role for the p110δ Subunit of Phosphatidylinositol 3-Kinase in B Cell Development and Activiation," J Exp Med. 2002, 196(6):753-63.
DeBerardinis et al., "The Biology of Cancer: Metabolic Reprogramming Fuels Cell Growth and Proliferation," Cell Metabolism, Jan. 2008, 7:11-20.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatography, Biomedical Applications*, (1981), 225(1), 73-81.
Fruman and Bismuth, "Fine Tuning the Immune Response with PI3K," *Immunological Revs.*, 2006, 228:253-272.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Greene and P. G. M. Wuts, Protective Groups in Organic Synthesis, 3rd Ed., Wiley & Sons, Inc., New York (1999).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.

Hickey, et al., "BCR-ABL Regulates Phosphatidylinositol 3-Kinase-p110γTranscription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota, "Efficient synthesis of 2,9-disubstituted 8-hydroxyadenine derivatives", Organic & Biomolecular Chemistry (2003), 1(8), 1354-1365.
Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of a fluorine-containing cytokinin, N6-pentafluoro-benzyladenosine," *Youji Huaxue* (1988), 8(2), 147-8 (with English abstract).
Ihle et al , "Inhibitors of phosphatidylinositol-3-kinase in cancer therapy", *Molecular Aspects of Medicine*, 31(2):135-144, 2010.
Irie, et al., "Discovery of selective and nonpeptidic cathepsin S inhibitors," *Bioorganic & Medicinal Chemistry Letters* (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie*, International Edition in English (1996), 35(16), 1815-1818.
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian Aplidiopsis sp.," *Tetrahedron Letters* (1997), 38(6), 941-944.
Kang, et al., "Phosphtidylinositol 3-kinase mutations identified in human cancer are oncogenic," Proc Natl Acad Sci U S A. 2005, 102(3):802-7.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," *Bioorganic & Medicinal Chemistry* (1997), 5(3), 507-514.
Kong and Yamori, "Advances in Development of Phosphatidylinositol 3-Kinase Inhibitors," Current Medicinal Chemistry, 16:2839-2854, 2009.

(56) References Cited

OTHER PUBLICATIONS

Kuduk et al., "Heterocyclic fused pyridone carboxylic acid M1 positive allosteric modulators," *Bioorganic & Medicinal Chemistry Letters* (2010), 20(8), 2533-2537.
Kung et al., "Characterization of a Murine Model of Allergic Pulmonary Inflammation," Int. Arch. Allergy Immunol., (abstract), 105(1):83-90, 1994.
Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.
Kutney, et al., "Dihydropyridines in synthesis and biosynthesis. IV. Dehydrosecodine, in vitro precursor of indole alkaloids," *Canadian Journal of Chemistry* (1982), 60(11), 1269-78.
Lee, et al., "Inhibition of phosphoinositide 3-kinase δ attenuates allergic airway inflammation and hyperresponsiveness in murine asthma model," FASEB J. 2006, 20(3):455-65.
Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).
Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).
Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.
Li, et al., "Optimization of the heterocyclic core of the quinazolinone-derived CXCR3 antagonists," *Bioorganic & Medicinal Chemistry Letters* (2008), 18(2), 688-693.
Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.
Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.
Lucas, et al., "Rauwolfia alkaloids. XXXI. The synthesis and activity of some reserpine analogs," *Journal of the American Chemical Society* (1959), 81, 1928-32.
Ma, et al., "Two new constituents from *Artemisia capillaris* Thunb", Molecules (2008), 13(2), 267-271.
Ma, et al., "Bromophenols Coupled with Nucleoside Bases and Brominated Tetrahydroisoquinolines from the Red Alga Rhodomela confervoides", Journal of Natural Products (2007), 70(3), 337-341.
Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.
Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.
McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.
McMahon, G., "VEGF Receptor Signaling in Tumor Angiogenesis," The Oncologist, 5(1):3-10, 2000.
Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.
Meijer et al., "Treatment of primary Sjögren syndrome with rituximab: extended follow-up, safety and efficacy of retreatment," Ann. Rheum. Dis., 68(2):284-285, 2009.
Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.
Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.
Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society*, Perkin Transactions 1 (2001), (18), 2213-2216.
Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.
Mishra et al., "Decanuclear Copper Framework Supported by a Tripodal Adenine Ligand," *Inorganic Chemistry* (Washington, DC, United States), (2010), 49(8), 3691-3693.
Mizoguchi, et al., "Genetic Alterations of Phosphoinositide 3-kinase Subunit Genes in Human Glioblastomas," Brain Pathol. 2004, 14(4):372-7.
Moffett, "Antiulcer agents. p-Aminobenzamido aromatic compounds", Journal of Medicinal Chemistry (1971), 14(10), 963-8.
Mohammadizadeh, et al., "A novel and expedient synthesis of 7-pyrimidinylpyrimido[4,5-d]pyrimidinones," *Helvetica Chimica Acta* (2010), 93(1), 153-157.
Morrison, et al., "Pyrimido[4,5-c]pyridazines. 1. Cyclizations with α-keto esters", *Journal of Organic Chemistry* (1978), 43(25), 4844-9.
Mukhopadhyay, et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.
Musmuca, et al., "Small-Molecule Interferon Inducers. Toward the Comprehension of the Molecular Determinants through Ligand-Based Approaches", Journal of Chemical Information and Modeling (2009),49(7), 1777-1786.
Najiwara, et al., Generation and behavior of naphthoyloxyl radicals in photocleavage of 1-(naphthoyloxy)-2-pyridones, *Chemistry Letters* (2001), (10), 1064-1065.
Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.
Nettekoven, M., "A combinatorial approach towards 2-acyl-3-amino-indole derivatives," *Tetrahedron Letters* (2000), 41(43), 8251-8254.
Norman, P., "Selective PI3Kδ inhibitors , a review of the patent literature", Expert Opinion on Therapeutic Patents, Informa Healthcare, 21(11):1773-1790, 2011.
Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., "Phosphoinositide 3-kinase δ inhibitor as a novel therapeutic agent in asthma," Respirology, 13:764-771, 2008.
Phillips, et al., "The reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [*Proceedings of the International Conference on the Chemistry of Boron*], 11th, Moscow, Russian Federation, Jul. 28-Aug. 1, 2002 (2003), Meeting Date 2002,

(56) References Cited

OTHER PUBLICATIONS 91-93. Editor(s): Bubnov, Yu. N. A. N. Nesmeyanov Institute of Organoelement Compounds, Russian Academy of Sciences: Moscow, Russia.

Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.

Ramos-Casals et al., "Rituximab in systemic lupus erythematosus; A systematic review of off-label use in 188 cases," Lupus, 18:767-776, 2009.

Randis, et al., "Role of PI3Kδ and PI3Kγ in inflammatory arthritis and tissue localization of neutrophils," Eur. J. Immunol., 2008, 38(5):1215-24.

Reich, et al., "Preparation of a,b-unsaturated carbonyl compounds and nitriles by selenoxide elimination ," *Organic Reactions* (Hoboken, NJ, United States) (1993), 44, No pp. given.

Remington's Pharmaceutical Sciences, 17th ed., Mack Publishing Company, Easton, Pa., 1985, p. 1418.

Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.

Roxas-Duncan, et al., "Identification and biochemical characterization of small-molecule inhibitors of *Clostridium botulinum* neurotoxin serotype A," *Antimicrobial Agents and Chemotherapy* (2009), 53(8), 3478-3486.

Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels, et al., "High Frequency of Mutations of the PIK3CA Gene in Human Cancers," Science, 2004, 304(5670):554.
Samuels and Ericson, "Oncogenic PI3K and its role in cancer," Curr Opin Oncol., 2006, 18(1):77-82.
Sasaki, et al., "Function of PI3Kγ in Thymocyte Development, T Cell Activation, and Neutrophil Migration," Science, 2000, 287(5455):1040-6.
Saxena, et al., "Pharmacophore-based virtual screening and docking studies on Hsp90 inhibitors", SAR and QSAR in Environmental Research (2010), 21(5-6), 445-462.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/1h2285/1h2285.pdf.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," *J Immunol.*, 2009, 183:6472-3480.
Xu et al., "Activation of the PI3K/AKT/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoshida, et al., "MexAB-OprM specific efflux pump inhibitors in *Pseudomonas aeruginosa*. Part 5: Carbon-substituted analogues at the C-2 position," *Bioorganic & Medicinal Chemistry* (2006), 14(6), 1993-2004.
Zhang et al., "Advances in preclinical small molecules for the treatment of NSCLC", Expert Opinion on Therapeutic Patents, 19(6):731-751, 2009.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Search Report dated Jul. 11, 2013 for International Appln. No. PCT/US2013/034803 (15 pgs.).

(56) References Cited

OTHER PUBLICATIONS

International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
Cannon, Burger's Medicinal Chemistry and Drug Discovery, Fifth Edition, vol. 1 Principles and Practice, Wiley-Interscience 1995, Ch. 19, pp. 783-803, 784.
Schafer and Kolkhof, "Failure is an option: learning from unsuccessful proof-of-concept trials," Drug Discovery Today, Nov. 2008, 13(21/22):913-916.
International Preliminary Report on Patentability for PCT/US2012/028915 dated Sep. 17, 2013 (6pgs.).
International Preliminary Report on Patentability for PCT/US2012/053398, issued Mar. 4, 2014 (6 pgs.).
"Arthritis: MedlinePlus Medical Encyclopedica," 2014, p. 1-5, accessed online Oct. 7, 2014; http://www.nlm.nih.gove/medlineplus/ency/article/001243.htm.
"Autoimmune disorders: MedlinePlus Medical Encyclopedia," 2013, p. 1-4, accessed online Oct. 7, 2014; http://www.nlm.nih.gov/medlineplus/ency/article/000816.htm.
Baek et al., "Complete remission induced by rituximab in refractory, seronegative, muscle-specific, kinase-positive myasthenia gravis," J Neurol Neurosurg Psychiatry, 2007, 78(7):771.
Ball, "PI3K inhibitors as potential therapeutics for autoimmune disease," Drug Discovery Today, 2014, pp. 1195-2119.
Collins et al., "Rituximab treatment of fibrillary glomerulonephritis," Am J Kidney Dis., 2008, 52(6):1158-62.
Devauchelle-Pensec, "Treatment of Primary Sjogren Syndrome with Rituximab," Annal Internal Med., 2014, 160:233-242.
Lipsky, "Systemic lupus erythematosus: an autoimmune disease of B cell hyperactivity," Nat Immunol., 2001, 2(9):764-6.
Liu et al, "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.
Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.
Segarra et al., "Successful treatment of membranous glomerulonephritis with rituximab in calcineurin inhibitor-dependent patients," Clin J Am Soc Nephrol., 2009, 4(6):1083-8.
Office Action in CO Application No. 11-179.464, received on Mar. 14, 2014, 17 pages.

Office Action in JP Application No. 2012-518563, dated Jul. 8, 2014, 6 pages (with English translation).
"A to Z List of Cancers," National Cancer Institute (http://www.cancer.gov/) (Downloaded May 29, 2014), 22 pages.
Bhatia and Rose, "Autoimmunity and autoimmune disease," Principles of Med Biol., 1996, 6:239-263, 244.
Brachmann et al., "PI3K and mTOR inhibitors—a new generation of targeted anticancer agents," Current Opinion Cell Biol., 2009, 21:194-198.
Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.
Coughlin et al., Approaches and limitations of phosphatidylinositol-3-kinase pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941.
Delmas and Meunier, "The Management of Paget's Disease of Bone," N Engl J Med., 1997, 336:558-566.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Cancer, 2009, 9:550-562.
Fine et al., "Neoplasms of the Central Nervous System," Cancer Principles Practice Oncol., 2005, 2:1834-1887.
Ghigo et al., "PI3K inhibition in inflammation: Toward tailored therapies for specific diseases," BioEssays, 2010, 32:185-196.
Harley, "Medical Management of Actue Renal Failure," Renal Failure Replacement Therapies, 2008, pp. 26-32.
Hayter and Cook, "Updated assessment of the prevalence, spectrum and case definition of autoimmune disease," Autoimmunity Reviews, 2012, 11:754-765.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.
Kim et al., "A signaling network in Phenylephrine-Induced Benign Prostatic Hyperplasia," Endocrinology, 2009, 150:3576-3583.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 9:1734-1740.
Kuster (ed), Kinase Inhibitors: Methods and Protocols Methods in Molecular Biology, 2012, 795:1-44.
Liu et al., "mTOR mediated anti-cancer drug discovery," Drug Discovery Today: Therapeutic Strategies, 2009, 6:47-55.
Luo et al., "Principles of Cancer Therapy: Oncogene and Non-oncogene Addiction," Cell, 2009, 36:823-837.
McDermott and Settleman, "Personalized Cancer Theraphy with Selective Kinase Inhibitors: An Emerging Paradigm in Medical Oncology," J Clinical Oncol., 2009, 27:5650-5659.
Anderson, 'medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&_suid=14297429843880910545130428968 4>. 10 pages.
Sawyers, "The cancer biomarker problem," Nature, 2008, 452:548-552.

(56) References Cited

OTHER PUBLICATIONS

Silverman, R. B., "The organic Chemistry of Drugs Design and Drug Action." Elselvier. Northwestern University. Second Edition. Evanstons Illinois. 2004. p. 29 and table 2.2 *too voluminous to cite*.

Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.

Yamada et al., "Alpha-1 Adrenoceptors in Human Prostate: Characterization and Alteration in Benign Prostatic Hypertrophy," J Pharmacol Experimental Therapeutics, 1987, 242(1):326-330.

Yoon et al., "Impact of fluoroquinolones on the diagnosis of pulmonary tuberculosis initially treated as bacterial pneumonia," Int'l J Tuberculosis and Lung Dis, 2005, 9:1215-1219.

Zhao and Vogt, "Class I PI3K in oncogenic cellular transformation," Oncogene, 2008, 27:5486-5496.

* cited by examiner

FUSED DERIVATIVES AS PI3Kδ INHIBITORS

This application claims the benefit of priority of U.S. Provisional Appl. Nos. 61/324,143, filed Apr. 14, 2010, and 61/425,085, filed Dec. 20, 2010, each of which is incorporated herein by reference in its entirety.

FIELD OF THE INVENTION

The present invention provides fused derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol. Chem., 2002, 277(44):41556-62) whereas PI3Kγ associates with two regulatory subunits (p101 and p84) and its activation is driven by the activation of G-protein-coupled receptors (Brock, et al., J. Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4): 194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat. Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat. Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3): 802-7; Bader, et al., Proc Natl. Acad Sci USA. 2006, 103(5): 1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3): 1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol. Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44): 5083-90; Mizoguchi, et al., Brain Pathol. 2004, 14(4):372-7; Knobbe, et al., Neuropathol Appl Neurobiol. 2005, 31(5): 486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and other ends.

SUMMARY

The present invention provides, inter alia, compounds of Formula I:

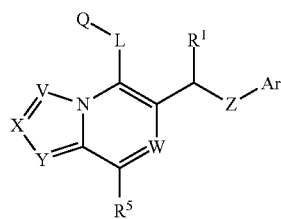

or a pharmaceutically acceptable salt thereof, wherein L, Q, V, X, Y, W, Z, Ar, $R^1$, and $R^5$ are defined herein.

The present invention further provides compounds of Formula Ia:

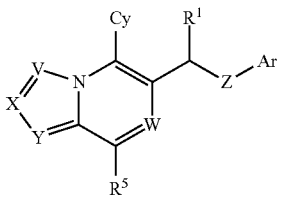

or a pharmaceutically acceptable salt thereof, wherein Cy, V, X, Y, W, Z, Ar, $R^1$, and $R^5$ are defined herein.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present invention further provides methods of treating an immune-based disease in a patient, comprising administering to said patient a therapeutically effective amount of a compound of the invention, or a pharmaceutically acceptable salt thereof.

The present invention also provides methods of treating a cancer in a patient, comprising administering to said patient a therapeutically effective amount of a compound of the invention, or a pharmaceutically acceptable salt thereof.

The present invention further provides methods of treating a lung disease in a patient, comprising administering to said patient a therapeutically effective amount of a compound of the invention, or a pharmaceutically acceptable salt thereof.

The present invention also provides a compound of invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

DETAILED DESCRIPTION

The present invention provides, inter alia, a compound of Formula I:

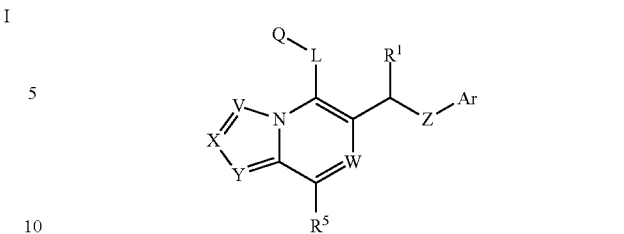

or a pharmaceutically acceptable salt thereof; wherein:
V is $CR^2$ or N;
X is $CR^3$ or N;
Y is $CR^4$ or N;
provided that at least two of V, X, and Y are other than N;
W is CH or N;
Z is a bond, O, S, or $NR^A$;
provided that when Z is a bond, then Ar is a bicyclic azaheteroaryl group, which is attached to Z at a nitrogen atom, wherein said bicyclic azaheteroaryl group is substituted with n independently selected $R^D$ groups;
L is a bond, $C_{1-4}$ alkylene, $NR^B$, O, or S;
Q is $C_{1-6}$ alkyl, $C_{2-6}$ alkenyl, $C_{2-6}$ alkynyl, or Cy; wherein said $C_{1-6}$ alkyl, $C_{2-6}$ alkenyl, and $C_{2-6}$ alkynyl are each optionally substituted by 1, 2, 3, 4, or 5 independently selected $R^C$ groups;
Cy is cycloalkyl, heterocycloalkyl, aryl or heteroaryl, each optionally substituted with 1, 2, 3, 4, or 5 independently selected $R^C$ groups;
each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, arylalkyl, heteroarylalkyl, cycloalkylalkyl, heterocycloalkylalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, heteroarylalkyl, cycloalkylalkyl, and heterocycloalkylalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$; $C(=NR^g)NR^{c2}R^{d2}$; $NR^{c2}C(=NR^g)NR^{c2}R^{d2}$; $NR^{c2}R^{d2}$, $NR^{c2}C(O)R^{b2}$, $NR^{c2}C(O)OR^{a2}$, $NR^{c2}C(O)NR^{c2}R^{d2}$; $NR^{c2}S(O)R^{b2}$; $NR^{c2}S(O)_2R^{b2}$; $NR^{c2}S(O)_2NR^{c2}R^{d2}$; $S(O)R^{b2}$; $S(O)NR^{c2}R^{d2}$, $S(O)_2R^{b2}$, and $S(O)_2NR^{c2}R^{d2}$;
$R^1$ is independently selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{1-6}$ haloalkyl, $C_{2-6}$ alkenyl, and $C_{2-6}$ alkynyl are each optionally substituted with 1, 2, 3 or 4 substituents independently selected from halo, OH, CN, $NR^{11}R^{12}$, $C_{1-6}$ alkoxy, $C_{1-6}$ haloalkoxy, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonyl amino;

each $R^{11}$ and $R^{12}$ is independently selected from H and $C_{1-6}$ alkyl;

or any $R^{11}$ and $R^{12}$ together with the N atom to which they are attached form a 3-, 4-, 5-, 6-, or 7-membered heterocycloalkyl group, which is optionally substituted with 1, 2, 3, or 4 substituents independently selected from $C_{1-6}$ alkyl;

$R^2$, $R^3$, $R^4$, or $R^5$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ar is heteroaryl, substituted with n independently selected $R^D$ groups;

each $R^D$ is independently selected from —($C_{1-4}$ alkyl)$_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^A$ is selected from H, $C_{1-6}$ alkyl, $C_{2-6}$ alkenyl, and $C_{2-6}$ alkynyl;

$R^B$ is selected from H, $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, 3 or 4 substituents independently selected from halo, OH, CN, $NR^{11}R^{12}$, $C_{1-6}$ alkoxy, $C_{1-6}$ haloalkoxy, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $Cy^1$ is, independently, aryl, heteroaryl, cycloalkyl, or heterocycloalkyl, each optionally substituted by 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$, $R^c$, and $R^d$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^b$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^e$, $R^f$, and $R^g$ is independently selected from H, $C_{1-6}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a1}$, $R^{c1}$, and $R^{d1}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{b1}$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)

aminosulfonylamino, aminocarbonylamino, $C_{1-6}$ alkylaminocarbonylamino, and di($C_{1-6}$ alkyl)aminocarbonylamino;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{a2}$, $R^{c2}$, and $R^{d2}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{b2}$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, thio, $C_{1-6}$ alkylthio, $C_{1-6}$ alkylamino, di($C_{1-6}$ alkyl)amino, $C_{1-6}$ haloalkyl, $C_{1-6}$ haloalkoxy, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{b5}$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, thio, $C_{1-6}$ alkylthio, $C_{1-6}$ alkylamino, di($C_{1-6}$ alkyl) amino, $C_{1-6}$ haloalkyl, $C_{1-6}$ haloalkoxy, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl) aminocarbonylamino;

or any $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

n is 0, 1, 2, 3, 4, or 5; and r is 0 or 1.

In some embodiments, the compound is a compound of Formula Ia:

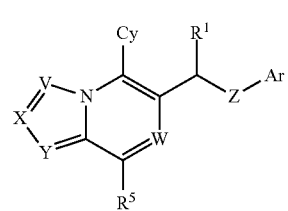

Ia or a pharmaceutically acceptable salt thereof; wherein:

V is $CR^2$ or N;

X is $CR^3$ or N;

Y is $CR^4$ or N;

provided that at least two of V, X, and Y are other than N;

W is CH or N;

Z is O, S, or $NR^A$;

Cy is cycloalkyl, heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, arylalkyl, heteroarylalkyl, cycloalkylalkyl, heterocycloalkylalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^c)R^b$, $C(=NR^c)NR^cR^d$, $NR^cC(=NR^c)NR^cR^d$, $NR^cS(O)R^b$, $NR^cS(O)_2R^b$, $NR^cS(O)_2NR^cR^d$, S(O)

$R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, heteroarylalkyl, cycloalkylalkyl, and heterocycloalkylalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^g)NR^{c2}R^{d2}$, $NR^{c2}C(=NR^g)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^1$ is independently selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{1-6}$ haloalkyl, $C_{2-6}$ alkenyl, and $C_{2-6}$ alkynyl are each optionally substituted with 1, 2, 3 or 4 substituents independently selected from halo, OH, CN, $NR^{11}R^{12}$, $C_{1-6}$ alkoxy, $C_{1-6}$ haloalkoxy, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{11}$ and $R^{12}$ is independently selected from H and $C_{1-6}$ alkyl;

or any $R^{11}$ and $R^{12}$ together with the N atom to which they are attached form a 3-, 4-, 5-, 6-, or 7-membered heterocycloalkyl group, which is optionally substituted with 1, 2, 3, or 4 substituents independently selected from $C_{1-6}$ alkyl;

$R^2$, $R^3$, $R^4$, or $R^5$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ar is heteroaryl, substituted with n independently selected $R^D$ groups;

each $R^D$ is independently selected from $—(C_{1-4}\text{ alkyl})_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^A$ is selected from H, $C_{1-6}$ alkyl, $C_{2-6}$ alkenyl, and $C_{2-6}$ alkynyl;

each $Cy^1$ is, independently, aryl, heteroaryl, cycloalkyl, or heterocycloalkyl, each optionally substituted by 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$, $R^c$, and $R^d$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^b$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^e$, $R^f$, and $R^g$ is independently selected from H, $C_{1-6}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a1}$, $R^{c1}$, and $R^{d1}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{b1}$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{a2}$, $R^{c2}$, and $R^{d2}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{f})NR^{c5}R^{d5}$, $NR^{c5}C(=NR^{f})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{b2}$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{f})NR^{c5}R^{d5}$, $NR^{c5}C(=NR^{f})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{f})NR^{c5}R^{d5}$, $NR^{c5}C(=NR^{f})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, thio, $C_{1-6}$ alkylthio, $C_{1-6}$ alkylamino, di($C_{1-6}$ alkyl)amino, $C_{1-6}$ haloalkyl, $C_{1-6}$ haloalkoxy, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{b5}$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, thio, $C_{1-6}$ alkylthio, $C_{1-6}$ alkylamino, di($C_{1-6}$ alkyl) amino, $C_{1-6}$ haloalkyl, $C_{1-6}$ haloalkoxy, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl) aminocarbonylamino;

or any $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

n is 0, 1, 2, 3, 4, or 5; and r is 0 or 1.

In some embodiments, Z is $NR^A$.

In some embodiments, Cy is aryl, optionally substituted with 1, 2, 3, 4, or 5 independently selected $R^C$ groups.

In some embodiments, Cy is heterocycloalkyl, optionally substituted with 1, 2, 3, 4, or 5 independently selected $R^C$ groups.

In some embodiments, Cy is heteroaryl, optionally substituted with 1, 2, 3, 4, or 5 independently selected $R^C$ groups.

In some embodiments, Cy is a phenyl ring, which is optionally substituted with 1, 2, 3, 4, or 5 independently selected $R^C$ groups.

In some embodiments, Cy is a phenyl ring, 5-membered heterocycloalkyl ring or a 6-membered heterocycloalkyl ring, each of which is optionally substituted with 1, 2, 3, 4, or 5 independently selected $R^C$ groups.

In some embodiments, each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and S(O)₂NR^cR^d; wherein said C₁₋₆ alkyl is optionally substituted with 1, 2, 3, 4, or 5 substituents independently selected from hydroxy, C₁₋₆ alkoxy, and C₁₋₆ haloalkoxy.

In some embodiments, each R^C is independently halo.

In some embodiments, Ar is a bicyclic azaheteroaryl group, substituted with n independently selected R^D groups; wherein n is 0, 1, 2, 3, 4, or 5.

In some embodiments, Ar is a purine ring, substituted with n independently selected R^D groups; wherein n is 0, 1, or 2.

In some embodiments, Ar is a moiety of formula:

wherein n is 0 or 1.

In some embodiments, n is 0.

In some embodiments, n is 0 or 1.

In some embodiments, n is 0, 1, or 2.

In some embodiments, each R^D is independently NR^c1R^d1.

In some embodiments, each R^D is independently selected from amino, C₁₋₆ alkylamino, and di(C₁₋₆ alkyl)amino.

In some embodiments, R¹ is C₁₋₆ alkyl.

In some embodiments, R¹ is methyl.

In some embodiments, R^A is H.

In some embodiments, L is NR^B; Q is C₁₋₆ alkyl; and R^A and R^B are each C₁₋₆ alkyl.

In some embodiments:

each R^a, R^c, and R^d is independently selected from H and C₁₋₆ alkyl, wherein said C₁₋₆ alkyl is optionally substituted with 1, 2, 3, 4, or 5 substituents independently selected from C₁₋₆ alkyl, C₁₋₆ haloalkyl, halo, CN, OR^a5, SR^a5, C(O)R^b5, C(O)NR^c5R^d5, C(O)OR^a5, OC(O)R^b5, OC(O)NR^c5R^d5, NR^c5R^d5, NR^c5C(O)R^b5, NR^c5C(O)NR^c5R^d5, NR^c5C(O)OR^a5, C(=NR^f)NR^c5R^d5, NR^c5C(=NR^f)NR^c5R^d5, S(O)R^b5, S(O)NR^c5R^d5, S(O)₂R^b5, NR^c5S(O)₂R^b5, NR^c5S(O)₂NR^c5R^d5, and S(O)₂NR^c5R^d5; and each R^b is, independently, C₁₋₆ alkyl, wherein said C₁₋₆ alkyl is optionally substituted with 1, 2, 3, 4, or 5 substituents independently selected from C₁₋₆ alkyl, C₁₋₆ haloalkyl, halo, CN, OR^a5, SR^a5, C(O)R^b5, C(O)NR^c5R^d5, C(O)OR^a5, OC(O)R^b5, OC(O)NR^c5R^d5, NR^c5R^d5, NR^c5C(O)R^b5, NR^c5C(O)NR^c5R^d5, NR^c5C(O)OR^a5, C(=NR^f)NR^c5R^d5, NR^c5C(=NR^f)NR^c5R^d5, S(O)R^b5, S(O)NR^c5R^d5, S(O)₂R^b5, NR^c5S(O)₂R^b5, NR^c5S(O)₂NR^c5R^d5, and S(O)₂NR^c5R^d5.

In some embodiments:

each R^a2, R^c2, and R^d2 is independently selected from H and C₁₋₆ alkyl, wherein said C₁₋₆ alkyl is optionally substituted with 1, 2, 3, 4, or 5 substituents independently selected from C₁₋₆ alkyl, C₁₋₆ haloalkyl, halo, CN, OR^a5, SR^a5, C(O)R^b5, C(O)NR^c5R^d5, C(O)OR^a5, OC(O)R^b5, OC(O)NR^c5R^d5, NR^c5R^d5, NR^c5C(O)R^b5, NR^c5C(O)NR^c5R^d5, NR^c5C(O)OR^a5, C(=NR^f)NR^c5R^d5, NR^c5C(=NR^f)NR^c5R^d5, S(O)R^b5, S(O)NR^c5R^d5, S(O)₂R^b5, NR^c5S(O)₂R^b5, NR^c5S(O)₂NR^c5R^d5, and S(O)₂NR^c5R^d5; and each R^b2 is, independently, C₁₋₆ alkyl, wherein said C₁₋₆ alkyl is optionally substituted with 1, 2, 3, 4, or 5 substituents independently selected from C₁₋₆ alkyl, C₁₋₆ haloalkyl, halo, CN, OR^a5, SR^a5, C(O)R^b5, C(O)NR^c5R^d5, C(O)OR^a5, OC(O)R^b5, OC(O)NR^c5R^d5, NR^c5R^d5, NR^c5C(O)R^b5, NR^c5C(O)NR^c5R^d5, NR^c5C(O)OR^a5, C(=NR^f)NR^c5R^d5, NR^c5C(=NR^f)NR^c5R^d5, S(O)R^b5, S(O)NR^c5R^d5, S(O)₂R^b5, NR^c5S(O)₂R^b5, NR^c5S(O)₂NR^c5R^d5, and S(O)₂NR^c5R^d5.

In some embodiments:

each R^a1, R^c1, and R^d1 is independently selected from H and C₁₋₆ alkyl, wherein said C₁₋₆ alkyl is optionally substituted with 1, 2, 3, 4, or 5 substituents independently selected from OH, CN, halo, C₁₋₆ alkyl, C₂₋₆ alkenyl, C₂₋₆ alkynyl, C₁₋₆ haloalkyl, C₁₋₆ alkoxy, C₁₋₆ haloalkoxy, amino, C₁₋₆ alkylamino, di(C₁₋₆ alkyl)amino, thio, C₁₋₆ alkylthio, C₁₋₆ alkylsulfinyl, C₁₋₆ alkylsulfonyl, carbamyl, C₁₋₆ alkylcarbamyl, di(C₁₋₆ alkyl)carbamyl, carboxy, C₁₋₆ alkylcarbonyl, C₁₋₆ alkoxycarbonyl, C₁₋₆ alkylcarbonylamino, C₁₋₆ alkylsulfonylamino, aminosulfonyl, C₁₋₆ alkylaminosulfonyl, di(C₁₋₆ alkyl)aminosulfonyl, aminosulfonylamino, C₁₋₆ alkylaminosulfonylamino, di(C₁₋₆ alkyl)aminosulfonylamino, aminocarbonylamino, C₁₋₆ alkylaminocarbonylamino, and di(C₁₋₆ alkyl)aminocarbonylamino; and each R^b1 is, independently, C₁₋₆ alkyl, wherein said C₁₋₆ alkyl is optionally substituted with 1, 2, 3, 4, or 5 substituents independently selected from OH, NO₂, CN, halo, C₁₋₆ alkyl, C₂₋₆ alkenyl, C₂₋₆ alkynyl, C₁₋₆ haloalkyl, C₁₋₆ alkoxy, C₁₋₆ haloalkoxy, amino, C₁₋₆ alkylamino, di(C₁₋₆ alkyl)amino, thio, C₁₋₆ alkylthio, C₁₋₆ alkylsulfinyl, C₁₋₆ alkylsulfonyl, carbamyl, C₁₋₆ alkylcarbamyl, di(C₁₋₆ alkyl)carbamyl, carboxy, C₁₋₆ alkylcarbonyl, C₁₋₆ alkoxycarbonyl, C₁₋₆ alkylcarbonylamino, C₁₋₆ alkylsulfonylamino, aminosulfonyl, C₁₋₆ alkylaminosulfonyl, di(C₁₋₆ alkyl)aminosulfonyl, aminosulfonylamino, C₁₋₆ alkylaminosulfonylamino, di(C₁₋₆ alkyl)aminosulfonylamino, aminocarbonylamino, C₁₋₆ alkylaminocarbonylamino, and di(C₁₋₆ alkyl)aminocarbonylamino.

In some embodiments:

each R^a5, R^c5, and R^d5 is independently selected from H and C₁₋₆ alkyl, wherein said C₁₋₆ alkyl is optionally substituted with 1, 2, or 3 substituents independently selected from OH, CN, amino, halo, C₁₋₆ alkyl, C₁₋₆ alkoxy, C₁₋₆ alkylthio, C₁₋₆ alkylamino, di(C₁₋₆ alkyl)amino, C₁₋₆ haloalkyl, and C₁₋₆ haloalkoxy; and each R^b5 is, independently, C₁₋₆ alkyl, wherein said C₁₋₆ alkyl is optionally substituted with 1, 2, or 3 substituents independently selected from OH, CN, amino, halo, C₁₋₆ alkyl, C₁₋₆ alkoxy, C₁₋₆ alkylthio, C₁₋₆ alkylamino, di(C₁₋₆ alkyl)amino, C₁₋₆ haloalkyl, and C₁₋₆ haloalkoxy.

In some embodiments, each R^a, R^c, and R^d is independently selected from H, C₁₋₆ alkyl, aryl, cycloalkyl, heteroaryl, and heterocycloalkyl; wherein said C₁₋₆ alkyl, aryl, cycloalkyl, heteroaryl, heterocycloalkyl are each optionally substituted with 1, 2, 3, 4, or 5 substituents independently selected from C₁₋₆ alkyl, C₁₋₆ haloalkyl, halo, CN, and OR^a5;

each R^b is independently selected from C₁₋₆ alkyl, aryl, cycloalkyl, heteroaryl, and heterocycloalkyl; each of which is optionally substituted with 1, 2, 3, 4, or 5 substituents independently selected from C₁₋₆ alkyl, C₁₋₆ haloalkyl, halo, CN, and OR^a5; and each OR^a5 is independently selected from H and C₁₋₄ alkyl.

In some embodiments, R², R³, R⁴, and R⁵ are independently selected from H, OH, C₁₋₆ alkoxy, C₁₋₆ haloalkoxy, CN, halo, C₁₋₆ alkyl, and C₁₋₆ haloalkyl.

In some embodiments, R⁵ is halo.

In some embodiments, R² is selected from H and C₁₋₆ alkyl.

In some embodiments, R³ and R⁴ are each H.

In some embodiments, V is CR².

In some embodiments, V is N.

In some embodiments, X is N.

In some embodiments, X is CR³.

In some embodiments, Y is N.

In some embodiments, Y is CR⁴.

In some embodiments, W is N.

In some embodiments, W is CH.

In some embodiments, —V=X—Y= is —N=C($R^3$)—C($R^4$)=, —C($R^2$)=N—C($R^4$)=, —C($R^2$)=C($R^3$)—N=, or —C($R^2$)=C($R^3$)—C($R^4$)=. In some embodiments, —V=X—Y= is —N=C($R^3$)—C($R^4$)=, —C($R^2$)=N—C($R^4$)=, or —C($R^2$)=C($R^3$)—N=.

In some embodiments, L is a bond.

In some embodiments -L-Q is -Cy.

In some embodiments, -L-Q is -Q, —O-Q or —$NR^B$-Q, wherein $R^B$ is $C_{1-6}$ alkyl.

In some embodiments, -L-Q is —O-Q.

In some embodiments, -L-Q is —$NR^B$-Q, wherein $R^B$ is $C_{1-6}$ alkyl.

In some embodiments:

Z is NH;

Cy is cycloalkyl, heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $C(=NR^e)R^b$, $C(=NR^g)NR^cR^d$, $NR^cC(=NR^e)$ $NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-6}$ haloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^g)NR^{c2}R^{d2}$, $NR^{c2}C(=NR^g)$ $NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

Ar is a bicyclic azaheteroaryl group, substituted with n independently selected $R^D$ groups; wherein n is 0, 1, 2, 3, or 4;

each $R^D$ is independently selected from $NR^{c1}R^{d1}$;

$R^1$ is $C_{1-6}$ alkyl; and $R^2$, $R^3$, $R^4$, and $R^5$ are independently selected from H, OH, halo, CN, $C_{1-6}$ alkyl, $C_{1-6}$ alkoxy, $C_{1-6}$ haloalkoxy, amino, $C_{1-6}$ alkylamino, di($C_{1-6}$-alkyl)amino, carboxy, $C_{1-6}$ alkylcarbonyl, $C_{1-6}$ alkoxycarbonyl, carbamyl, $C_{1-6}$ alkylcarbamyl, di($C_{1-6}$-alkyl)carbamyl, $C_{1-6}$ alkylcarbonylamino, $C_{1-6}$ alkylthio, $C_{1-6}$ alkylsulfinyl, and $C_{1-6}$ alkylsulfonyl.

In some embodiments:

Z is NH;

Cy is aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein said $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a bicyclic azaheteroaryl group, substituted with n independently selected $R^D$ groups; wherein n is 0 or 1;

each $R^D$ is independently selected from $NR^{c1}R^{d1}$;

$R^1$ is $C_{1-6}$ alkyl; and $R^2$, $R^3$, $R^4$, and $R^5$ are each independently selected from H, OH, $C_{1-6}$ alkoxy, $C_{1-6}$ haloalkoxy, halo, CN, $C_{1-6}$ alkyl, and $C_{1-6}$ haloalkyl.

In some embodiments:

Z is NH;

Cy is aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein said $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a purine ring;

$R^1$ is $C_{1-6}$ alkyl; and $R^2$, $R^3$, $R^4$, and $R^5$ are each independently selected from H, OH, $C_{1-6}$ alkoxy, $C_{1-6}$ haloalkoxy, halo, CN, $C_{1-6}$ alkyl, and $C_{1-6}$ haloalkyl.

In some embodiments:

Z is NH;

Cy is aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein said $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a moiety of formula:

$R^1$ is $C_{1-6}$ alkyl; and $R^2$, $R^3$, $R^4$, and $R^5$ are each independently selected from H, OH, $C_{1-6}$ alkoxy, $C_{1-6}$ haloalkoxy, halo, CN, $C_{1-6}$ alkyl, and $C_{1-6}$ haloalkyl.

In some embodiments:

Z is NH;

Cy is aryl, optionally substituted with 1, 2, 3, 4, or 5 independently selected $R^C$ groups;

each $R^C$ is independently selected from halo;

Ar is a moiety of formula:

$R^1$ is $C_{1-6}$ alkyl; and $R^2$, $R^3$, $R^4$, and $R^5$ are each independently selected from H, halo, CN, $C_{1-6}$ alkyl, and $C_{1-6}$ haloalkyl.

In some embodiments:

Z is NH;

Cy is aryl, heteroaryl, or heterocycloalkyl, optionally substituted with 1, 2, 3, 4, or 5 independently selected $R^C$ groups;

each $R^C$ is independently selected from halo, $C_{1-6}$ alkyl, $C_{1-6}$ haloalkyl, aryl, cycloalkyl, heteroaryl, heterocycloalkyl, arylalkyl, heteroarylalkyl, cycloalkylalkyl, heterocycloalkylalkyl, CN, $OR^a$, $C(O)R^b$, $C(O)NR^cR^d$, $C(O)OR^a$, $NR^cR^d$, $S(O)_2R^b$, and $S(O)_2NR^cR^d$; wherein said $C_{1-6}$ alkyl, aryl, cycloalkyl, heteroaryl, heterocycloalkyl, arylalkyl, heteroarylalkyl, cycloalkylalkyl, and heterocycloalkylalkyl are each optionally substituted with 1, 2, 3, 4, or 5 substituents independently selected from halo, $C_{1-6}$ alkyl, $C_{1-6}$ haloalkyl, CN, and $OR^{a2}$;

each $R^a$, $R^c$, and $R^d$ is independently selected from H, $C_{1-6}$ alkyl, aryl, cycloalkyl, heteroaryl, and heterocycloalkyl; wherein said $C_{1-6}$ alkyl, aryl, cycloalkyl, heteroaryl, heterocycloalkyl are each optionally substituted with 1, 2, 3, 4, or 5 substituents independently selected from $C_{1-6}$ alkyl, $C_{1-6}$ haloalkyl, halo, CN, and $OR^{a5}$;

each $R^b$ is independently selected from $C_{1-6}$ alkyl, aryl, cycloalkyl, heteroaryl, and heterocycloalkyl; each of which is optionally substituted with 1, 2, 3, 4, or 5 substituents independently selected from $C_{1-6}$ alkyl, $C_{1-6}$ haloalkyl, halo, CN, and $OR^{a5}$;

each $OR^{a2}$ and $OR^{a5}$ is independently selected from H and $C_{1-4}$ alkyl;

Ar is a moiety of formula:

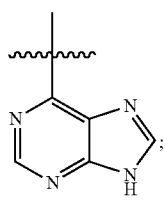 [SMILES: *c1ncnc2[nH]cnc12]

$R^1$ is $C_{1-6}$ alkyl; and $R^2$, $R^3$, $R^4$, and $R^5$ are each independently selected from H, halo, CN, $C_{1-6}$ alkyl, and $C_{1-6}$ haloalkyl.

In some embodiments:

Z is NH;

Cy is phenyl, 5-membered or 6-membered heterocycloalkyl, each optionally substituted with 1, 2, 3, 4, or 5 independently selected $R^C$ groups;

each $R^C$ is independently selected from halo, $C_{1-6}$ alkyl, $C_{1-6}$ haloalkyl, cycloalkyl, heterocycloalkyl, cycloalkylalkyl, heterocycloalkylalkyl, CN, $OR^a$, $C(O)R^b$, and $S(O)_2R^b$; wherein said $C_{1-6}$ alkyl, $C_{1-6}$ haloalkyl, cycloalkyl, heterocycloalkyl, cycloalkylalkyl, heterocycloalkylalkyl are each optionally substituted with 1, 2, or 3 substituents independently selected from halo, $C_{1-6}$ alkyl, CN, and $OR^{a2}$;

each $R^a$ is selected from H, $C_{1-6}$ alkyl, aryl, cycloalkyl, heteroaryl, and heterocycloalkyl; wherein said $C_{1-6}$ alkyl, aryl, cycloalkyl, heteroaryl, heterocycloalkyl are each optionally substituted with 1, 2, 3, 4, or 5 substituents independently selected from $C_{1-6}$ alkyl, $C_{1-6}$ haloalkyl, halo, CN, and $OR^{a5}$;

each $R^b$ is independently selected from $C_{1-6}$ alkyl, aryl, cycloalkyl, heteroaryl, and heterocycloalkyl; each of which is optionally substituted with 1, 2, 3, 4, or 5 substituents independently selected from $C_{1-6}$ alkyl, $C_{1-6}$ haloalkyl, halo, CN, and $OR^{a5}$;

each $OR^{a2}$ and $OR^{a5}$ is independently selected from H and $C_{1-4}$ alkyl;

Ar is a moiety of formula:

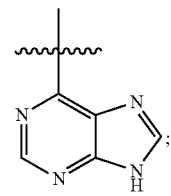 [SMILES: *c1ncnc2[nH]cnc12]

$R^1$ is $C_{1-6}$ alkyl; and $R^2$, $R^3$, $R^4$, and $R^5$ are each independently selected from H, halo, CN, $C_{1-6}$ alkyl, and $C_{1-6}$ haloalkyl.

In some embodiments, either X or Y is N.

In some embodiments, the compound is a compound of Formula II:

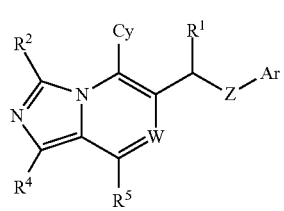

or a pharmaceutically acceptable salt thereof.

In some embodiments, the compound is a compound of Formula III:

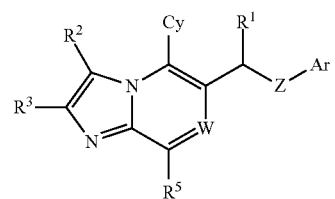

or a pharmaceutically acceptable salt thereof.

In some embodiments, the compound is a compound of Formula IIa:

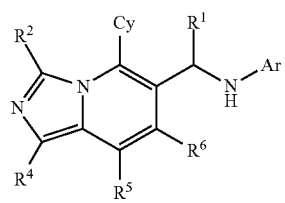

or a pharmaceutically acceptable salt thereof.

In some embodiments, the compound is a compound of Formula IIIa:

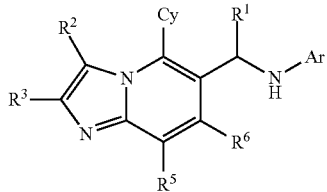

or a pharmaceutically acceptable salt thereof.

In some embodiments, the compound is a compound of Formula IV:

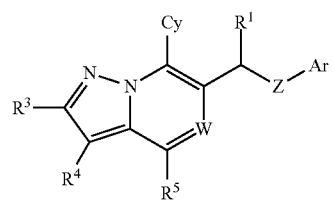

or a pharmaceutically acceptable salt thereof.

In some embodiments, the compound is a compound of Formula IVa:

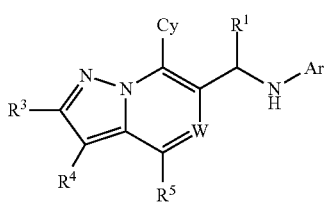

or a pharmaceutically acceptable salt thereof.

In some embodiments, the compound is selected from:
N-{1-[8-Chloro-5-(3-fluorophenyl)imidazo[1,2-a]pyridin-6-yl]ethyl}-9H-purin-6-amine;
N-{1-[8-Chloro-5-(3-fluorophenyl)-3-methylimidazo[1,5-a]pyridin-6-yl]ethyl}-9H-purin-6-amine; and
N-{1-[8-chloro-5-(3-fluorophenyl)imidazo[1,5-a]pyridin-6-yl]ethyl}-9H-purin-6-amine;
or a pharmaceutically acceptable salt of any of the aforementioned.

In some embodiments, the compound is selected from:
N-{1-[5-(4-Acetylpiperazin-1-yl)-8-chloroimidazo[1,5-a]pyridin-6-yl]ethyl}-9H-purin-6-amine;
N-(1-{8-chloro-5-[4-(methylsulfonyl)piperazin-1-yl]imidazo[1,5-a]pyridin-6-yl}ethyl)-9H-purin-6-amine;
tert-Butyl 4-{8-chloro-6-[1-(9H-purin-6-ylamino)ethyl]imidazo[1,5-a]pyridin-5-yl}piperazine-1-carboxylate;
N-(1-{8-Chloro-5-[4-(cyclopropylcarbonyl)piperazin-1-yl]imidazo[1,5-a]pyridin-6-yl}ethyl)-9H-purin-6-amine;
N-(1-{8-chloro-5-[4-(methoxy acetyl)piperazin-1-yl]imidazo[1,5-a]pyridin-6-yl}ethyl)-9H-purin-6-amine;
N-[1-(8-Chloro-5-piperazin-1-ylimidazo[1,5-a]pyridin-6-yl)ethyl]-9H-purin-6-amine dihydrochloride;
3-(4-{8-Chloro-6-[1-(9H-purin-6-ylamino)ethyl]imidazo[1,5-a]pyridin-5-yl}piperazin-1-yl)-3-oxopropanenitrile;
N-[1-(8-Chloro-5-{4-[(1-methyl-1H-pyrazol-4-yl)carbonyl]piperazin-1-yl}imidazo[1,5-a]pyridin-6-yl)ethyl]-9H-purin-6-amine;
N-(1-{8-Chloro-5-[4-(2-methoxyethyl)piperazin-1-yl]imidazo[1,5-a]pyridin-6-yl}ethyl)-9H-purin-6-amine;
(4-{8-Chloro-6-[1-(9H-purin-6-ylamino)ethyl]imidazo[1,5-a]pyridin-5-yl}piperazin-1-yl)acetonitrile;
N-(1-{8-Chloro-5-[4-(4,4,4-trifluorobutyl)piperazin-1-yl]imidazo[1,5-a]pyridin-6-yl}ethyl)-9H-purin-6-amine;
N-{1-[8-Chloro-5-(4-cyclobutylpiperazin-1-yl)imidazo[1,5-a]pyridin-6-yl]ethyl}-9H-purin-6-amine;
N-(1-{8-Chloro-5-[4-(tetrahydrofuran-2-ylmethyl)piperazin-1-yl]imidazo[1,5-a]pyridin-6-yl}ethyl)-9H-purin-6-amine;
N-(1-{8-Chloro-5-[4-(cyclopropylmethyl)piperazin-1-yl]imidazo[1,5-a]pyridin-6-yl}ethyl)-9H-purin-6-amine;
N-{1-[8-Chloro-5-(3-fluorophenyl)imidazo[1,5-a]pyridin-6-yl]propyl}-9H-purin-6-amine;
N-{1-[8-Chloro-5-(3,5-difluorophenyl)-3-methylimidazo[1,5-a]pyridin-6-yl]ethyl]-9H-purin-6-amine;
N-{1-[8-Chloro-5-(3,5-difluorophenyl)-3-methylimidazo[1,5-a]pyridin-6-yl]propyl}-9H-purin-6-amine;
N-(1-{8-Chloro-5-[(3R)-3-methoxypyrrolidin-1-yl]imidazo[1,5-a]pyridin-6-yl}ethyl)-9H-purin-6-amine;
N-(1-{8-Chloro-5-[(3S)-3-methoxypyrrolidin-1-yl]imidazo[1,5-a]pyridin-6-yl}ethyl)-9H-purin-6-amine;
(3R)-1-{8-Chloro-6-[1-(9H-purin-6-ylamino)ethyl]imidazo[1,5-a]pyridin-5-yl}pyrrolidin-3-ol;
(3S)-1-{8-Chloro-6-[1-(9H-purin-6-ylamino)ethyl]imidazo[1,5-a]pyridin-5-yl}pyrrolidin-3-ol;
N-{1-[8-Chloro-5-(diethylamino)-3-methylimidazo[1,5-a]pyridin-6-yl]ethyl}-9H-purin-6-amine;
N-{1-[4-chloro-7-(3-fluorophenyl)pyrazolo[1,5-a]pyridin-6-yl]ethyl}-9H-purin-6-amine;
N-{1-[4-fluoro-7-(3-fluorophenyl)pyrazolo[1,5-a]pyridin-6-yl]ethyl}-9H-purin-6-amine; and
N-{1-[4-chloro-7-(3-methoxyphenyl)pyrazolo[1,5-a]pyridin-6-yl]ethyl}-9H-purin-6-amine;
or a pharmaceutically acceptable salt of any of the aforementioned.

In some embodiments, the compound is selected from:
N-{1-[8-Fluoro-5-(3-fluorophenyl)imidazo[1,5-a]pyridin-6-yl]ethyl}-9H-purin-6-amine;
N-{1-[5-(4-Acetylpiperazin-1-yl)-8-bromo imidazo[1,5-a]pyridin-6-yl]ethyl}-9H-purin-6-amine;
5-(4-Acetylpiperazin-1-yl)-6-[1-(9H-purin-6-ylamino)ethyl]imidazo[1,5-a]pyridine-8-carbonitrile; and
N-{1-[5-(4-Acetylpiperazin-1-yl)-8-methylimidazo[1,5-a]pyridin-6-yl]ethyl}-9H-purin-6-amine;
or a pharmaceutically acceptable salt of any of the aforementioned.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "$C_{n-m}$" is referred to indicate $C_{1-4}$, $C_{1-6}$, and the like, wherein n and m are integers and indicate the number of carbons, wherein n-m indicates a range which includes the endpoints.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, the term "alkylene" refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl", employed alone or in combination with other terms, refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "$C_{n-m}$ alkylamino", employed alone or in combination with other terms, refers to a group of formula —NH(alkyl), wherein the alkyl group has n to m carbon atoms. In some embodiments, the alkyl group has 1 to 6 or 1 to 4 carbon atoms.

As used herein, the term "$C_{n-m}$ alkoxycarbonyl", employed alone or in combination with other terms, refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl", employed alone or in combination with other terms, refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino", employed alone or in combination with other terms, refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonylamino", employed alone or in combination with other terms, refers to a group of formula —NHS(O)$_2$-alkyl, wherein the alkyl group has n to m carbon atoms. In some embodiments, the alkyl group has 1 to 6 or 1 to 4 carbon atoms.

As used herein, the term "aminosulfonyl", employed alone or in combination with other terms, refers to a group of formula —S(O)$_2$NH$_2$, wherein the alkyl group has n to m carbon atoms.

As used herein, the term "$C_{n-m}$ alkylaminosulfonyl", employed alone or in combination with other terms, refers to a group of formula —S(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonyl", employed alone or in combination with other terms, refers to a group of formula —S(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminosulfonylamino", employed alone or in combination with other terms, refers to a group of formula —NHS(O)$_2$NH$_2$.

As used herein, the term "$C_{n-m}$ alkylaminosulfonylamino", employed alone or in combination with other terms, refers to a group of formula —NHS(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonylamino", employed alone or in combination with other terms, refers to a group of formula —NHS(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino", employed alone or in combination with other terms, refers to a group of formula —NHC(O)NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminocarbonylamino", employed alone or in combination with other terms, refers to a group of formula —NHC(O)N(alkyl)$_2$, wherein each alkyl group independently has n to m carbon atoms. In some embodiments, each alkyl group has, independently, 1 to 6 or 1 to 4 carbon atoms.

As used herein, the term "$C_{n-m}$ alkylcarbamyl", employed alone or in combination with other terms, refers to a group of formula —C(O)—NH(alkyl), wherein the alkyl group has n to m carbon atoms. In some embodiments, the alkyl group has 1 to 6 or 1 to 4 carbon atoms.

As used herein, the term "thio" refers to a group of formula —S—H.

As used herein, the term "$C_{n-m}$ alkylthio", employed alone or in combination with other terms, refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl", employed alone or in combination with other terms, refers to a group of formula —S(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl", employed alone or in combination with other terms, refers to a group of formula —S(O)$_2$-alkyl, wherein the alkyl group has n to m carbon atoms. In some embodiments, the alkyl group has 1 to 6 or 1 to 4 carbon atoms.

As used herein, the term "amino", employed alone or in combination with other terms, refers to a group of formula —NH$_2$.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is C$_{6-10}$ aryl. In some embodiments, the aryl group is a naphthalene ring or phenyl ring. In some embodiments, the aryl group is phenyl.

As used herein, the term "arylalkyl" refers to a group of formula -alkylene-aryl. In some embodiments, arylalkyl is C$_{6-10}$ aryl-C$_{1-3}$ alkyl. In some embodiments, arylalkyl is phenyl-C$_{1-3}$ alkyl. In some embodiments, arylalkyl is benzyl.

As used herein, the term "carbamyl", employed alone or in combination with other terms, refers to a group of formula —C(O)NH$_2$.

As used herein, the term "carbonyl", employed alone or in combination with other terms, refers to a —C(O)— group.

As used herein, the term "carboxy", employed alone or in combination with other terms, refers to a group of formula —C(O)OH.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is C$_{3-12}$ cycloalkyl, which is monocyclic or bicyclic. In some embodiments, cycloalkylalkyl is monocyclic C$_{3-6}$ cycloalkyl. Exemplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula -alkylene-cycloalkyl. In some embodiments, cycloalkylalkyl is C$_{3-12}$ cycloalkyl-C$_{1-3}$ alkyl, wherein the cycloalkyl portion is monocyclic or bicyclic. In some embodiments, cycloalkylalkyl is C$_{3-6}$ cycloalkyl-C$_{1-3}$ alkyl, wherein the cycloalkyl portion is monocyclic.

As used herein, the term "di(C$_{n-m}$-alkyl)amino", employed alone or in combination with other terms, refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "di(C$_{n-m}$-alkyl)carbamyl", employed alone or in combination with other terms, refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, "C$_{n-m}$ haloalkoxy", employed alone or in combination with other terms, refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6 or 1 to 4 carbon atoms.

As used herein, the term "C$_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6 or 1 to 4 carbon atoms.

As used herein, the term "fluorinated C$_{n-m}$ haloalkyl" refers to a C$_{n-m}$ haloalkyl wherein the halogen atoms are selected from fluorine. In some embodiments, fluorinated C$_{n-m}$ haloalkyl is fluoromethyl, difluoromethyl, or trifluoromethyl. In some embodiments, the alkyl group has 1 to 6 or 1 to 4 carbon atoms.

As used herein, "halosulfanyl" refers to a sulfur group having one or more halogen substituents. Example halosulfanyl groups include pentahalosulfanyl groups such as SF$_5$.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is C$_{1-9}$ heteroaryl, which is monocyclic or bicyclic and which has 1, 2, 3, or 4 heteroatom ring members independently selected from nitrogen, sulfur and oxygen. In some embodiments, heteroarylalkyl is monocyclic C$_{1-5}$ heteroaryl, having which has 1, 2, 3, or 4 heteroatom ring members independently selected from nitrogen, sulfur and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like. In some embodiments, the heteroaryl is a 5-membered ring heteroaryl, a six-membered ring heteroaryl, or a bicyclic azaheteroaryl.

As used herein, the term "heteroarylalkyl" refers to a group of formula -alkylene-heteroaryl. In some embodiments, heteroarylalkyl is C$_{1-9}$ heteroaryl-C$_{1-3}$ alkyl, wherein the heteroaryl portion is monocyclic or bicyclic and has 1, 2, 3, or 4 heteroatom ring members independently selected from nitrogen, sulfur and oxygen. In some embodiments, heteroarylalkyl is C$_{1-5}$ heteroaryl-C$_{1-3}$ alkyl, wherein the heteroaryl portion is monocyclic and has 1, 2, 3, or 4 heteroatom ring members independently selected from nitrogen, sulfur and oxygen.

A five-membered ring heteroaryl is a heteroaryl with a ring having five ring atoms wherein one or more (e.g., 1, 2, 3, or 4) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. In some embodiments, the six-membered ring heteroaryl is a heteroaryl with a ring having six ring atoms wherein one or more (e.g., 1, 2, or 3) ring atoms is N. Exemplary six-membered ring heteroaryls are pyridyl, pyrazinyl, pyrimidinyl, triazinyl and pyridazinyl.

In some embodiments, heteroaryl (e.g., Ar supra) is bicyclic azaheteroaryl, as defined infra, or a six-membered heteroaryl ring, wherein 1, 2, or 3 ring atoms of said six-membered ring heteroaryl is N. In some embodiments, heteroaryl is a six-membered ring heteroaryl selected from pyridyl, pyrazinyl, pyrimidinyl, triazinyl and pyridazinyl. In some embodiments, heteroaryl is pyridyl. In some embodiments, heteroaryl is pyrazinyl. In some embodiments, heteroaryl is pyrimidinyl. In some embodiments, heteroaryl is triazinyl. In some embodiments, heteroaryl is pyridazinyl.

As used herein, the term "bicyclic azaheteroaryl", employed alone or in combination with other terms, refers to a bicyclic fused heteroaryl group having 1, 2, 3, or 4 nitrogen ring members. The bicyclic azaheteroaryl group may optionally have O or S heteroatom ring members in addition to the nitrogen ring members. In some embodiments, the only heteroatom ring members in the bicyclic azaheteroaryl group are nitrogen heteroatoms. In some embodiments, the bicyclic azaheteroaryl group is $C_{4-8}$ bicyclic azaheteroaryl, which has 8 to 10 ring forming atoms independently selected from carbon, nitrogen, sulfur and oxygen, wherein 1, 2, 3, or 4 of the ring forming atoms are independently selected from nitrogen, sulfur and oxygen provided that at least one ring atom is nitrogen. In some embodiments, bicyclic azaheteroaryl is a purine ring.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1,2,3,4-tetrahydro-quinoline, azetidine, azepane, pyrrolidine, piperidine, piperidine, piperazine, morpholine, thiomorpholine, and pyran.

As used herein, the term "heterocycloalkylalkyl" refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration at the carbon attached to $R^1$. In some embodiments, the compound has the (S)-configuration at the carbon attached to $R^1$.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. For example, purine includes the 9H and a 7H tautomeric forms:

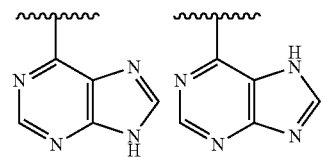

Compounds of the invention can include both the 9H and 7H tautomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of Compounds of the Invention can Involve the Protection and Deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Example synthetic methods for preparing compounds of Formula I, wherein Z is NR$^4$, are provided in Scheme I. An ester compound of formula (a) can be hydrolyzed, followed by direct activation of the resultant carboxylic acid with a coupling agent (e.g. HBTU, HATU) and then reaction with N,O-dimethylhydroxylamine to give a N-methoxy-N-methylcarboxamide derivative of formula (b). Alternatively, the carboxylic acid can be converted to an acid chloride and then reacted with N,O-dimethylhydroxylamine or appropriate derivative (e.g., N,O-dimethylhydroxylamine HCl) to give a N-methoxy-N-methylcarboxamide derivative of formula (b). The carboxamide (b) may then be reacted with a Grignard reagent of formula (c) to give a ketone of formula (d). The ketone (d) can be converted to a compound of Formula I by reductive amination, followed by reaction with an appropriate alkylating agent R$^4$X (e.g., MeI) and then a heteroaryl halide compound (e.g., Ar—X). The reaction of amine with R$^4$ can be eliminated to give compounds of Formula I where R$^4$ is H.

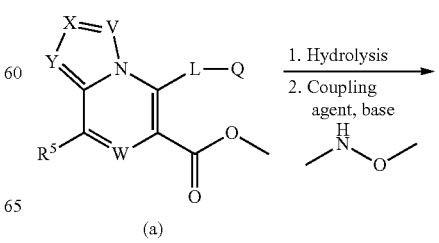

Scheme I

1. Hydrolysis
2. Coupling agent, base (a)

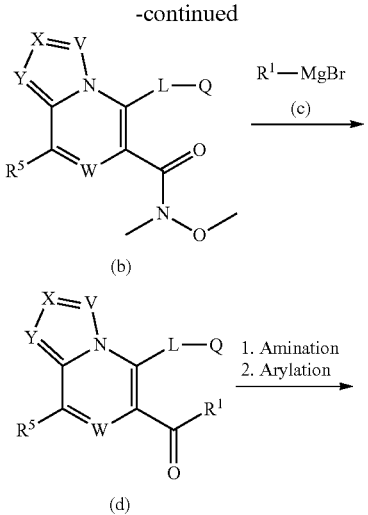

Alternatively, compounds of Formula I, wherein Z is S, O or a bond, can be synthesized as shown in Scheme II. The ketone of formula (d) from Scheme I can be first reduced to give the alcohol of formula (d-1). The hydroxyl group of compound (d-1) can be transformed to a thiol group by activation with mesyl chloride to form a compound of formula (i), followed by conversion to the thioacetate and cleavage of the acetate to afford a thiol of formula (ii). The thiol (ii) or hydroxyl compound (d-1) can be reacted with an appropriate heteroaryl halide compound (e.g., Ar—Br) to give a compound of formula (iii) or (iv), respectively, with or without a catalyst. Alternatively, mesylate (i) can be reacted with aryl or heteroaryl thiol (e.g., Ar—SH) to give a compound of formula (iii). The mesylate (i) can also be reacted with a heteroaryl compound (e.g., Ar—H, wherein H is attached to a nitrogen atom in Ar) to give a compound of formula (v). Appropriate Ar—X compounds useful in Scheme I or II, or Ar—H compounds useful in Scheme II, are commercially available or can be prepared by published synthetic methods (e.g., wherein Ar is purine, pyridine, pyrazine, pyrimidine, triazine or pyridazine, each substituted with 0, 1 or 2 independently selected $R^D$ groups). In some embodiments, Ar is purine substituted by 0, 1, or 2 independently selected $R^D$ groups. In some embodiments, Ar is pyridine substituted by 0, 1, or 2 independently selected $R^D$ groups. In some embodiments, Ar is pyrazine substituted by 0, 1, or 2 independently selected $R^D$ groups. In some embodiments, Ar is pyrimidine substituted by 0, 1, or 2 independently selected $R^D$ groups. In some embodiments, Ar is triazine substituted by 0, 1, or 2 independently selected $R^D$ groups. In some embodiments, Ar is pyridazine substituted by 0, 1, or 2 independently selected $R^D$ groups.

Scheme II

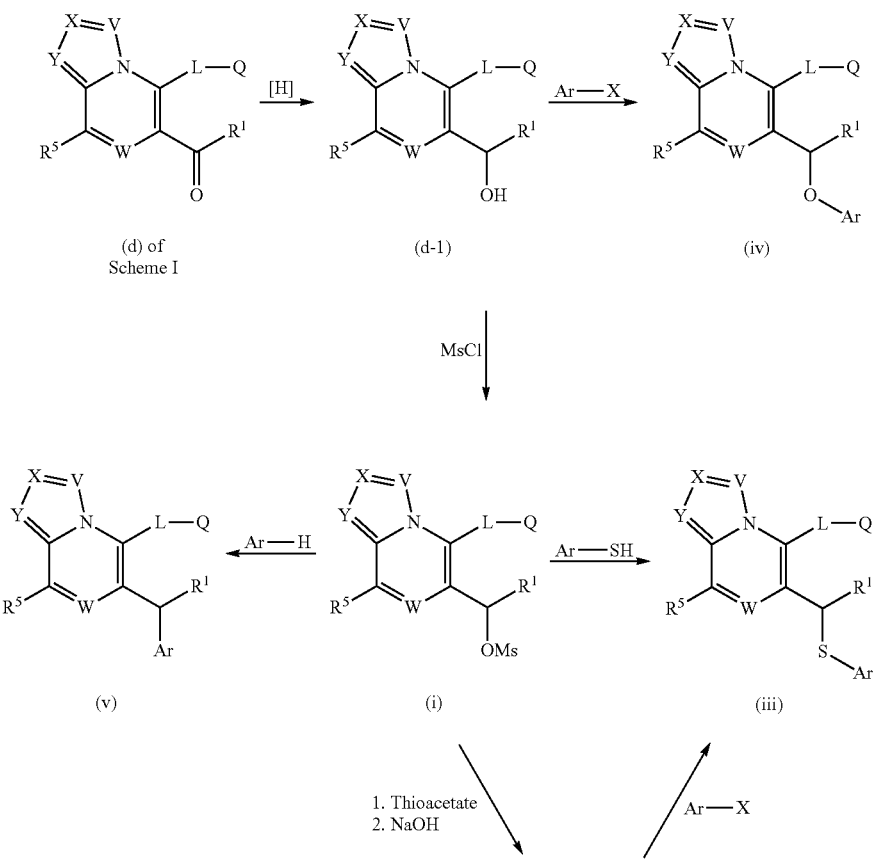

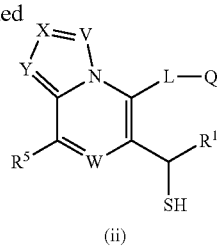

Compounds of Formula II can be synthesized as shown in Scheme III. Accordingly, a carboxylic acid of formula (i) is first reacted to form an ester (e.g., a methyl ester), followed by Suzuki coupling with an appropriate boronic ester or acid of formula (ii) (e.g., wherein R is independently hydrogen or alkyl, or 2 R groups together with the oxygen atoms and boron atom form a cyclic ester) to form a compound of formula (iii). Compound (iii) can then be oxidized to form a N-oxide of formula (iv). Compound (iv) is then reacted with cyanotrimethylsilane to form a compound of formula (v). The cyano group of compound (v) can then be reduced to form an amine of formula (vi), which can be acylated with a compound of formula $R^2CO$—$X^1$ or $X^1CO$—$X^1$ (wherein $X^1$ is an appropriate leaving group such as halo) followed by dehydration to give a compound of formula (a). Compounds of Formula II can then be synthesized as shown in Scheme I or II. For example, compounds of Formula II, wherein Z is $NR^4$, can be formed by substituting the compound of formula (v) or (a) of Scheme III for the compound of formula (a) in Scheme I. Alternatively, compounds of Formula II, wherein Z is O, S, or a bond, can be formed by first substituting the compound of formula (v) or (a) of Scheme III for the compound of formula (a) in Scheme I and then converting it to a compound of formula (d). The compound of formula (d) can then be converted to compounds of Formula II, wherein Z is O, S, or a bond, by the steps shown in Scheme II.

Scheme III

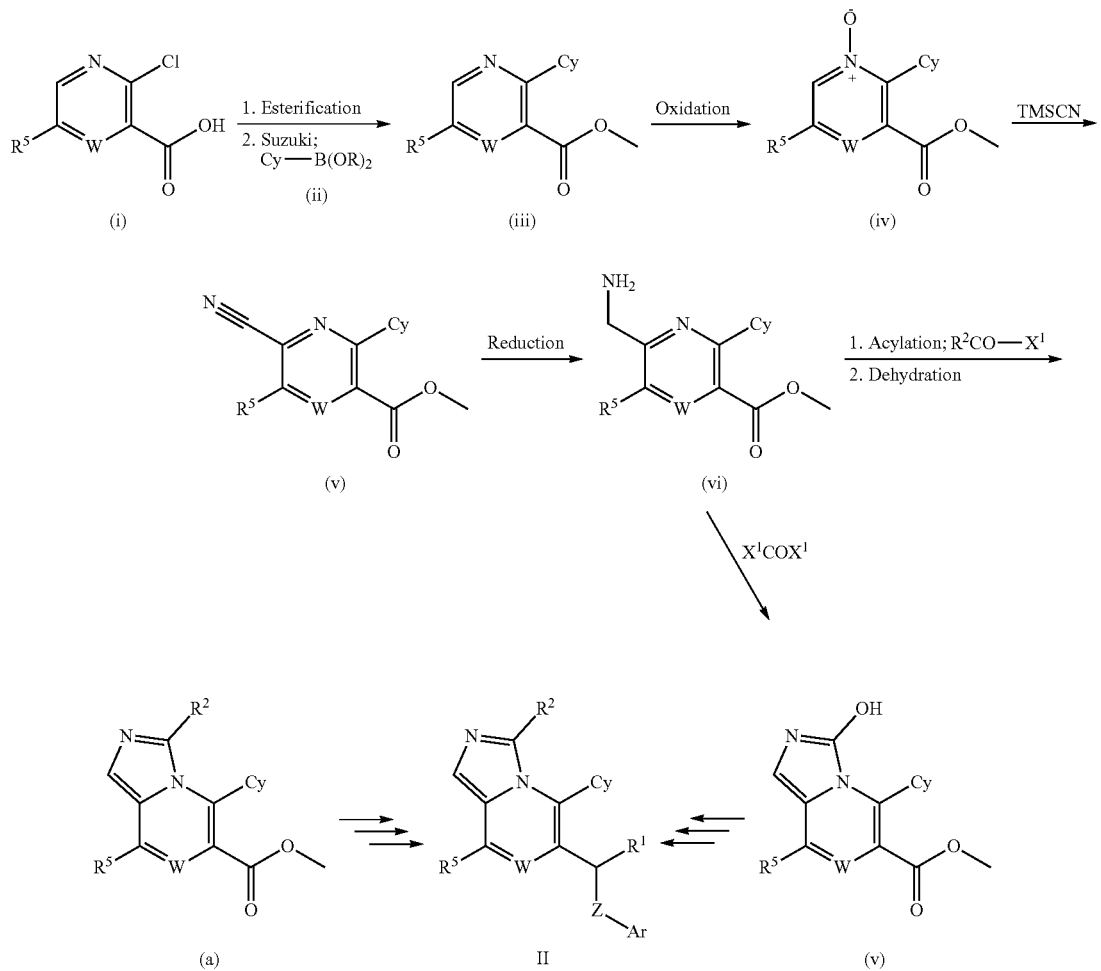

Compounds of Formula III can be synthesized as shown in Scheme IV. Accordingly, a carboxylic acid of formula (i) is first reacted to form an ester (e.g., a methyl ester), followed by a Suzuki, Negishi or Stille transition metal mediated coupling (e.g., Suzuki coupling of an appropriate boronic ester or acid of formula (ii) (e.g., wherein R is independently hydrogen or alkyl, or 2 R groups together with the oxygen atoms and boron atom form a cyclic ester)) to form a compound of formula (iii). Compound (iii) can then be oxidized to form a N-oxide of formula (iv). Compound (iv) is then reacted with phosphorous trichloride to form a chloride of formula (v). Compound (v) can then be reacted with 2,4-dimethoxybenzyl-amine (DMB-NH$_2$), followed by reaction with an acid to form an amine of formula (vi). The compound of formula (vi) can then be reacted with a compound of formula (vii), followed by dehydration to give a compound of formula (viii). Compounds of Formula III can then be synthesized as shown in Scheme I or II. For example, compounds of Formula III, wherein Z is NR$^4$, can be formed by substituting the compound of formula (viii) of Scheme IV for the compound of formula (a) in Scheme I. Alternatively, compounds of Formula III, wherein Z is O, S, or a bond, can be formed by first substituting the compound of formula (viii) of Scheme IV for the compound of formula (a) in Scheme I and then converting it to a compound of formula (d). The compound of formula (d) can then be converted to compounds of Formula II, wherein Z is O, S, or a bond, by the steps shown in Scheme II.

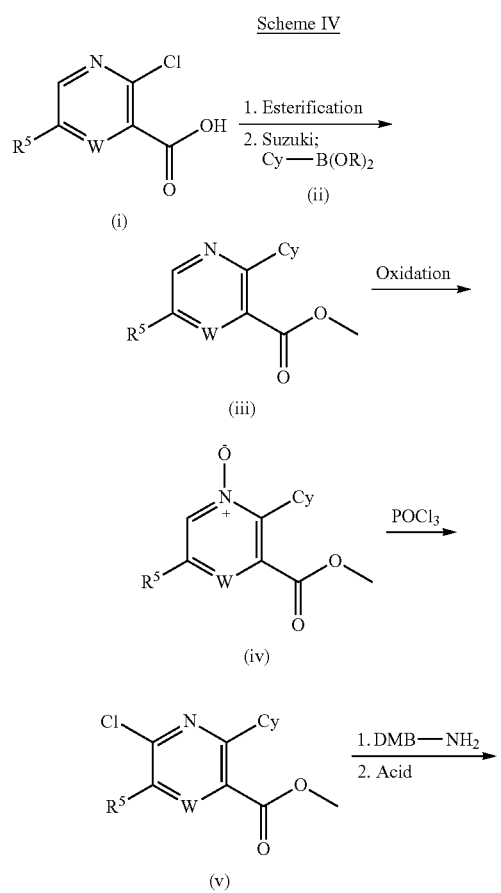

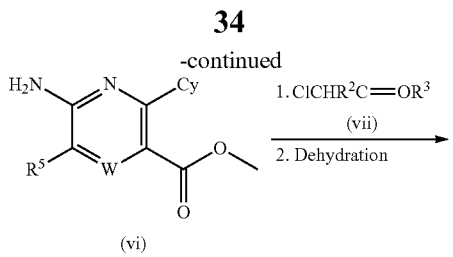

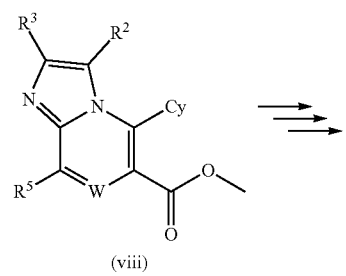

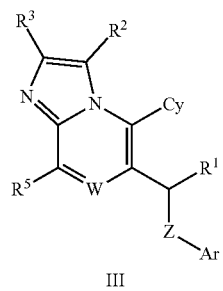

Compounds of Formula II can be also synthesized as shown in Scheme V. Accordingly, a cyano group of compound (i) can then be reduced to form an amine of formula (ii), which can be acylated with a compound of formula R$^2$CO—X$^1$ (wherein X$^1$ is an appropriate leaving group such as halo), followed by halogenation (e.g., NX$^2$S wherein X$^2$ is a halogen) to give a compound of formula (iii). Transition metal mediated cross coupling (Suzuki, Stille, Negishi coupling, etc.) of a compound of formula (iv) and subsequent dehydration (e.g., POCl$_3$) can give a compound of formula (v). Compounds of Formula II can then be synthesized as shown in Scheme I or II. For example, compounds of Formula II, wherein Z is NR$^4$, can be formed by substituting the compound of formula (v) of Scheme V for the compound of formula (a) in Scheme I. Alternatively, compounds of Formula II, wherein Z is O, S, or a bond, can be formed by first substituting the compound of formula (v) of Scheme V for the compound of formula (a) in Scheme I and then converting it to a compound of formula (d). The compound of formula (d) can then be converted to compounds of Formula II, wherein Z is O, S, or a bond, by the steps shown in Scheme II.

Scheme V

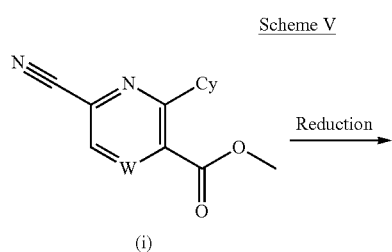

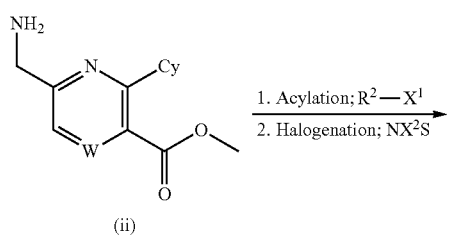

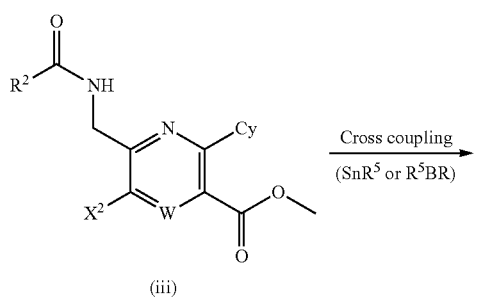

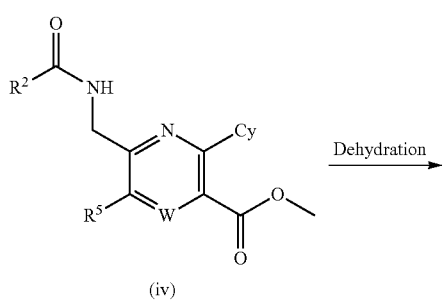

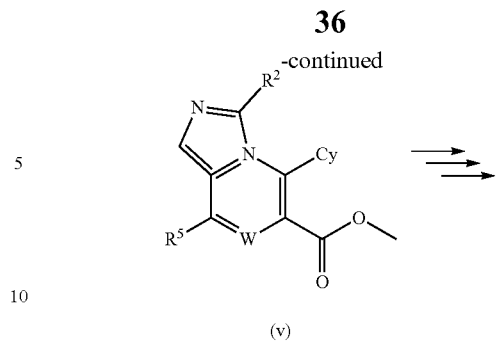

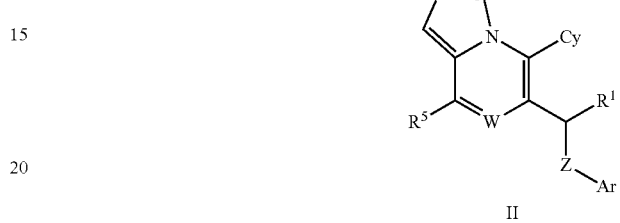

Compounds of Formula II can also be synthesized as shown in Scheme VI. Accordingly, a carboxylic acid of formula (i) is first reacted to form an ester (e.g., a methyl ester), followed oxidation to form the N-oxide of formula (ii). Compound (ii) is then reacted with cyanotrimethylsilane to form a compound of formula (iii). Compound (iii) can be coupled to a compound of formula Cy (wherein Cy is a cyclic amine) to form a compound of formula (iv). The cyano group of compound (iv) can then be reduced to form an amine of formula (v), which can be acylated with a compound of formula $R^2CO$—$X^1$ (wherein $X^1$ is an appropriate leaving group such as halo), followed by dehydration (e.g., $POCl_3$) to give a compound of formula (vi). Alternatively, amine of formula (v), which can be cyclized with a compound of formula $X^1CO$—$X^1$ (wherein $X^1$ is an appropriate leaving group such as halo) to give a compound of formula (vii). Compounds of Formula II can then be synthesized as shown in Scheme I or II. For example, compounds of Formula II, wherein Z is $NR^4$, can be formed by substituting the compound of formula (vi) or (vii) of Scheme VI for the compound of formula (a) in Scheme I. Alternatively, compounds of Formula II, wherein Z is O, S, or a bond, can be formed by first substituting the compound of formula (vi) or (vii) of Scheme VI for the compound of formula (a) in Scheme I and then converting it to a compound of formula (d). The compound of formula (d) can then be converted to compounds of Formula II, wherein Z is O, S, or a bond, by the steps shown in Scheme II.

Scheme VI

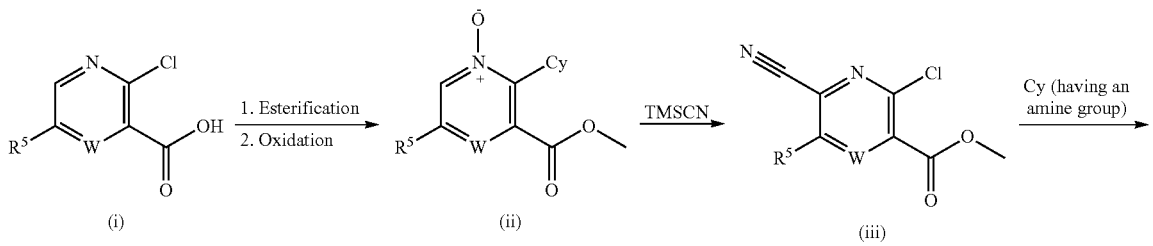

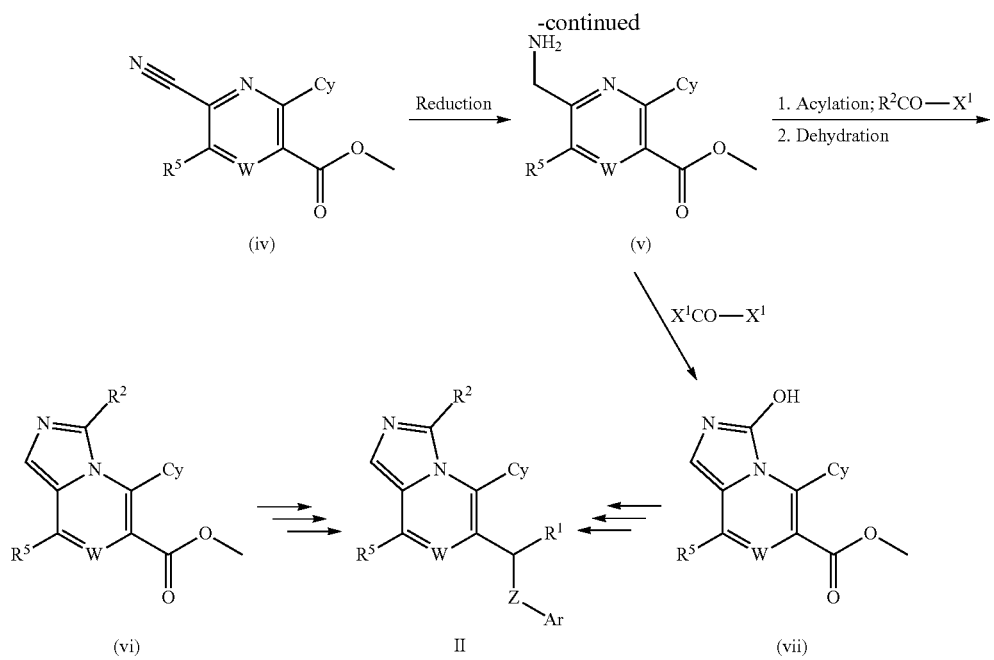

Compounds of Formula II can be also synthesized as shown in Scheme VII. Accordingly, a nitrile of formula (i) can be reduced with a suitable reducing agent (e.g., DIBAL) to form an aldehyde of formula (ii). Reaction with a Grignard reagent (e.g., $MgBrR^4$) can give an alcohol of formula (iii) that can be converted to an amine of formula (iv) by conversion to a leaving group (e.g., mesylation), displacement of the mesylated alcohol with $NaN_3$, and subsequent reduction (e.g., $H_2$ over Pd/C). The amine group of compound (iv) can then be acylated with a compound of formula $R^2CO-X^1$ (wherein $X^1$ is an appropriate leaving group such as halo), followed by dehydration (e.g., $POCl_3$) to give a compound of formula (v). Compounds of Formula I can then be synthesized as shown in Scheme I or II. For example, compounds of Formula I, wherein Z is $NR^4$, can be formed by substituting the compound of formula (v) of Scheme VII for the compound of formula (a) in Scheme I. Alternatively, compounds of Formula I, wherein Z is O, S, or a bond, can be formed by first substituting the compound of formula (v) of Scheme VII for the compound of formula (a) in Scheme I and then converting it to a compound of formula (d). The compound of formula (d) can then be converted to compounds of Formula I, wherein Z is O, S, or a bond, by the steps shown in Scheme II.

Scheme VII

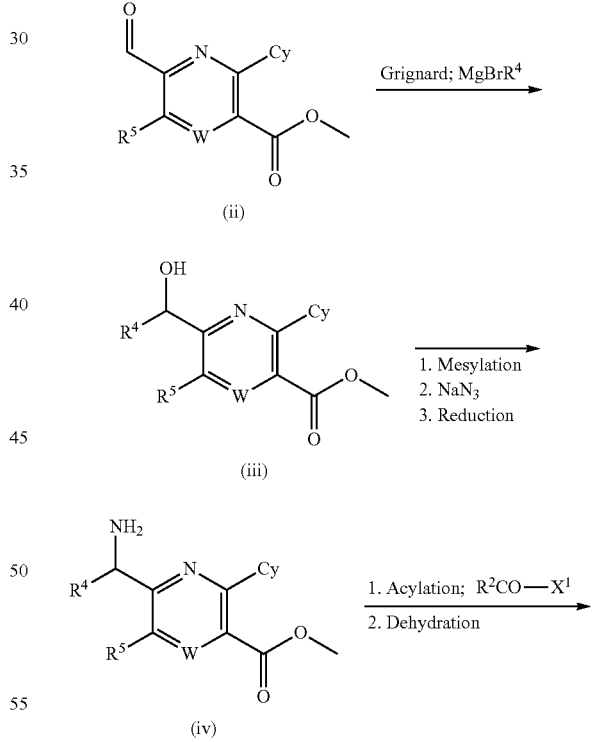

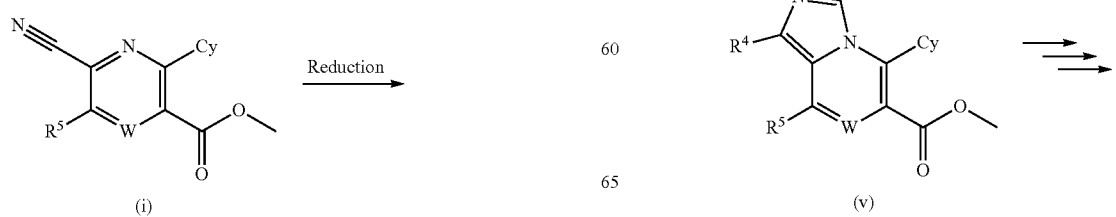

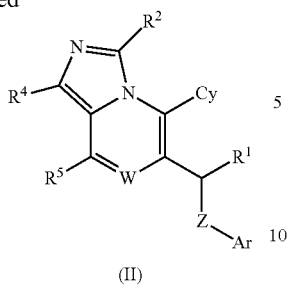

(II)

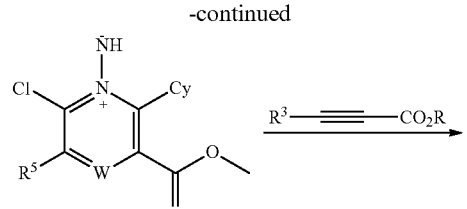

(iv)

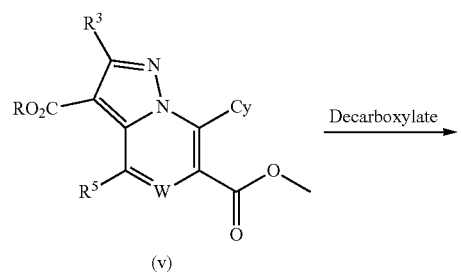

(v)

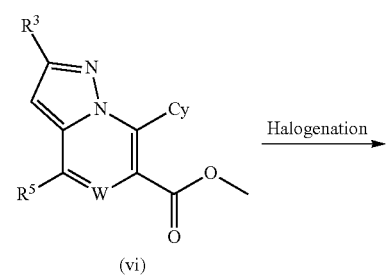

(vi)

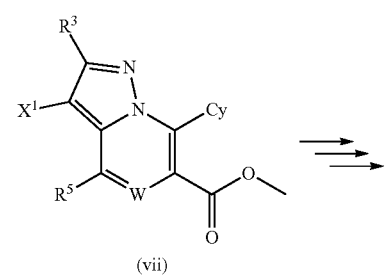

(vii)

Compounds of Formula IV can be also synthesized as shown in Scheme VIII. Accordingly, a carboxylic acid of formula (i) is first reacted to form an ester (e.g., a methyl ester), followed by a Suzuki, Negishi or Stille transition metal mediated coupling (e.g., Suzuki coupling of an appropriate boronic ester or acid of formula (ii) (e.g., wherein R is independently hydrogen or alkyl, or 2 R groups together with the oxygen atoms and boron atom form a cyclic ester)) to form a compound of formula (iii). Compound (iii) can then be amindated to form a N-amino of formula (iv). Compound (iv) is then reacted with a suitable acetylene to form a heterocycle of formula (v). Compound (v) can then be selectively decarboxylated (e.g., acid deprotection of R=tbutyl followed by decarboxylation) to form a heterocycle of formula (vi) which can be halogenated (e.g., $NX^1S$) to give compounds of formula (vii). Compounds of Formula IV can then be synthesized as shown in Scheme I or II. For example, compounds of Formula IV, wherein Z is $NR^A$, can be formed by substituting the compound of formula (vii) of Scheme VIII for the compound of formula (a) in Scheme I. Alternatively, compounds of Formula IV, wherein Z is O, S, or a bond, can be formed by first substituting the compound of formula (vii) of Scheme VIII for the compound of formula (a) in Scheme I and then converting it to a compound of formula (d). The compound of formula (d) can then be converted to compounds of Formula I, wherein Z is O, S, or a bond, by the steps shown in Scheme II.

Scheme VIII

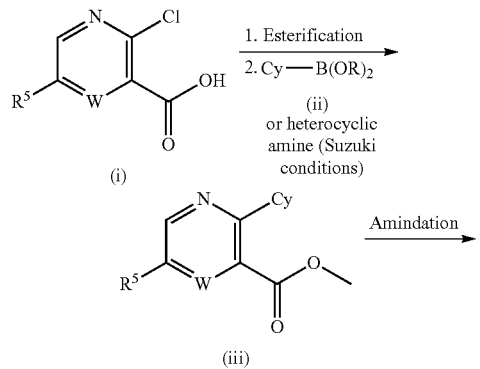

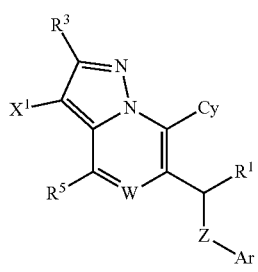

IV

Compounds of Formula I, wherein L is $NR^B$, O, S, or $C_{1-4}$ alkylene, can be also synthesized as shown in Scheme IX. Accordingly, an appropriately substituted heterocyclic chloride (i) can be reacted with an amine (e.g. $HNR^AQ$) alcohol (e.g., Q-OH), or thiol (e.g., Q-SH) to form compounds of formulas (ii), (iii) and (iv), respectively. In addition, compound (i) can be reacted under Suzuki, Heck, Negishi or Stille transition metal mediated coupling conditions (e.g., Suzuki coupling of an appropriate boronic ester or acid (e.g., Q-L-B(OR)$_2$ wherein R is independently hydrogen or alkyl, or 2 R groups together with the oxygen atoms and boron atom form a cyclic ester)) to form a compound of formula (v). Compounds of Formula I can then be synthesized as shown in Schemes I-IX. For example, compounds of Formula II, except wherein L=NR$^A$, S, O, or alkylene, can be formed by substituting the compound of formulas (ii, iii, iv, v, respectively) of Scheme IX, where R' is CN, for the compound of formula (iv) in Scheme VI. Compounds of Formula III, except wherein L=NR$^A$, S, O, or alkylene, can be formed by substituting the compound of formulas (ii, iii, iv, v, respectively) of Scheme IX, where R' is H, for the compound of formula (iii) in Scheme IV.

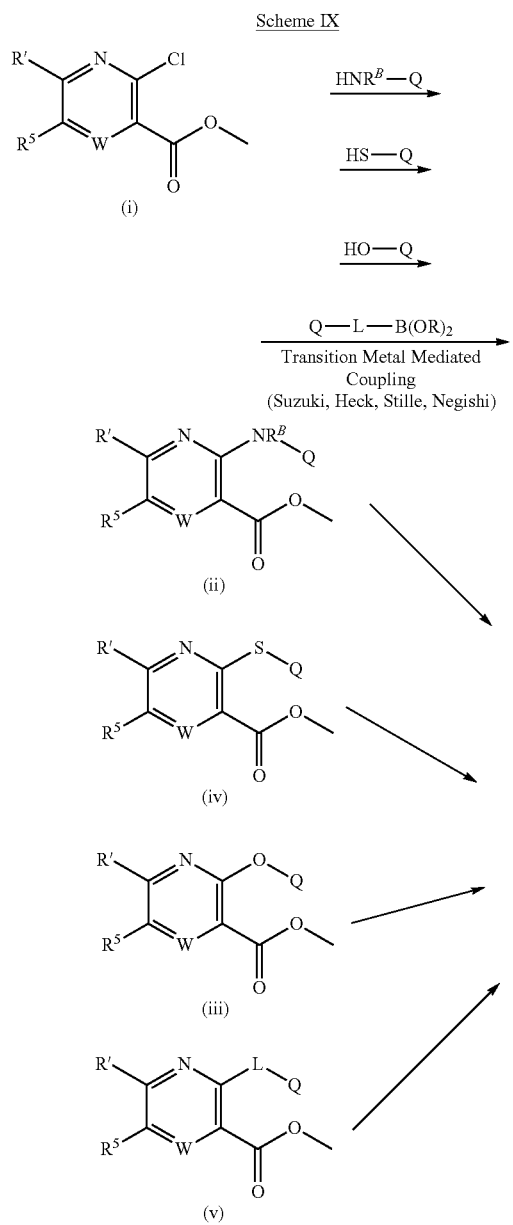

Scheme IX

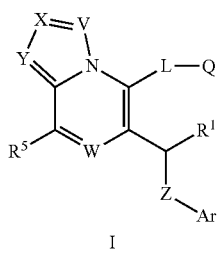

L is NR$^8$, S, O, or C$_{1-4}$ alkylene

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, atherosclerosis, inflammation, angiogenesis, pancreatitis, kidney disease, inflammatory bowel disease, myasthenia gravis, multiple sclerosis, or Sjögren's syndrome, and the like.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK, μ-MET, VEGFR, PDGFR, cKit, IGF-1R, RAF, FAK, and mTOR kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™ intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, and bendamustine (Treanda).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face mask tent, or intermittent positive pressure breathing machine Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline™, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro PI3K labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, one or more H atoms for any compound described herein is each replaced by a deuterium atom.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified. The term "rt" means retention time.

Example 1

N-{1-[8-Chloro-5-(3-fluorophenyl)imidazo[1,5-a]pyridin-6-yl]ethyl}-9H-purin-6-amine

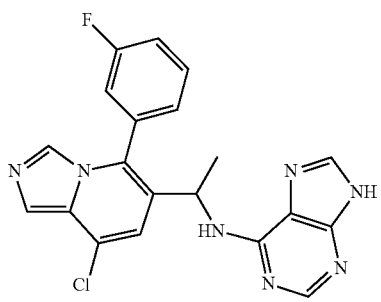 [SMILES: CC(Nc1ncnc2[nH]cnc12)c1cc(Cl)c2cncn2c1-c1cccc(F)c1]

Step A. Methyl 2,5-dichloronicotinate

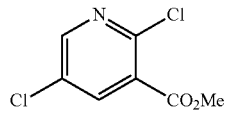

A solution of 2,5-dichloronicotinic acid (20 g, 0.10 mol) [OChem, 782D853] in dichloromethane (520 mL) was treated with 2 M oxalyl chloride in dichloromethane (160 mL, 310 mmol) followed by a few drops of N,N-dimethylformamide and stirred at 20° C. for 15 hours. The reaction mixture was concentrated, diluted with dichloromethane (200 mL), cooled to 0° C., treated with methanol (110 mL, 2.7 mol), and stirred at 0° C. for 5 minutes. The reaction mixture was concentrated to a crude residue. Purification by flash column chromatography using ethyl acetate in hexanes (0-80%) gave the desired product (19 g, 89%). LCMS calculated for $C_7H_6Cl_2NO_2$ (M+H)$^+$: m/z=206.0, 208.0. found: 205.8, 207.7.

Step B: Methyl 5-chloro-2-(3-fluorophenyl)nicotinate

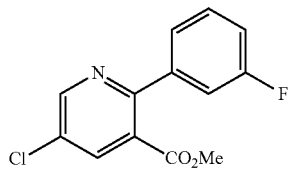 [SMILES: COC(=O)c1cc(Cl)cnc1-c1cccc(F)c1]

A solution of methyl 2,5-dichloronicotinate (8.2 g, 40 mmol), (3-fluorophenyl)boronic acid (6.1 g, 44 mmol), and potassium carbonate (12 g, 86 mmol) in water (71 mL) and 1,4-dioxane (190 mL) was degassed with nitrogen (10 minutes). The reaction mixture was treated with bis(triphenylphosphine)palladium(II) chloride (3.1 g, 4.4 mmol), degassed with nitrogen (10 minutes), and heated at 80° C. for 14.5 hours. The reaction mixture was diluted with ethyl acetate and water and filtered over celite. The aqueous layer was separated and re-extracted with ethyl acetate. The combined organic layers were washed with water and brine, dried with magnesium sulfate, filtered, and concentrated to a crude residue. Purification by flash column chromatography using ethyl acetate in hexanes (0-80%) gave the desired product (8.7 g, 83%). LCMS calculated for $C_{13}H_{10}ClFNO_2$ (M+H)$^+$: m/z=266.0. found: 265.8.

Step C: Methyl 5-chloro-2-(3-fluorophenyl)nicotinate 1-oxide

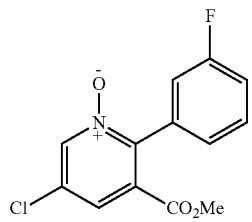

A solution of methyl 5-chloro-2-(3-fluorophenyl)nicotinate (11 g, 41 mmol) in ethaneperoxoic acid (30 mL, 100 mmol) was heated at 90° C. for 1 hour. Evaporation and purification by flash column chromatography with ethyl acetate in hexanes (0-50%) gave the desired compound (7.0 g, 68%). LCMS calculated for $C_{13}H_{10}ClFNO_3$ (M+H)$^+$: m/z=282.0. found: 281.8. $^1$H NMR (300 MHz, DMSO-d$_6$): δ 8.83 (s, 1H), 7.85 (s, 1H), 7.49 (m, 1H), 7.25 (m, 2H), 7.14 (m, 1H), 3.32 (s, 3H).

Step D: Methyl 5-chloro-6-cyano-2-(3-fluorophenyl)nicotinate

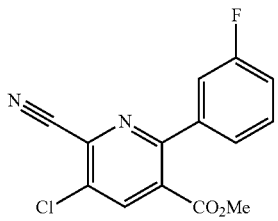 [SMILES: COC(=O)c1cc(Cl)c(C#N)nc1-c1cccc(F)c1]

Methyl 5-chloro-2-(3-fluorophenyl)nicotinate 1-oxide (2.9 g, 10 mmol) was stirred in acetonitrile (30 mL) with triethylamine (2.2 mL, 16 mmol) and trimethylsilyl cyanide (3.4 mL, 26 mmol) was added. The mixture was heated at 70° C. for 1 hour. Evaporation and purification by flash column chromatography using ethyl acetate in hexanes (0-20%) gave the desired compound (2.7 g, 90%). LCMS calculated for $C_{14}H_9ClFN_2O_2$ (M+H)$^+$: m/z=291.1. found: 290.8.

Step E: Methyl 6-(aminomethyl)-5-chloro-2-(3-fluorophenyl)nicotinate

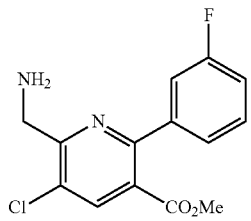

Methyl 5-chloro-6-cyano-2-(3-fluorophenyl)nicotinate (1.3 g, 4.5 mmol) was stirred in methanol (60 mL), and 5% palladium on carbon (1.0 g) was added. The mixture was degassed three times and placed under a balloon pressure of hydrogen for 4 hours. A solution of 0.5 M sodium methoxide in methanol (45 mL) was added and the mixture was filtered through celite. The filtrates were evaporated and the residue was triturated with dichloromethane. The solids were filtered and washed with dichloromethane to give the desired compound contaminated with 30% dechlorinated byproduct (1.3 g, 100%). LCMS calculated for $C_{14}H_{13}ClFN_2O_2$ (M+H)$^+$: m/z=295.1. found: 295.0.

Step F: Methyl 5-chloro-2-(3-fluorophenyl)-6-[(formylamino)methyl]nicotinate

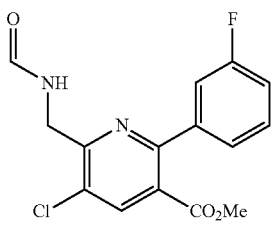

Methyl 6-(aminomethyl)-5-chloro-2-(3-fluorophenyl)nicotinate (1.1 g, 3.7 mmol) was stirred in formic acid (10 mL) and heated to 90° C. for 10 hours. Evaporation gave the crude material which was contaminated with the corresponding dechlorinated byproduct (1.1 g, quantitative). LCMS calculated for $C_{15}H_{13}ClFN_2O_3$ (M+H)$^+$: m/z=323.1. found: 322.9.

Step G: Methyl 8-chloro-5-(3-fluorophenyl)imidazo[1,5-a]pyridine-6-carboxylate

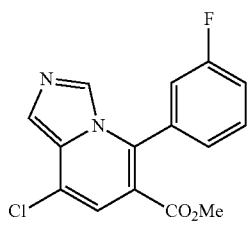 [SMILES: COC(=O)c1cc(Cl)c2cncn2c1-c1cccc(F)c1]

Methyl 5-chloro-2-(3-fluorophenyl)-6-[(formylamino)methyl]nicotinate (2.6 g, 8.5 mmol) was stirred in phosphoryl chloride (80 mL) and heated at 90° C. for 1 hour. Evaporation and purification by flash column chromatography with ethyl acetate in hexanes (0-100%) gave the desired compound (0.60 g, 40%). LCMS calculated for $C_{15}H_{11}ClFN_2O_2$ (M+H)$^+$: m/z=305.1. found: 304.9. $^1$H NMR (300 MHz, DMSO-d$_6$): δ 8.26 (s, 1H), 7.91 (s, 1H), 7.60 (m, 1H), 7.43 (m, 3H), 7.38 (m, 1H), 3.60 (s, 3H).

Step H: 8-Chloro-5-(3-fluorophenyl)imidazo[1,5-a]pyridine-6-carboxylic acid

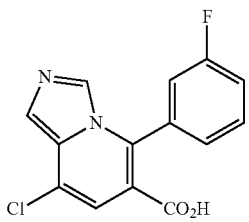 [SMILES: O=C(O)c1cc(Cl)c2cncn2c1-c1cccc(F)c1]

Methyl 8-chloro-5-(3-fluorophenyl)imidazo[1,5-a]pyridine-6-carboxylate (0.60 g, 2.0 mmol) was stirred in methanol (40 mL) and a solution of 3 N sodium hydroxide in water (10 mL, 40 mmol) was added. The mixture was stirred for 16 hours at room temperature, and glacial acetic acid (5 mL) was added. Evaporation gave a precipitate which was filtered and washed with water to give the desired compound (0.29 g, 50%). LCMS calculated for $C_{14}H_9ClFN_2O_2$ (M+H)$^+$: m/z=291.1. found: 290.9. $^1$H NMR (300 MHz, DMSO-d$_6$): δ 7.77 (s, 1H), 7.60 (m, 2H), 7.40 (m, 4H).

Step I: 8-Chloro-5-(3-fluorophenyl)-N-methoxy-N-methylimidazo[1,5-a]pyridine-6-carboxamide

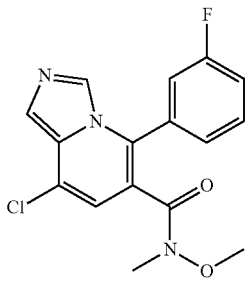 [SMILES: CON(C)C(=O)c1cc(Cl)c2cncn2c1-c1cccc(F)c1]

8-Chloro-5-(3-fluorophenyl)imidazo[1,5-a]pyridine-6-carboxylic acid (0.29 g, 1.0 mmol) was stirred in N,N-dimethylformamide (2.8 mL). N,N-Diisopropylethylamine (0.87 mL, 5.0 mmol), N,O-dimethylhydroxylamine hydrochloride (0.29 g, 3.0 mmol) and a solution of 0.6 N 1-hydroxy-7-azabenzotriazole in N,N-dimethylformamide (0.33 mL, 0.2 mmol) were added. The mixture was stirred for 5 minutes and N-(3-dimethylaminopropyl)-N'-ethylcarbodiimide hydrochloride (0.29 g, 1.5 mmol) was added. The mixture was stirred for 2 hours. The mixture was poured into saturated sodium bicarbonate and extracted into ethyl acetate 3×. The ethyl acetate extracts were combined and washed with water, dried over sodium sulfate, filtered, concentrated and purified by flash column chromatography with ethyl acetate in hexanes (0-80%) to give the desired compound (0.20 g, 60%). LCMS calculated for $C_{16}H_{14}ClFN_3O_2$ (M+H)$^+$: m/z=334.1.

found: 333.9. $^1$H NMR (300 MHz, DMSO-$d_6$): δ 8.10 (s, 1H), 7.60 (m, 2H), 7.42 (m, 3H), 7.20 (s, 1H), 3.41 (br s, 3H), 3.00 (s, 3H).

Step J: 1-[8-Chloro-5-(3-fluorophenyl)imidazo[1,5-a]pyridine-6-yl]ethanone

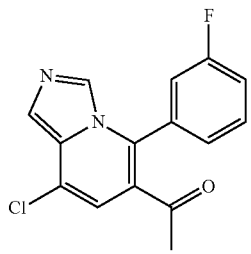 [SMILES: CC(=O)c1cc(Cl)c2cncn2c1-c1cccc(F)c1]

8-Chloro-5-(3-fluorophenyl)-N-methoxy-N-methylimidazo[1,5-a]pyridine-6-carboxamide (0.15 g, 0.45 mmol) was stirred in tetrahydrofuran (0.73 mL) and cooled to 0° C. A solution of 3.0 M methylmagnesium bromide (0.52 mL, 1.57 mmol) was added dropwise. The mixture was stirred at 0° C. for 30 minutes and at room temperature for 1 hour. The mixture was cooled to 0° C. and a solution of 1.0 M hydrogen chloride in water (1.8 mL) was added. The mixture was poured into saturated sodium bicarbonate and extracted into ethyl acetate 3×. The ethyl acetate extracts were combined and washed with water, dried over sodium sulfate, filtered, concentrated and purified by flash column chromatography with ethyl acetate in hexanes (0-80%) to give the desired compound (0.12 g, 93%). LCMS calculated for $C_{15}H_{11}ClFN_2O$ (M+H)$^+$: m/z=289.1. found: 288.9. $^1$H NMR (300 MHz, DMSO-$d_6$): δ 7.89 (s, 1H), 7.62 (m, 2H), 7.50 (m, 2H), 7.40 (m, 2H), 2.10 (s, 3H).

Step K: 1-[8-Chloro-5-(3-fluorophenyl)imidazo[1,5-a]pyridine-6-yl]ethanamine

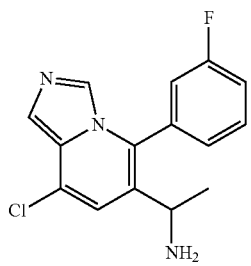 [SMILES: CC(N)c1cc(Cl)c2cncn2c1-c1cccc(F)c1]

1-[8-Chloro-5-(3-fluorophenyl)imidazo[1,5-a]pyridine-6-yl]ethanone (0.12 g, 0.42 mmol) and ammonium acetate (0.32 g, 4.2 mmol) were stirred in methanol (4.6 mL) and heated to 65° C. for 1 hour. Sodium cyanoborohydride (78 mg, 1.3 mmol) was added and the mixture was heated at 65° C. for 16 hours. The mixture was evaporated and the resultant residue was purified on RP-HPLC (XBridge C18 column, eluting with a gradient of acetonitrile/water containing 0.1% ammonium hydroxide, at flow rate of 60 mL/min) to give the desired product (51 mg, 42%). LCMS calculated for $C_{15}H_{14}ClFN_3$ (M+H)$^+$: m/z=290.1. found: 290.0. $^1$H NMR (300 MHz, DMSO-$d_6$): δ 7.63 (m, 2H), 7.41 (m, 3H), 7.35 (m, 2H), 3.60 (m, 1H), 1.18 (m, 3H).

Step L: N-{1-[8-Chloro-5-(3-fluorophenyl)imidazo[1,5-a]-pyridin-6-yl]ethyl}-9H-purin-6-amine

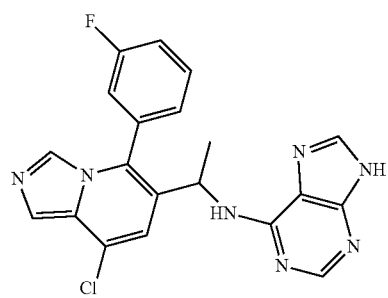 [SMILES: CC(Nc1ncnc2[nH]cnc12)c1cc(Cl)c2cncn2c1-c1cccc(F)c1]

1-[8-Chloro-5-(3-fluorophenyl)imidazo[1,5-a]pyridine-6-yl]ethanamine (23 mg, 79 μmol), 6-bromo-9H-purine (32 mg, 0.16 mmol, Aldrich 104981) and N,N-diisopropylethylamine (69 μL, 0.40 mmol) were stirred in ethanol (1.0 mL) and heated to 130° C. for 30 minutes in a microwave. The mixture was evaporated and the resultant residue was purified on RP-HPLC (XBridge C18 column, eluting with a gradient of acetonitrile/water containing 0.1% ammonium hydroxide, at flow rate of 60 mL/min) to give the desired product as a racemic mixture (10 mg, 30%). LCMS calculated for $C_{20}H_{16}ClFN_7$ (M+H)$^+$: m/z=408.1. found: 408.0. $^1$H NMR (300 MHz, DMSO-$d_6$): δ 8.09 (m, 3H), 8.65 (m, 3H), 7.42 (m, 4H), 5.02 (br s, 1H), 3.30 (m, 1H), 1.42 (m, 3H).

The racemic mixture was separated on a ChiralPak IA column (20×250 mm, 5 μm particle size), column loading=2.5 mg/mL, using 5% ethanol in hexanes at 15 mL/min. to give isomer 1 (rt=32.0 min) and isomer 2 (rt=46.5 min).

Example 2

N-{1-[8-Chloro-5-(3-fluorophenyl)-3-methylimidazo pyridin-6-yl]ethyl}-9H-purin-6-amine

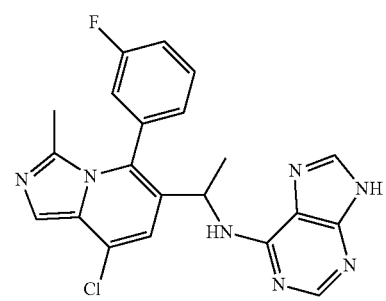 [SMILES: Cc1ncc2c(Cl)cc(C(C)Nc3ncnc4[nH]cnc34)c(-c3cccc(F)c3)n12]

Step A: Methyl 6-[(acetylamino)methyl]-5-chloro-2-(3-fluorophenyl)nicotinate

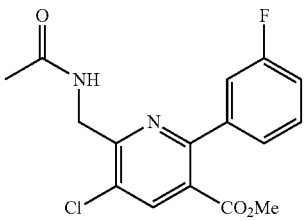 [SMILES: COC(=O)c1cc(Cl)c(CNC(C)=O)nc1-c1cccc(F)c1]

Methyl 6-(aminomethyl)-5-chloro-2-(3-fluorophenyl)nicotinate (0.35 g, 1,2 mmol) was stirred in N,N-dimethylformamide (5 mL) with N,N-diisopropylethylamine (0.41 mL, 2.4 mmol) and acetic anhydride (0.17 mL, 1.8 mmol) was added. The mixture was stirred for 30 minutes at room temperature. Evaporation gave the crude material which was contaminated with the corresponding dechlorinated byproduct (0.4 g, 100%). LCMS calculated for $C_{16}H_{15}ClFN_2O_3$ $(M+H)^+$: m/z=337.1. found 336.9.

Step B: N-{1-[8-Chloro-5-(3-fluorophenyl)-3-methylimidazo[1,5-a]pyridin-6-yl]ethyl}-9H-purin-6-amine

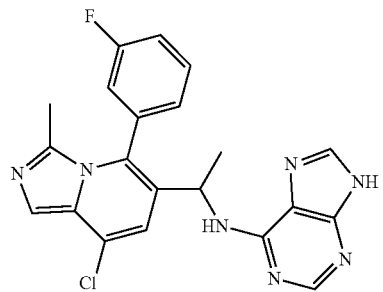 [SMILES: Cc1ncc2c(Cl)cc(C(C)Nc3ncnc4[nH]cnc34)c(-c3cccc(F)c3)n12]

The desired compound was prepared by procedures analogous to those of Example 1, steps G-L, using methyl 6-[(acetylamino)methyl]-5-chloro-2-(3-fluorophenyl)nicotinate as the starting material to give a racemic mixture of atrope isomers. LCMS calculated for $C_{21}H_{18}ClFN_7$ $(M+H)^+$: m/z=422.1. found: 421.9. $^1$H NMR (300 MHz, DMSO-$d_6$): δ 8.09 (m, 3H), 7.58 (m, 3H), 7.39 (m, 3H), 4.83 (br s, 1H), 3.30 (br s, 1H), 1.80 (m, 3H), 1.42 (m, 3H).

Example 3

N-{1-[8-Chloro-5-(3-fluorophenyl)imidazo[1,2-a]pyridin-6-yl]ethyl}-9H-purin-6-amine

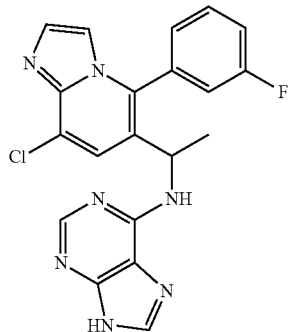 [SMILES: CC(Nc1ncnc2[nH]cnc12)c1cc(Cl)c2nccn2c1-c1cccc(F)c1]

Step A: Methyl 5,6-dichloro-2-(3-fluorophenyl)nicotinate

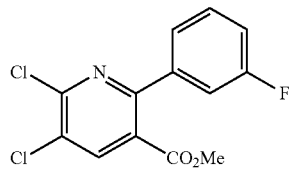

Methyl 5-chloro-2-(3-fluorophenyl)nicotinate 1-oxide (3.0 g, 11 mmol) was stirred in phosphoryl chloride (30 mL) and heated at 90° C. for 1 hour. Evaporation and purification by flash column chromatography using ethyl acetate in hexanes (0-20%) gave the desired compound (2.4 g, 75%). LCMS calculated for $C_{13}H_9Cl_2FNO_2$ $(M+H)^+$: m/z=300.0, 302.0. found: 299.8, 301.8. $^1$H NMR (300 MHz, CDCl$_3$): δ 8.23 (s, 1H), 7.40 (m, 2H), 7.22 (m, 1H), 7.17 (m, 1H), 3.73 (s, 3H).

Step B: Methyl 5-chloro-6-[(3,4-dimethoxybenzyl)amino]-2-(3-fluorophenyl)nicotinate

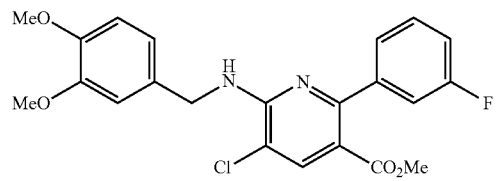 [SMILES: COC(=O)c1cc(Cl)c(NCc2ccc(OC)c(OC)c2)nc1-c1cccc(F)c1]

A solution of methyl 5,6-dichloro-2-(3-fluorophenyl)nicotinate (55 mg, 0.18 mmol) in ethanol (1 mL, 20 mmol) was treated with veratrylamine (82 µL, 0.55 mmol) and refluxed for 30 minutes. The reaction mixture was concentrated and purified by flash column chromatography using ethyl acetate in hexanes (0-30%) to give the desired product (64 mg, 81%). LCMS calculated for $C_{22}H_{21}ClFN_2O_4$ $(M+H)^+$: m/z=431.1. found: 430.9.

Step C: Methyl 6-amino-5-chloro-2-(3-fluorophenyl)nicotinate

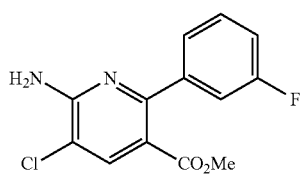 [SMILES: COC(=O)c1cc(Cl)c(N)nc1-c1cccc(F)c1]

A solution of methyl 5-chloro-6-[(3,4-dimethoxybenzyl)amino]-2-(3-fluorophenyl)nicotinate (0.11 g, 0.26 mmol) in trifluoroacetic acid (4 mL, 50 mmol) was heated at 60° C. for 22 hours. The reaction mixture was concentrated, diluted with methanol, and filtered. The filtrate was concentrated and purified via RP-HPLC (XBridge C18 column, eluting with a gradient of acetonitrile/water containing 0.1% ammonium hydroxide, at flow rate of 60 mL/min) to give the desired product (56 mg, 75%). LCMS calculated for $C_{13}H_{11}ClFN_2O_2$ $(M+H)^+$: m/z=281.0. found: 280.8.

Step D: Methyl 8-chloro-5-(3-fluorophenyl)imidazo[1,2-a]pyridine-6-carboxylate

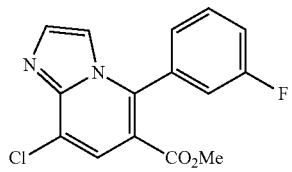 [SMILES: COC(=O)c1cc(Cl)c2nccn2c1-c1cccc(F)c1]

A solution of methyl 6-amino-5-chloro-2-(3-fluorophenyl)nicotinate (0.19 g, 0.66 mmol) in ethanol (4 mL) at 60° C. was treated with 50 wt % chloroactaldehyde in water (0.34 mL, 2.6 mmol) dropwise. The reaction mixture was stirred at reflux for 2 hours. The reaction mixture was concentrated and purified by flash column chromatography with ethyl acetate in hexanes (0-60%) to give the desired product (180 mg, 87%). LCMS calculated for $C_{15}H_{11}ClFN_2O_2$ (M+H)$^+$: m/z=305.0. found: 304.8.

Step E: 8-Chloro-5-(3-fluorophenyl)imidazo[1,2-a]pyridine-6-carboxylic acid

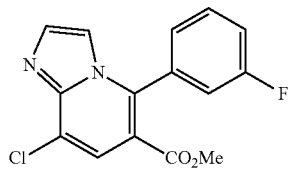 [SMILES: COC(=O)c1cc(Cl)c2nccn2c1-c1cccc(F)c1]

A solution of methyl 8-chloro-5-(3-fluorophenyl)imidazo[1,2-a]pyridine-6-carboxylate (0.18 g, 0.57 mmol) in tetrahydrofuran (3 mL) was treated with 1 M sodium hydroxide in water (1.7 mL, 1.7 mmol) and stirred at 20° C. for 6 hours. The reaction mixture was concentrated, diluted with water, cooled to 0° C., and treated with 1 M hydrogen chloride in water (2.3 mL, 2.3 mmol) dropwise. The resultant suspension was filtered to give the desired product (0.17 g, quantitative) that was used without further purification. LCMS calculated for $C_{14}H_9ClFN_2O_2$ (M+H)$^+$: m/z=291.0. found: 290.9.

Step F: 8-Chloro-5-(3-fluorophenyl)-N-methoxy-N-methylimidazo[1,2-a]pyridine-6-carboxamide trifluoroacetate

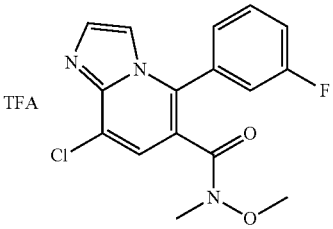 [SMILES: CON(C)C(=O)c1cc(Cl)c2nccn2c1-c1cccc(F)c1]

The desired compound was prepared according to the procedure of Example 1, step 1, using 8-chloro-5-(3-fluorophenyl)imidazo[1,2-a]pyridine-6-carboxylic acid as the starting material in 79% yield after purification on RP-HPLC (XBridge C18 column, eluting with a gradient of acetonitrile/water containing 0.05% TFA, at flow rate of 60 mL/min) to give the desired product as a TFA salt. $C_{16}H_{14}ClFN_3O_2$ (M+H)$^+$: m/z=334.1. found: 333.9.

Step G: 1-[8-Chloro-5-(3-fluorophenyl)imidazo[1,2-a]pyridin-6-yl]ethanone

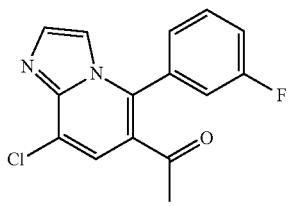 [SMILES: CC(=O)c1cc(Cl)c2nccn2c1-c1cccc(F)c1]

The desired compound was prepared according to the procedure of Example 1, step J, using 8-chloro-5-(3-fluorophenyl)-N-methoxy-N-methylimidazo[1,2-a]pyridine-6-carboxamide trifluoroacetate as the starting material in 50% yield. $C_{15}H_{11}ClFN_2O$ (M+H)$^+$: m/z=289.1. found: 288.9.

Step H: 1-[8-Chloro-5-(3-fluorophenyl)imidazo[1,2-a]pyridin-6-yl]ethanamine

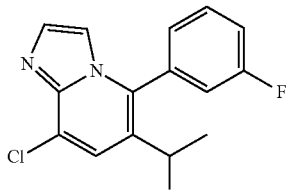

The desired compound was prepared according to the procedure of Example 1, step K, using 1-[8-chloro-5-(3-fluorophenyl)imidazo[1,2-a]pyridin-6-yl]ethanone as the starting material in 38% yield. $C_{15}H_{14}ClFN_3$ (M+H)$^+$: m/z=290.1. found: 290.1.

Step I: N-{1-[8-Chloro-5-(3-fluorophenyl)imidazol-[1,2-a]pyridin-6-yl]ethyl}-9H-purin-6-amine

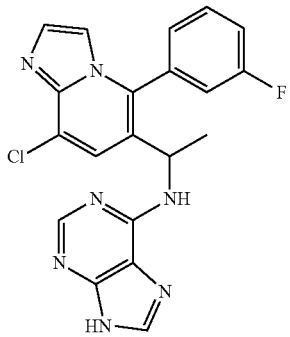 [SMILES: CC(Nc1ncnc2[nH]cnc12)c1cc(Cl)c2nccn2c1-c1cccc(F)c1]

The desired compound was prepared according to the procedure of Example 1, step L, using 1-[8-chloro-5-(3-fluorophenyl)imidazo[1,2-a]pyridin-6-yl]ethanamine as the starting material in 35% yield. $C_{20}H_{16}ClFN_7$ $(M+H)^+$: m/z=408.1. found: 408.1. $^1H$ NMR (300 MHz, DMSO-$d_6$): δ 12.92 (br s, 1H), 8.23 (br s, 1H), 8.10-8.03 (m, 2H), 7.91 (d, J=6.2 Hz, 1H), 7.75-7.64 (m, 2H), 7.52-7.38 (m, 3H), 7.21 (d, J=7.0 Hz, 1H), 4.10-4.07 (m, 1H), 1.47-1.43 (m, 3H).

Example 4

N-{1-[5-(4-Acetylpiperazin-1-yl)-8-chloroimidazo[1,5-a]pyridin-6-yl]ethyl}-9H-purin-6-amine

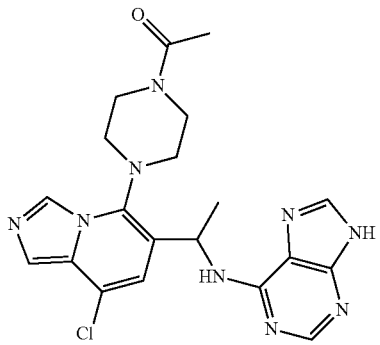 [SMILES: CC(=O)N1CCN(c2c(C(C)Nc3ncnc4[nH]cnc34)cc(Cl)c3cncn23)CC1]

Step A: Methyl 2,5-dichloronicotinate 1-oxide

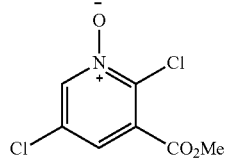 [SMILES: COC(=O)c1cc(Cl)c[n+]([O-])c1Cl]

A solution of methyl 2,5-dichloronicotinate (15 g, 73 mmol), trifluoroacetic acid (91 mL) and 30% aqueous hydrogen peroxide solution (15 mL) were stirred and heated at 70° C. for 1 hour. Evaporation and purification by flash column chromatography using ethyl acetate in hexanes (0-100%) gave the desired product (16 g, 99%). LCMS calculated for $C_7H_6Cl_2NO_3$ $(M+H)^+$: m/z=222.0. found: 221.8.

Step B: Methyl 2,5-dichloro-6-cyanonicotinate

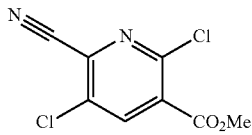

Methyl 2,5-dichloronicotinate 1-oxide (16 g, 72 mmol) was dissolved in acetonitrile (200 mL) with triethylamine (15 mL, 110 mmol) and trimethylsilyl cyanide (24 mL, 180 mmol) was added. The mixture was heated to 70° C. for 30 minutes. Evaporation and purification on silica gel using ethyl acetate in hexanes (0-30%) gave the desired compound (14 g, 82%). LCMS calculated for $C_8H_5Cl_2N_2O_2$ $(M+H)^+$: m/z=231.0. found: 230.8.

Step C: tert-Butyl 4-[5-chloro-6-cyano-3-(methoxycarbonyl)pyridin-2-yl]piperazine-1-carboxylate

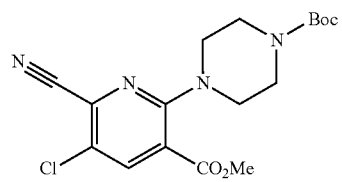

A stirred mixture of methyl 2,5-dichloro-6-nicotinate (3.5 g, 15 mmol), tert-butylpiperazine-1-carboxylate (3.4 g, 18 mmol) and cesium carbonate (14 g, 42 mmol) was heated to 70° C. for 1 hour. The mixture was quenched with water and extracted with ethyl acetate. The extracts were washed with brine and dried over sodium sulfate. Evaporation and purification on silica gel using ethyl acetate in hexanes (0-100%) gave the desired compound (5.1 g, 88%). LCMS calculated for $C_{17}H_{22}ClN_4O_4$ $(M+H)^+$: m/z=381.1. found: 380.9.

Step D: tert-Butyl 4-[6-aminomethyl)-3-(methoxycarbonyl)pyridin-2-yl]piperazine-1-carboxylate hydrochloride

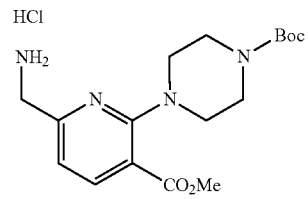

tert-Butyl 4-[5-chloro-6-cyano-3-(methoxycarbonyl)pyridin-2-yl]piperazine-1-carboxylate (8.0 g, 21 μmol) was stirred in methanol (130 mL) and a mixture of 10% palladium on carbon (4.47 g, 0.0021 mol, wet, Degussa) was added. The mixture was degassed 3 times and placed on a Parr shaker overnight. The mixture was filtered through celite. The filtrates were evaporated to give the desired compound (8.0 g, 98%). LCMS calculated for $C_{17}H_{27}N_4O_4$ $(M+H)^+$: m/z=351.2. found: 350.9.

Step E: tert-Butyl 4-{6-[(formylamino)methyl]-3-(methoxycarbonyl)pyridin-2-yl}piperazine-1-carboxylate

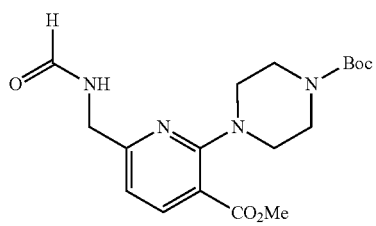 [SMILES: COC(=O)c1ccc(CNC=O)nc1N1CCN(C(=O)OC(C)(C)C)CC1]

Formic acid (2.2 mL, 58 mmol) and acetic anhydride (5.2 mL, 58 mmol) were stirred at room temperature for 1 hour. The mixture was added dropwise to a solution of tert-butyl 4-[6-(aminomethyl)-3-(methoxycarbonyl)pyridin-2-yl]piperazine-1-carboxylate hydrochloride (4.9 g, 13 mmol) in methylene chloride (90 mL) at 0° C. and stirred for 48 hours. Evaporation gave the crude material which was treated with sodium bicarbonate and extracted with methylene chloride to give the desired compound (4.9 g, 100%). LCMS calculated for $C_{18}H_{27}N_4O_5$ $(M+H)^+$: m/z=379.2. found: 378.9.

Step F: tert-Butyl 4-{5-chloro-6-[(formylamino)methyl]-3-(methoxycarbonyl)pyridin-2-yl}piperazine-1-carboxylate

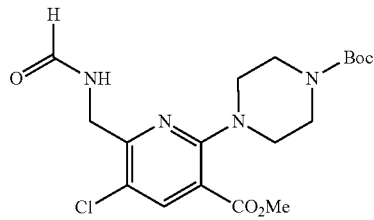 [SMILES: COC(=O)c1cc(Cl)c(CNC=O)nc1N1CCN(C(=O)OC(C)(C)C)CC1]

tert-Butyl 4-{6-[(formylamino)methyl]-3-(methoxycarbonyl)pyridin-2-yl}piperazine-1-carboxylate (4.85 g, 0.0128 mol) and N-chlorosuccinimide (2.1 g, 15 mmol) was stirred in tetrahydrofuran (85 mL) at 50° C. for 16 hours. Evaporation and purification on silica gel using ethyl acetate in hexanes (0-80%) gave the desired compound (5.6 g, 100%). LCMS calculated for $C_{18}H_{26}ClN_4O_5$ $(M+H)^+$: m/z=413.2. found: 412.9.

Step G: Methyl 8-chloro-5-piperazin-1-ylimidazo[1,5-a]pyridine-6-carboxylate hydrochloride

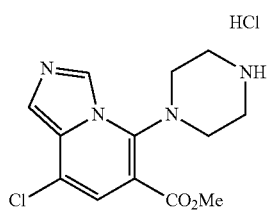 [SMILES: Cl ; COC(=O)c1cc(Cl)c2cncn2c1N1CCNCC1]

A solution of tert-butyl 4-{5-chloro-6-[(formylamino)methyl]-3-(methoxycarbonyl)pyridin-2-yl}piperazine-1-carboxylate (670 mg, 2.2 mmol) in phosphoryl chloride (5.0 mL, 54 mmol) was heated to 70° C. for 30 minutes. Evaporation gave the desired compound (700 mg, 98%). LCMS calculated for $C_{13}H_{16}ClN_4O_2$ $(M+H)^+$: m/z=295.1. found: 294.9.

Step H: Methyl 5-[4-(tert-butoxycarbonyl)piperazin-1-yl]-8-chloroimidazo[1,5-a]pyridine-6-carboxylate

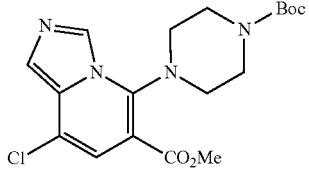 [SMILES: COC(=O)c1cc(Cl)c2cncn2c1N1CCN(C(=O)OC(C)(C)C)CC1]

Into the reaction was added methyl 8-chloro-5-piperazin-1-ylimidazo[1,5-a]pyridine-6-carboxylate hydrochloride (700 mg, 2.1 mmol), sodium hydrogenecarbonate (940 mg, 11 mmol), water (14 mL, 780 mmol) and tetrahydrofuran (9.4 mL). The reaction mixture was foamy and after all the bubbling ceased, di-tert-butyldicarbonate (1.4 g, 6.3 mmol) was added and the mixture was stirred at room temperature overnight. The mixture was concentrated, extracted with ethyl acetate, dried over $Na_2SO_4$ and evaporated. Purification on silica gel using ethyl acetate in hexanes (0-100%) gave the desired compound (202 mg, 24%). LCMS calculated for $C_{18}H_{24}ClN_4O_4$ $(M+H)^+$: m/z=395.1. found: 394.9.

Step I: 5-[4-(tert-Butoxycarbonyl)piperazin-1-yl]-8-chloroimidazo[1,5-a]pyridine-6-carboxylic acid

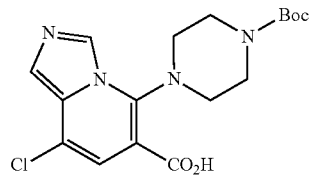 [SMILES: CC(C)(C)OC(=O)N1CCN(c2c(C(=O)O)cc(Cl)c3cncn23)CC1]

Methyl 5-[4-(tert-butoxycarbonyl)piperazin-1-yl]-8-chloroimidazo[1,5-a]pyridine-6-carboxylate (120 mg, 0.3123 mmol) was stirred in methanol (2 mL) and 3.0 M sodium hydroxide in water (0.4 mL, 1.0 mmol) was added. The mixture was stirred at room temperature overnight. Acidification with a few drops of 1 M HCl (checked with litmus paper pH 6), evaporation and trituration with water gave the desired compound (94 mg, 79%). LCMS calculated for $C_{17}H_{22}ClN_4O_4$ $(M+H)^+$: m/z=381.1. found: 380.9.

Step J: tert-Butyl 4-(8-chloro-6-{[methoxy(methyl)amino]carbonyl}imidazol-[1,5-a]pyridin-5-yl)piperazine-1-carboxylate

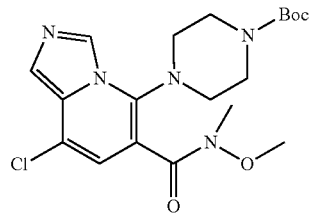 [SMILES: CON(C)C(=O)c1cc(Cl)c2cncn2c1N1CCN(C(=O)OC(C)(C)C)CC1]

Into a flask was placed a suspension of 5-[4-(tert-butoxycarbonyl)piperazin-1-yl]-8-chloroimidazo[1,5-a]pyridine-6-carboxylic acid (38 mg, 0.10 mmol) in anhydrous N,N-dimethylformamide (0.28 mL, 3.6 mmol) under $N_2$. N,N-diisopropylethylamine (87 μL, 0.50 mmol) was added followed by the N,O-dimethylhydroxylamine hydrochloride (29 mg, 0.30 mmol) and 0.6 M 1-hydroxy-7-azabenzotriazole in N,N-dimethylformamide (33 μL, 0.020 mmol). Lastly, the N-(3-dimethylaminopropyl)-N-ethylcarbodiimide hydrochloride (29 mg, 0.15 mmol) was added. The precipitate slowly dissolved, and the resulting solution was stirred for 4.5 hours. The reaction was quenched with water and extracted into ethyl acetate, washed with brine, dried ($Na_2SO_4$), and evaporated to dryness. The crude product was flashed on silica gel (Isco, 4 g column, 0-100% ethyl acetate/hexane) to afford the pure product (31 mg, 73%). LCMS calculated for $C_{19}H_{27}ClN_5O_4$ (M+H)$^+$: m/z=424.2. found: 423.9.

Step K: tert-Butyl 4-(6-acetyl-8-chloroimidazo[1,5-a]pyridin-5-yl)piperazine-1-carboxylate

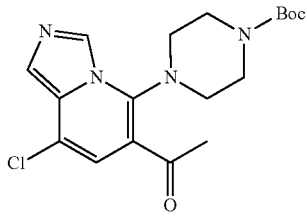 [SMILES: CC(=O)c1cc(Cl)c2cncn2c1N1CCN(C(=O)OC(C)(C)C)CC1]

Into a microwave vial was placed a solution of tert-butyl 4-(8-chloro-6-{[methoxy(methyl)amino]carbonyl}imidazo[1,5-a]pyridin-5-yl)piperazine-1-carboxylate (31 mg, 0.073 mmol) in anhydrous tetrahydrofuran (0.5 mL) under $N_2$ at 0° C. A solution of 3.0 M methylmagnesium chloride in tetrahydrofuran (85 μL, 0.26 mmol) was added dropwise. The solution was stirred at 0° C. for 30 minutes. It was stirred for 2 hours at room temperature. The reaction solution was quenched at 0° C. with 1.0 M hydrogen chloride in water (0.5 mL, 0.5 mmol), poured into 25 mL of saturated $NaHCO_3$ solution and was extracted into ethyl acetate. The ethyl acetate extract was washed with brine, dried over anhydrous $Na_2SO_4$, filtered, and evaporated to give the crude which was purified on silica gel with ethyl acetate (0-60%) to give desired product (22 mg, 78%). LCMS calculated for $C_{18}H_{24}ClN_4O_3$ (M+H)$^+$: m/z=379.2. found: 378.9.

Step L: 1-(8-Chloro-5-piperazin-1-ylimidazo[1,5-a]pyridin-6-yl)ethanone hydrochloride

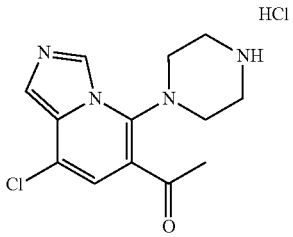 [SMILES: Cl ; CC(=O)c1cc(Cl)c2cncn2c1N1CCNCC1]

tert-Butyl 4-(6-acetyl-8-chloroimidazo[1,5-a]pyridin-5-yl)piperazine-1-carboxylate (19 mg, 0.051 mmol) was taken into a vial and 4.0 M hydrogen chloride in 1,4-dioxane (1.0 mL, 4.0 mmol) was added and was stirred for 15 minutes. The solvents were evaporated to give the desired compound (16 mg, quantitative). LCMS calculated for $C_{13}H_{16}ClN_4O$ (M+H)$^+$: m/z=279.1. found: 278.9.

Step M: 1-[5-(4-Acetylpiperazin-1-yl)-8-chloroimidazo[1,5-a]pyridin-6-yl]ethanone

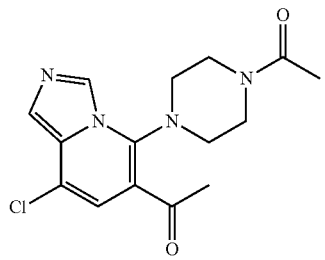 [SMILES: CC(=O)c1cc(Cl)c2cncn2c1N1CCN(C(C)=O)CC1]

1-(8-Chloro-5-piperazin-1-ylimidazo[1,5-a]pyridin-6-yl)ethanone hydrochloride was dissolved in methylene chloride (1.0 mL) and N,N-diisopropylethylamine (45 μL, 0.26 mmol) was added. To the reaction mixture, acetyl chloride (5.5 μL, 0.077 mmol) was added and the mixture was stirred for 5 minutes. Evaporation and purification by preparative LCMS (pH 10) gave the desired compound (13 mg, 77%). LCMS calculated for $C_{15}H_{18}ClN_4O_2$ (M+H)$^+$: m/z=321.1. found: 320.9.

Step N: 1-[5-(4-Acetylpiperazin-1-yl)-8-chloroimidazo[1,5-a]-pyridin-6-yl]ethanamine

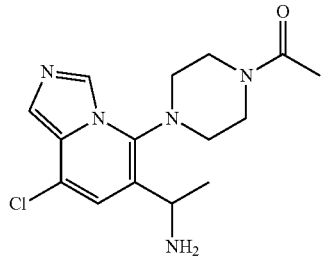 [SMILES: CC(=O)N1CCN(c2c(C(C)N)cc(Cl)c3cncn23)CC1]

A mixture of 1-[5-(4-acetylpiperazin-1-yl)-8-chloroimidazo[1,5-a]pyridin-6-yl]ethanone (12.6 mg, 0.0393 mmol) (10010-158P) and ammonium acetate (30.3 mg, 0.393 mmol) in methanol (0.4 mL) and acetonitrile (0.4 mL) was heated at 65° C. in a sealed vial for 1 hour. The mixture was cooled to room temperature and sodium cyanoborohydride (7.40 mg, 0.118 mmol) was added. The reaction was heated at 65° C. overnight. The mixture was diluted with methanol and purified on preparative LCMS using pH 10 buffer to give the desired compound (11 mg, 89%). LCMS calculated for $C_{15}H_{21}ClN_5O$ (M+H)$^+$: m/z=322.1. found: 321.9.

Step O: N-{1-[5-(4-Acetylpiperazin-1-yl)-8-chloroimidazo[1,5-a]-pyridin-6-yl]ethyl}-9H-purin-6-amine A mixture of 1-[5-(4-acetylpiperazin-1-yl)-8-chloroimidazo[1,5-a]pyridin-6-yl]ethanamine (11.2 mg, 0.035 mmol), 6-bromo-9H-purine (14 mg, 0.070 mmol) and IV, N-diisopropylethylamine (18 μL, 0.10 mmol) in ethanol (0.93 mL) was heated to 110° C. overnight. Purification by preparative LCMS (pH 10) gave the desired compound (6.7 mg, 44%). LCMS calculated for $C_{20}H_{23}ClN_9O$ (M+H)$^+$: m/z=440.2. found: 439.9. $^1$H NMR (300 MHz, DMSO-d$_6$): δ 8.52 (s, 1H), 8.17 (m, 3H), 7.42 (s, 1H), 7.37 (s, 1H), 5.90 (s, 1H), 3.80 (m, 2H), 3.65 (m, 2H), 3.50 (m, 1H), 3.40 (m, 2H), 3.20 (m, 2H), 2.09 (s, 3H), 1.52, (m, 3H).

(300 MHz, DMSO-d$_6$): δ 8.52 (s, 1H), 8.17 (m, 3H), 7.42 (s, 1H), 7.37 (s, 1H), 5.87 (s, 1H), 3.68 (m, 2H), 3.57 (m, 3H), 3.42 (m, 2H), 3.19 (m, 2H), 1.53 (m, 3H), 1.42, (s, 9H).

Example 5

N-(1-{8-chloro-5-[4-(methylsulfonyl)piperazin-1-yl]imidazo pyridin-6-yl}ethyl)-9H-purin-6-amine

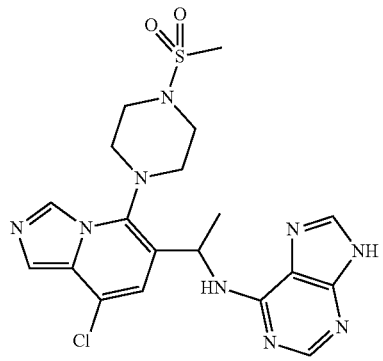 [SMILES: CC(Nc1ncnc2[nH]cnc12)c1cc(Cl)c2cncn2c1N1CCN(S(C)(=O)=O)CC1]

The desired compound was prepared according to the procedure of Example 4, steps M-O, using methanesulfonyl chloride and 1-(8-chloro-5-piperazin-1-ylimidazo[1,5-a]pyridin-6-yl)ethanone hydrochloride as the starting material. LCMS calculated for $C_{19}H_{23}ClN_9O_2S$ (M+H)$^+$: m/z=476.1. found: 476.0. $^1$H NMR (300 MHz, DMSO-d$_6$): δ 8.58 (s, 1H), 8.20 (s, 1H), 8.11 (m, 2H), 7.42 (s, 1H), 7.38 (s, 1H), 5.83 (s, 1H), 3.71 (m, 1H), 3.41 (m, 4H), 3.33 (m, 4H), 2.99 (s, 3H), 1.51 (m, 3H).

Example 6 tert-Butyl 4-{8-chloro-6-[1-(9H-purin-6-ylamino)ethyl]imidazo[1,5-a]pyridin-5-yl}piperazine-1-carboxylate

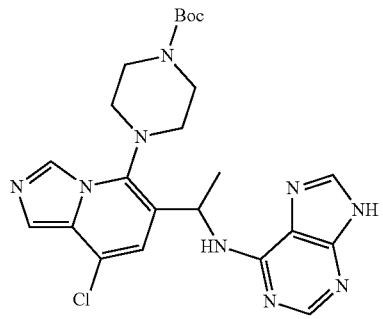 [SMILES: CC(Nc1ncnc2[nH]cnc12)c1cc(Cl)c2cncn2c1N1CCN(C(=O)OC(C)(C)C)CC1]

The desired compound was prepared according to the procedure of Example 4, steps N-O, using tert-butyl 4-(6-acetyl-8-chloroimidazo[1,5-a]pyridin-5-yl)piperazine-1-carboxylate as the starting material. LCMS calculated for $C_{23}H_{29}ClN_9O_2$ (M+H)$^+$: m/z=498.2. found: 497.9. $^1$H NMR

Example 7

N-(1-{8-Chloro-5-[4-(cyclopropylcarbonyl)piperazin-1-yl]imidazo[1,5-a]pyridin-6-yl}ethyl)-9H-purin-6-amine

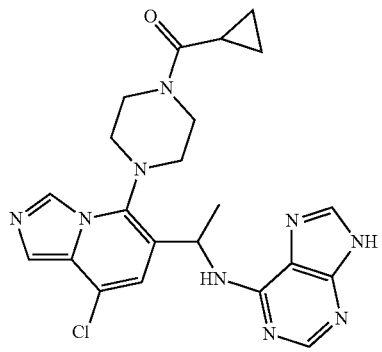 [SMILES: CC(Nc1ncnc2[nH]cnc12)c1cc(Cl)c2cncn2c1N1CCN(C(=O)C2CC2)CC1]

The desired compound was prepared according to the procedure of Example 4, steps M-O, using cyclopropanecarbonyl chloride and 1-(8-chloro-5-piperazin-1-ylimidazo[1,5-a]pyridin-6-yl)ethanone hydrochloride as the starting material. LCMS calculated for $C_{22}H_{25}ClN_9O$ (M+H)$^+$: m/z=466.2. found: 465.9. $^1$H NMR (300 MHz, DMSO-d$_6$): δ 8.57 (s, 1H), 8.17 (m, 3H), 7.42 (s, 1H), 7.37 (s, 1H), 5.89 (s, 1H), 4.03 (m, 2H), 3.40-3.90 (m, 5H), 3.19 (m, 2H), 2.03 (m, 1H), 1.53 (m, 3H), 1.42, (s, 9H), 0.78 (m, 4H).

Example 8

N-(1-{8-chloro-5-[4-(methoxyacetyl)piperazin-1-yl]imidazo[1,5-a]pyridin-6-yl}ethyl)-9H-purin-6-amine

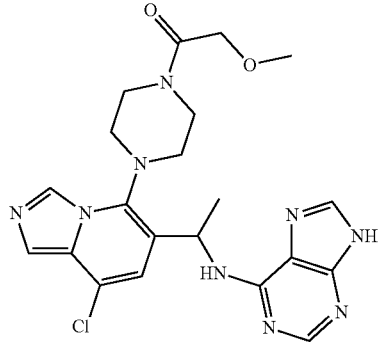 [SMILES: COCC(=O)N1CCN(c2c(C(C)Nc3ncnc4[nH]cnc34)cc(Cl)c3cncn23)CC1]

The desired compound was prepared according to the procedure of Example 4, steps M-O, using methoxyacetyl chloride and 1-(8-chloro-5-piperazin-1-ylimidazo[1,5-a]pyridin-6-yl)ethanone hydrochloride as the starting material. LCMS calculated for $C_{21}H_{25}ClN_9O_2$ (M+H)$^+$: m/z=470.2. found: 469.9. $^1$H NMR (300 MHz, DMSO-d$_6$): δ 8.53 (s, 1H), 8.20 (s, 1H), 8.11 (m, 2H), 7.42 (s, 1H), 7.38 (s, 1H), 5.83 (s, 1H), 4.18 (m, 2H), 3.80 (m, 4H), 3.33 (m, 5H), 3.31 (s, 3H), 1.51 (m, 3H).

Example 9

N-[1-(8-Chloro-5-piperazin-1-ylimidazo[1,5-a]pyridin-6-yl)ethyl]-9H-purin-6-amine dihydrochloride

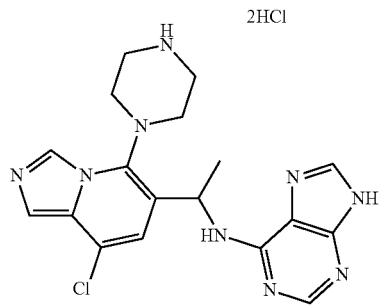 [SMILES: CC(Nc1ncnc2[nH]cnc12)c1cc(Cl)c2cncn2c1N1CCNCC1]

To tert-butyl 4-{8-chloro-6-[1-(9H-purin-6-ylamino)ethyl]imidazo[1,5-a]pyridin-5-yl}piperazine-1-carboxylate (8.0 mg, 0.016 mmol) in methylene chloride (0.5 mL, 8 mmol), 4.0 M hydrogen chloride in 1,4-dioxane (1.0 mL, 4.0 mmol) was added. The mixture was stirred for 15 minutes. Evaporation gave the desired compound (7.5 mg, 99%). LCMS calculated for $C_{18}H_{21}ClN_9$ (M+H)$^+$: m/z=398.2. found: 397.9.

Example 10

3-(4-{8-Chloro-6-[1-(9H-purin-6-ylamino)ethyl]imidazo[1,5-a]pyridin-5-yl}piperazin-1-yl)-3-oxopropanenitrile

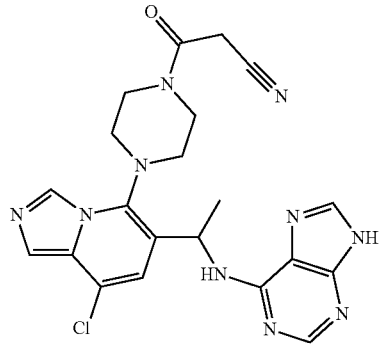 [SMILES: CC(Nc1ncnc2[nH]cnc12)c1cc(Cl)c2cncn2c1N1CCN(C(=O)CC#N)CC1]

Step A: 3-{4-[6-(1-Aminoethyl)-8-chloroimidazo[1,5-a]pyridine-5-yl]piperazin-1-yl}-3-oxopropanenitrile

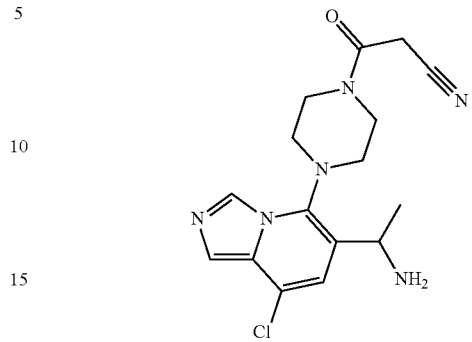

The desired compound was prepared according to the procedure of Example 4, steps M-N, using 3-[(2,5-dioxopyrrolidin-1-yl)oxy]-3-oxopropanenitrile and 1-(8-chloro-5-piperazin-1-ylimidazo[1,5-a]pyridin-6-yl)ethanone hydrochloride as the starting material. LCMS calculated for $C_{16}H_{20}ClN_6O$ (M+H)$^+$: m/z=347.1. found: 346.9.

Step B: 3-(4-{8-Chloro-6-[1-(9H-purin-6-ylamino)ethyl]imidazo[1,5-a]pyridin-5-yl}piperazin-1-yl)-3-oxopropanenitrile A mixture of 3-{4-[6-(1-aminoethyl)-8-chloroimidazo[1,5-a]pyridine-5-yl]piperazin-1-yl}-3-oxopropanenitrile (18 mg, 0.052 mmol), 6-bromo-9-(tetrahydro-2H-pyran-2-yl)-9H-purine (29 mg, 0.10 mmol) and N,N-diisopropylethylamine (27 μL, 0.16 mmol) in ethanol (1.0 mL) was heated at 110° C. overnight. The mixture was evaporated and a 4 M solution of hydrogen chloride in 1,4-dioxane (1.0 mL, 4.0 mmol) was added. The mixture was evaporated and a 4 M solution of hydrogen chloride in 1,4-dioxane (1.0 mL, 4.0 mmol) was added. The mixture was evaporated and purified by preparative LCMS (pH 10) to give the desired compound (8.6 mg, 36%). LCMS calculated for $C_{21}H_{22}ClN_{10}O$ (M+H)$^+$: m/z=465.2. found: 464.9.

Example 11

N-[1-(8-Chloro-5-{4-[(1-methyl-1H-pyrazol-4-yl)carbonyl]piperazin-1-yl}imidazo[1,5-a]pyridin-6-yl)ethyl]-9H-purin-6-amine

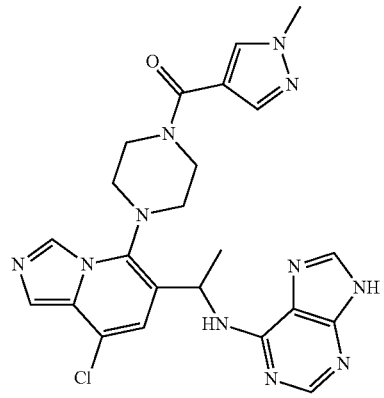 [SMILES: CC(Nc1ncnc2[nH]cnc12)c1cc(Cl)c2cncn2c1N1CCN(C(=O)c2cnn(C)c2)CC1]

71

The desired compound was prepared according to the procedure of Example 10, steps A-B, using 1-methyl-1H-pyrazole-4-carbonyl chloride and 1-(8-chloro-5-piperazin-1-ylimidazo[1,5-a]pyridin-6-yl)ethanone hydrochloride as the starting material. LCMS calculated for $C_{23}H_{25}ClN_{11}O$ $(M+H)^+$: m/z=506.2. found: 505.9.

Example 12

N-(1-{8-Chloro-5-[4-(2-methoxyethyl)piperazin-1-yl]imidazo[1,5-a]pyridin-6-yl}ethyl)-9H-purin-6-amine

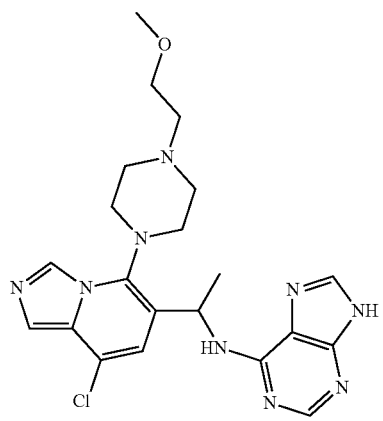 [SMILES: COCCN1CCN(c2c(C(C)Nc3ncnc4[nH]cnc34)cc(Cl)c3cncn23)CC1]

Step A: 1-{8-Chloro-5-[4-(2-methoxyethyl)piperazin-1-yl]imidazo[1,5-a]pyridin-6-yl}ethanone

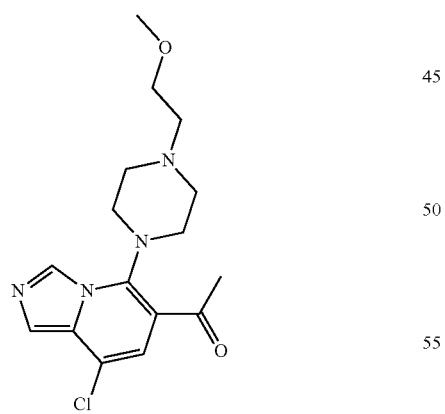

1-(8-Chloro-5-piperazin-1-ylimidazo[1,5-a]pyridine-6-yl)ethanone hydrochloride (16 mg, 0.052 mmol), N,N-diisopropylethylamine (27 µL, 0.16 mmol) and 1-bromo-2-methoxyethane (4.9 µL, 0.052 mmol) were stirred in acetonitrile (1.0 mL) for 22 hours at 65° C. Purification by preparative LCMS (pH 10) gave the desired compound (10 mg, 60%). LCMS calculated for $C_{16}H_{22}ClN_4O_2$ $(M+H)^+$: m/z=337.1. found: 336.9.

72

Step B: 1-{8-Chloro-5-[4-(2-methoxyethyl)piperazin-1-yl]imidazol-[1,5-a]pyridin-6-yl}ethanamine

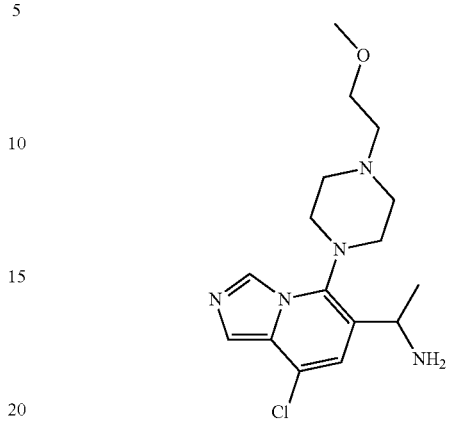

The desired compound was prepared according to the procedure of Example 4, step N, using 1-{8-chloro-5-[4-(2-methoxyethyl)piperazin-1-yl]imidazo[1,5-a]pyridin-6-yl}ethanone as the starting material in 40% yield. LCMS calculated for $C_{16}H_{25}ClN_5O$ $(M+H)^+$: m/z=338.2. found: 337.9.

Step C: N-(1-{8-Chloro-5-[4-(2-methoxyethyl)piperazin-1-yl]imidazo[1,5-a]pyridin-6-yl}ethyl)-9H-purin-6-amine The desired compound was prepared according to the procedure of Example 10, step B, 1-{8-chloro-5-[4-(2-methoxyethyl)piperazin-1-yl]imidazo[1,5-a]pyridin-6-yl}ethanamine as the starting material in 32% yield. LCMS calculated for $C_{21}H_{27}ClN_9O$ $(M+H)^+$: m/z=456.2. found: 455.9.

Example 13

(4-{8-Chloro-6-[1-(9H-purin-6-ylamino)ethyl]imidazo[1,5-a]pyridin-5-yl}piperazin-1-yl)acetonitrile

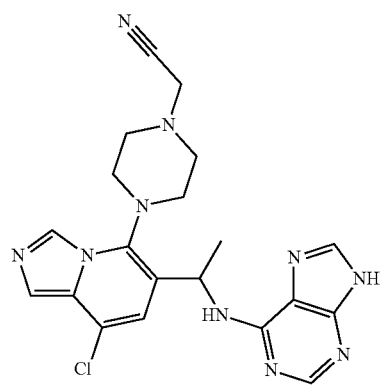 [SMILES: CC(Nc1ncnc2[nH]cnc12)c1cc(Cl)c2cncn2c1N1CCN(CC#N)CC1]

The desired compound was prepared according to the procedure of Example 12, steps A-C, using bromoacetonitrile as the starting material. LCMS calculated for $C_{20}H_{22}ClN_{10}$ (M+H)$^+$: m/z=437.2. found: 436.9.

Example 14

N-(1-{8-Chloro-5-[4-(4,4,4-trifluorobutyl)piperazin-1-yl]imidazo[1,5-a]pyridin-6-yl}ethyl)-9H-purin-6-amine

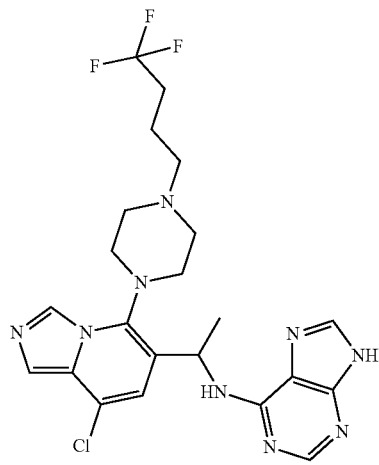 [SMILES: CC(Nc1ncnc2[nH]cnc12)c1cc(Cl)c2cncn2c1N1CCN(CCCC(F)(F)F)CC1]

The desired compound was prepared according to the procedure of Example 12, steps A-C, using 4-bromo-1,1,1-trifluorobutane as the starting material. LCMS calculated for $C_{22}H_{26}ClF_3N_9$ (M+H)$^+$: m/z=508.2. found: 507.9.

Example 15

N-{1-[8-Chloro-5-(4-cyclobutylpiperazin-1-yl)imidazo[1,5-a]pyridin-6-yl]ethyl}-9H-purin-6-amine

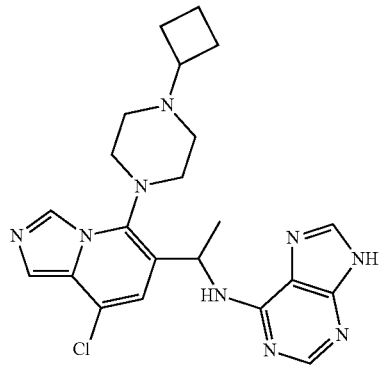 [SMILES: CC(Nc1ncnc2[nH]cnc12)c1cc(Cl)c2cncn2c1N1CCN(C2CCC2)CC1]

Step A. 1-[8-Chloro-5 (4-cyclobutylpiperazin-1-yl) imidazo[1,5-a]pyridine-6-yl]ethanone

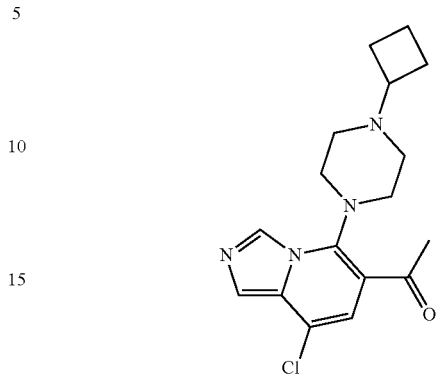

tert-Butyl 4-(6-acetyl-8-chloroimidazo[1,5-a]pyridine-5-yl)piperazine-1-carboxylate (33 mg, 0.087 mmol) was treated with a solution of 4 M hydrogen chloride in 1,4-dioxane (1.0 mL) and evaporated to dryness. Cyclobutanone (13 μL, 0.18 mmol), tetrahydrofuran (0.5 mL) and acetonitrile (0.5 mL) were added and the mixture was stirred for 30 minutes. Sodium cyanoborohydride (17 mg, 0.26 mmol) was added and was stirred for 4 hours. Purification by preparative LCMS (pH 10) gave the desired compound (18 mg, 61%). LCMS calculated for $C_{17}H_{22}ClN_4O$ (M+H)$^+$: m/z=333.1. found: 332.9.

Step B: 1-[8-Chloro-5(4-cyclobutylpiperazin-1-yl) imidazo[1,5-a]pyridine-6-yl]ethanamine

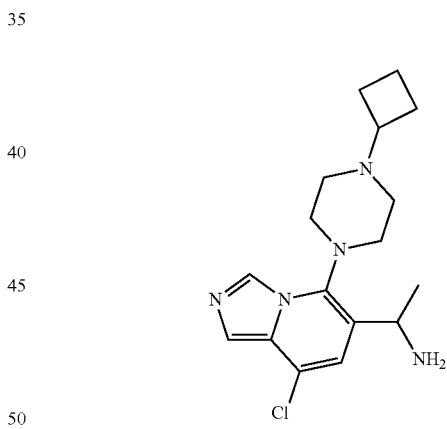

The desired compound was prepared according to the procedure of Example 4, step N, using 1-[8-chloro-5(4-cyclobutylpiperazin-1-yl)imidazo[1,5-a]pyridine-6-yl]ethanone as the starting material in 37% yield. LCMS calculated for $C_{17}H_{25}ClN_5$ (M+H)$^+$: m/z=334.2. found: 333.9.

Step C: N-{1-[8-Chloro-5-(4-cyclobutylpiperazin-1-yl)imidazo[1,5-a]-pyridin-6-yl]ethyl}-9H-purin-6-amine The desired compound was prepared according to the procedure of Example 10, step B, using 1-[8-chloro-5(4-cyclobutylpiperazin-1-yl)imidazo[1,5-a]pyridine-6-yl]ethanamine as the starting material in 45% yield. LCMS calculated for $C_{22}H_{27}ClN_9$ (M+H)$^+$: m/z=452.2. found: 451.9.

Example 16

N-(1-{8-Chloro-5-[4-(tetrahydrofuran-2-ylmethyl)piperazin-1-yl]imidazo[1,5-a]pyridin-6-yl}ethyl)-9H-purin-6-amine

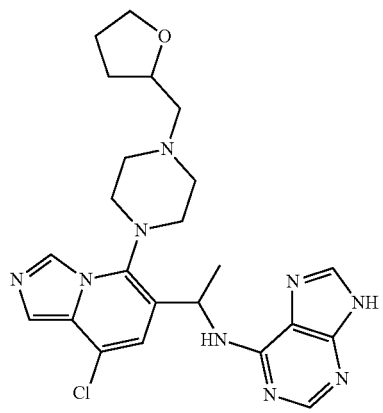 [SMILES: CC(Nc1ncnc2[nH]cnc12)c1cc(Cl)c2cncn2c1N1CCN(CC2CCCO2)CC1]

The desired compound was prepared according to the procedure of Example 12, steps A-C, using tetrahydrofufuryl bromide as the starting material. LCMS calculated for $C_{23}H_{29}ClN_9O$ (M+H)$^+$: m/z=482.2. found: 481.9.

Example 17

N-(1-{8-Chloro-5-[4-(cyclopropylmethyl)piperazin-1-yl]imidazo[1,5-a]pyridin-6-yl}ethyl)-9H-purin-6-amine

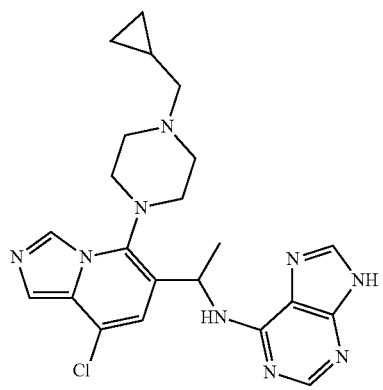 [SMILES: CC(Nc1ncnc2[nH]cnc12)c1cc(Cl)c2cncn2c1N1CCN(CC2CC2)CC1]

The desired compound was prepared according to the procedure of Example 15, steps A-C, using cyclopropanecarboxaldehyde as the starting material. LCMS calculated for $C_{22}H_{27}ClN_9$ (M+H)$^+$: m/z=452.2. found: 451.9.

Example 18

N-{1-[8-Chloro-5-(3-fluorophenyl)imidazo[1,5-a]pyridin-6-yl]propyl}-9H-purin-6-amine

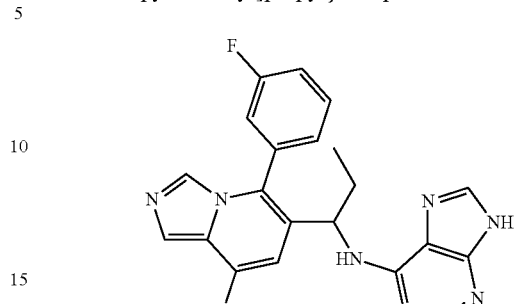

Step A: 1-[8-Chloro-5-(3-fluorophenyl)imidazo[1,5-a]pyridine-6-yl]propan-1-one

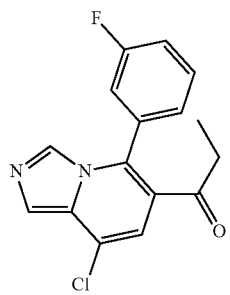

To a solution of 8-chloro-5-(3-fluorophenyl)-N-methoxy-N-methylimidazo[1,5-a]pyridine-6-carboxamide (300 mg, 0.91 mmol) in tetrahydrofuran (3.0 mL) cooled at 0° C., a 2 M solution of chloro(ethyl)magnesium in tetrahydrofuran (1.6 mL, 3.2 mmol) was added slowly and the mixture was stirred for 3 hours at 0° C. The reaction was quenched with acetic acid (0.5 mL), poured into saturated sodium bicarbonate (25 mL) and extracted with ethyl acetate. The extracts were washed with brine, dried over sodium sulfate, filtered and evaporated. Purification on silica gel using ethyl acetate in hexanes (0-60%) gave the desired compound (130 mg, 49%). LCMS calculated for $C_{16}H_{13}ClFN_2O$ (M+H)$^+$: m/z=303.1. found: 302.9.

Step B: 1-[8-Chloro-5-(3-fluorophenyl)imidazo[1,5-a]pyridine-6-yl]propan-1-amine

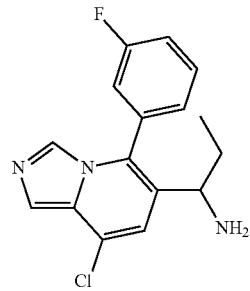 [SMILES: CCC(N)c1cc(Cl)c2cncn2c1-c1cccc(F)c1]

The desired compound was prepared according to the procedure of Example 1, step K, using 1-[8-chloro-5-(3-fluorophenyl)imidazo[1,5-a]pyridine-6-yl]propan-1-one as the starting material in 39% yield. LCMS calculated for $C_{16}H_{16}ClFN_3$ (M+H)+: m/z=304.1. found: 303.9.

Step C: N-{1-[8-Chloro-5-(3-fluorophenyl)imidazo[1,5-a]pyridin-6-yl]propyl}-9H-purin-6-amine The desired compound was prepared according to the procedure of Example 10, step B, using 1-[8-chloro-5-(3-fluorophenyl)imidazo[1,5-a]pyridine-6-yl]propan-1-amine as the starting material in 41% yield. LCMS calculated for $C_{21}H_{18}ClFN_7$ (M+H)+: m/z=422.1. found: 421.9. $^1$H NMR (300 MHz, CDCl$_3$): δ 8.40 (s, 1H), 8.33 (s, 1H), 7.99 (m, 2H), 7.60 (m, 2H), 7.52 (m, 4H), 6.95 (s, 1H), 3.32 (m, 1H), 1.92 (m, 2H), 0.92 (m, 3H).

Example 19

N-{1-[8-Chloro-5-(3,5-difluorophenyl)-3-methylimidazo[1,5-a]pyridin-6-yl]ethyl}-9H-purin-6-amine

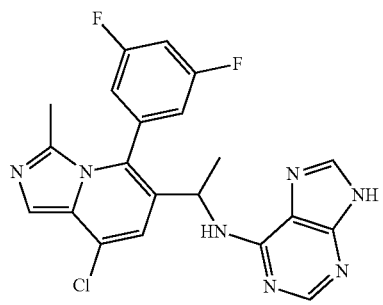 [SMILES: Cc1ncc2c(Cl)cc(C(C)Nc3ncnc4[nH]cnc34)c(-c3cc(F)cc(F)c3)n12]

Step A: Methyl 5-chloro-6-cyano-2-(3,5-difluorophenyl)nicotinate

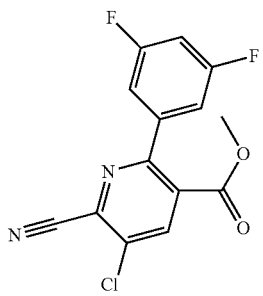 [SMILES: COC(=O)c1cc(Cl)c(C#N)nc1-c1cc(F)cc(F)c1]

A solution of methyl 2,5-dichloro-6-cyanonicotinate (2.0 g, 8.6 mmol), (3,5-difluorophenyl)boronic acid (1.5 g, 9.5 mmol) and potassium carbonate (2.6 g, 19 mmol) in water (16 mL) and 1,4-dioxane (41 mL) were bubbled with nitrogen gas (10 minutes). Bis(triphenylphosphine)palladium(II) chloride (0.67 g, 0.95 mmol) was added and the mixture was bubbled with nitrogen gas (10 minutes). The mixture was heated at 80° C. for 1 hour and diluted with ethyl acetate and water. The aqueous layer was separated and extracted again with ethyl acetate. The combined extracts were washed with water, washed with brine, dried over sodium sulfate, filtered and evaporated. Purification on silica gel using ethyl acetate in hexanes (0-50%) gave the desired compound (2.5 g, 94%). LCMS calculated for $C_{14}H_8ClF_2N_2O_2$ (M+H)+: m/z=309.0. found: 308.9.

Step C: Methyl 6-(aminomethyl)-5-chloro-2-(3,5-difluorophenyl)nicotinate

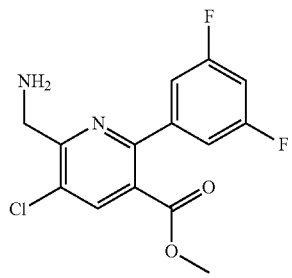 [SMILES: COC(=O)c1cc(Cl)c(CN)nc1-c1cc(F)cc(F)c1]

The desired compound was prepared by procedures analogous to those of Example 1, step E using methyl 5-chloro-6-cyano-2-(3,5-difluorophenyl)nicotinate as the starting material to give the desired compound (1.4 g, 25%) LCMS calculated for $C_{14}H_{12}ClF_2N_2O_2$ (M+H)+: m/z=313.1. found: 312.9.

Step D: Methyl 6-[(acetylamino)methyl]-5-chloro-2-(3,5-difluorophenyl)nicotinate

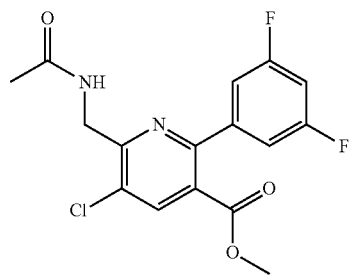 [SMILES: COC(=O)c1cc(Cl)c(CNC(C)=O)nc1-c1cc(F)cc(F)c1]

The desired compound was prepared by the procedure of Example 2, step A using methyl 6-(aminomethyl)-5-chloro-2-(3,5-difluorophenyl)nicotinate as the starting material (700 mg, 99%) LCMS calculated for $C_{16}H_{14}ClF_2N_2O_3$ (M+H)+: m/z=355.1. found: 354.9.

Step E: N-{1-[8-Chloro-5-(3,5-difluorophenyl)-3-methylimidazo[1,5-a]-pyridin-6-yl]ethyl}-9H-purin-6-amine The desired compound was prepared by procedures analogous to those of Example 1, step G-L using methyl 6-[(acetylamino)methyl]-5-chloro-2-(3-fluorophenyl)nicotinate as the starting material. LCMS calculated for $C_{21}H_{17}ClF_2N_7$ (M+H)+: m/z=440.1. found: 439.8. $^1$H NMR (300 MHz, CDCl$_3$): δ 8.37 (s, 1H), 7.98 (s, 1H), 7.57 (m, 1H), 7.48 (s, 1H), 7.25 (s, 1H), 7.00 (m, 2H), 6.88 (s, 1H), 6.37 (m, 1H), 2.00 (s, 3H), 1.90 (m, 1H), 1.50 (m, 3H).

Example 20

N-{1-[8-Chloro-5-(3,5-difluorophenyl)-3-methylimidazo[1,5-a]pyridin-6-yl]propyl}-9H-purin-6-amine

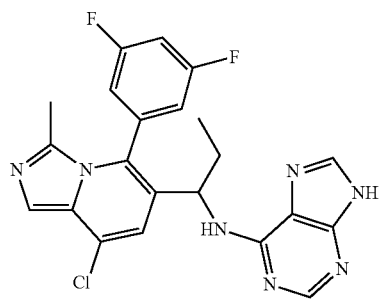 [SMILES: CCC(Nc1ncnc2[nH]cnc12)c1cc(Cl)c2cnc(C)n2c1-c1cc(F)cc(F)c1]

Step A: 1-[8-Chloro-5-(3,5-difluorophenyl)-3-methylimidazo[1,5-a]-pyridine-6-yl]propan-1-one

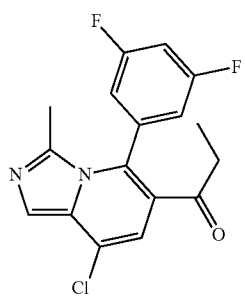 [SMILES: CCC(=O)c1cc(Cl)c2cnc(C)n2c1-c1cc(F)cc(F)c1]

The desired compound was prepared by the procedure of Example 1, step J using 8-chloro-5-(3,5-difluorophenyl)-N-methoxy-N,3-dimethylimidazo[1,5-a]pyridine-6-carboxamide and chloro(ethyl)magnesium as the starting materials in 39% yield. LCMS calculated for $C_{17}H_{14}ClF_2N_2O$ (M+H)$^+$: m/z=335.1. found: 334.9.

Step B: N-{1-[8-Chloro-5-(3,5-difluorophenyl)-3-methylimidazo[1,5-a]pyridin-6-yl]propyl}-9H-purin-6-amine The desired compound was prepared by procedures analogous to those of Example 1, steps K-L, using 1-[8-chloro-5-(3,5-difluorophenyl)-3-methylimidazo[1,5-a]pyridine-6-yl]propan-1-one as the starting material. LCMS calculated for $C_{22}H_{19}ClF_2N_7$ (M+H)$^+$: m/z=454.1. found: 453.8.

Example 21

N-(1-{8-Chloro-5-[(3R)-3-methoxypyrrolidin-1-yl]imidazo[1,5-a]pyridin-6-yl}ethyl)-9H-purin-6-amine

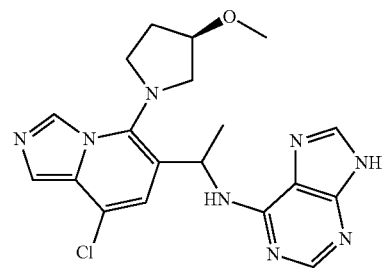 [SMILES: CO[C@@H]1CCN(c2c(C(C)Nc3ncnc4[nH]cnc34)cc(Cl)c3cncn23)C1]

The desired compound was prepared by procedures analogous to those of Example 4, steps C-O using (3R)-3-methoxypyrrolidine as the starting material. LCMS calculated for $C_{19}H_{22}ClN_8O$ (M+H)$^+$: m/z=413.1. found: 412.9. $^1$H NMR (300 MHz, CDCl$_3$): δ 8.46 (s, 1H), 8.37 (s, 1H), 7.93 (s, 1H), 7.58 (s, 1H), 6.85 (s, 1H), 6.48 (s, 1H), 5.88 (s, 1H), 4.20 (m, 1H), 3.79 (m, 1H), 3.58 (m, 2H), 3.40 (s, 3H), 3.23 (m, 1H), 2.24 (m, 2H), 2.22 (m, 1H), 1.60 (m, 3H).

Example 22

N-(1-{8-Chloro-5-[(3S)-3-methoxypyrrolidin-1-yl]imidazo[1,5-a]pyridin-6-yl}ethyl)-9H-purin-6-amine

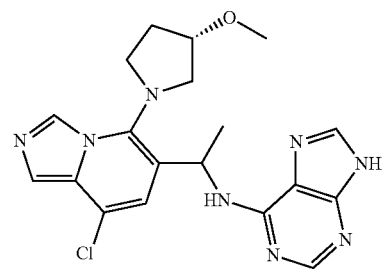 [SMILES: CO[C@H]1CCN(c2c(C(C)Nc3ncnc4[nH]cnc34)cc(Cl)c3cncn23)C1]

The desired compound was prepared by procedures analogous to those of Example 4, steps C-O using (3S)-3-methoxypyrrolidine as the starting material. LCMS calculated for $C_{19}H_{22}ClN_8O$ (M+H)$^+$: m/z=413.1. found: 412.9. $^1$H NMR (300 MHz, CDCl$_3$): δ 8.43 (s, 1H), 8.32 (s, 1H), 7.92 (s, 1H), 7.56 (s, 1H), 6.82 (s, 1H), 6.43 (s, 1H), 5.83 (s, 1H), 4.18 (m, 1H), 3.77 (m, 1H), 3.58 (m, 2H), 3.40 (s, 3H), 3.22 (m, 1H), 2.24 (m, 2H), 2.21 (m, 1H), 1.60 (m, 3H).

Example 23

(3R)-1-{8-Chloro-6-[1-(9H-purin-6-ylamino)ethyl]imidazo[1,5-a]pyridin-5-yl}pyrrolidin-3-ol

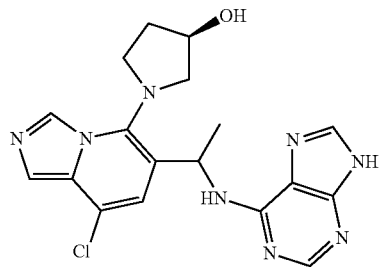 [SMILES: CC(Nc1ncnc2[nH]cnc12)c1cc(Cl)c2cncn2c1N1CC[C@@H](O)C1]

To a cooled solution of N-(1-{8-chloro-5-[(3R)-3-methoxypyrrolidin-1-yl]imidazo[1,5-a]pyridin-6-yl}ethyl)-9H-purin-6-amine (27.0 mg, 0.0654 mmol) in methylene chloride (1.0 mL) at −78° C. under an atmosphere of nitrogen was added slowly 1.0 M boron tribromide in methylene chloride (0.47 mL, 0.47 mmol). The mixture was allowed to warm up to room temperature and stirred for 30 minutes. The resultant mixture was quenched with $Na_2CO_3$ (aq). The cloudy suspension was filtered and washed with water. The filtrate was extracted with ethyl acetate and the organic layer was washed with brine and evaporated. Purification by preparative LCMS (pH 10) gave the desired compound (2.8 mg, 11%). LCMS calculated for $C_{18}H_{20}ClN_8O$ $(M+H)^+$: m/z=399.1. found: 398.9.

Example 24

(3S)-1-{8-Chloro-6-[1-(9H-purin-6-ylamino)ethyl]imidazo[1,5-a]pyridin-5-yl}pyrrolidin-3-ol

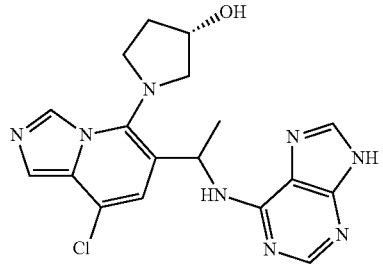 [SMILES: CC(Nc1ncnc2[nH]cnc12)c1cc(Cl)c2cncn2c1N1CC[C@H](O)C1]

To a cooled solution of N-(1-{8-chloro-5-[(3S)-3-methoxypyrrolidin-1-yl]imidazo[1,5-a]pyridin-6-yl}ethyl)-9H-purin-6-amine (18.0 mg, 0.0436 mmol) in methylene chloride (1.0 mL, 16 mmol) at −78° C. under an atmosphere of nitrogen was added slowly 1.0 M boron tribromide in methylene chloride (0.47 mL, 0.47 mmol). The mixture was allowed to warm up to room temperature and stirred for 30 minutes. The resultant mixture was quenched with $Na_2CO_3$ (aq). The cloudy suspension was filtered and washed with water. The filtrate was extracted with ethyl acetate and the organic layer was washed with brine and evaporated. Purification by preparative LCMS (pH 10) gave the desired compound (2.0 mg, 12%). LCMS calculated for $C_{18}H_{20}ClN_8O$ $(M+H)^+$: m/z=399.1. found: 399.0.

Example 25

N-{1-[8-Chloro-5-(diethylamino)-3-methylimidazo[1,5-a]pyridin-6-yl]ethyl}-9H-purin-6-amine

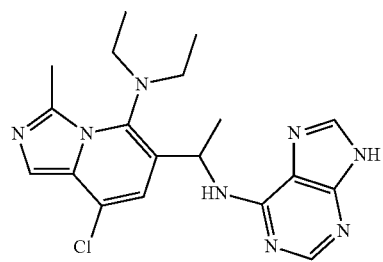 [SMILES: CCN(CC)c1c(C(C)Nc2ncnc3[nH]cnc23)cc(Cl)c2cnc(C)n12]

The desired compound was prepared by procedures analogous to those of Example 4, steps C-O, using N-ethylethanamine as the starting material. LCMS calculated for $C_{19}H_{24}ClN_8$ $(M+H)^+$: m/z=399.2. found: 399.0.

Example 26

N-{1-[4-chloro-7-(3-fluorophenyl)pyrazolo[1,5-a]pyridin-6-yl]ethyl}-9H-purin-6-amine

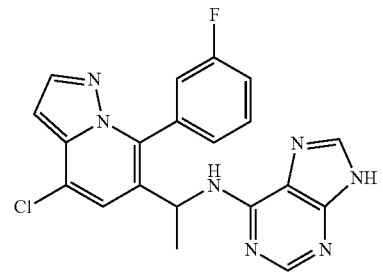 [SMILES: CC(Nc1ncnc2[nH]cnc12)c1cc(Cl)c2ccnn2c1-c1cccc(F)c1]

Step 1. Methyl 2,5-dichloronicotinate

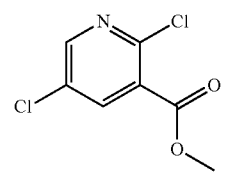

A solution of 2,5-dichloronicotinic acid (25.0 g, 130 mmol) in methylene chloride (650 mL) was treated with oxalyl chloride (22 mL, 260 mmol) followed by N,N-dimethylformamide (1.0 mL) and stirred at room temperature for 18 hours. The gas evolution ceased and the reaction mixture was concentrated. The acid chloride intermediate was taken up in methylene chloride (300 mL), cooled to 0° C. and treated with methanol (26 mL). The reaction was stirred at 0° C. for 30 minutes, allowed to warm to room temperature and was concentrated in vacuo to give an oil. This oil was taken up in ethyl acetate, washed with water saturated potassium carbonate, brine, dried over magnesium sulfate and concentrated to give methyl 2,5-dichloronicotinate (24.5 g, 92%) as an oil. LCMS calculated for $C_7H_6Cl_2NO_2(M+H)^+$: m/z=205.9, 207.9. found: 205.9, 207.9.

Step 2. Methyl 5-chloro-2-(3-fluorophenyl)nicotinate

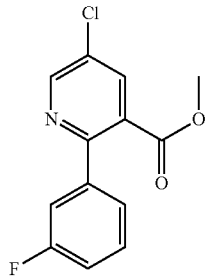

A solution of methyl 2,5-dichloronicotinate (27.0 g, 131 mmol), (3-fluorophenyl)boronic acid (20.2 g, 144 mmol), and potassium carbonate (39.5 g, 286 mmol) in water (190 mL) and 1,4-dioxane (578 mL) was degassed with nitrogen (10 min). The reaction mixture was treated with bis(triphenylphosphine)palladium(II) chloride (5.2 g, 7.4 mmol), degassed with nitrogen (10 min), and heated at 80° C. for 18 hours. The reaction was complete, allowed to cool to room temperature and partitioned between ethyl acetate and water. The combined organic layer was washed with water, brine, dried over magnesium sulfate, filtered, and concentrated to give the crude residue product as a dark oil. The product was purified on silica gel eluting with hexane:ethyl acetate gradient to give methyl 5-chloro-2-(3-fluorophenyl)nicotinate (27.5 g, 79%) as a white solid. LCMS calculated for $C_{13}H_{10}ClFNO_2(M+H)^+$: m/z=266.0. found: 265.9.

Step 3. Ethyl (1E)-N-[(mesitylsulfonyl)oxy]ethanimidoate

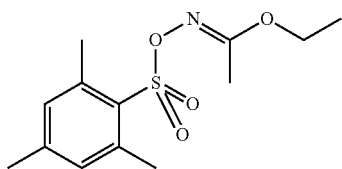 [SMILES: CCO/C(C)=N/OS(=O)(=O)c1c(C)cc(C)cc1C]

The ethyl (1E)-N-hydroxyethanimidoate (4.72 g, 45.7 mmol) was dissolved in N,N-dimethylformamide (12.0 mL) and triethylamine (6.37 mL, 45.7 mmol) and cooled in an ice bath. The mesitylenesulfonyl chloride (10.0 g, 45.7 mmol) was added portion wise over 5 minutes and the reaction was stirred vigorously for 30 minutes. The reaction mixture became a thick syrup. The reaction was diluted with methylene chloride (100 mL) and was washed with water 3×, brine, dried over magnesium sulfate and concentrated to give ethyl (1E)-N-[(mesitylsulfonyl)oxy]ethanimidoate (11.2 g, 86%) as a semi-solid residue. LCMS calculated for $C_{13}H_{20}NO_4S$ $(M+H)^+$: m/z=286.1. found: 285.9.

Step 4.
2-[(aminooxy)sulfonyl]-1,3,5-trimethylbenzene

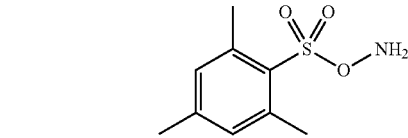

The ethyl (1Z)—N-[(mesitylsulfonyl)oxy]ethanimidoate (5.0 g, 18 mmol) was dissolved in 1,4-dioxane (4.5 mL, 58 mmol) and cooled in an ice bath under nitrogen. Perchloric acid (2.3 mL, 38 mmol) was added drop wise over 3 minutes. The reaction slowly became a thick mixture after 20 minutes. Ice (50 mL) was added to the reaction. The reaction was extracted with ethyl ether. The combined organic layer was washed with brine, dried over potassium carbonate (solid) and the volume was reduced to about 40 mL. LCMS calculated for $C_9H_{14}NO_3S$ $(M+H)^+$: m/z=216.0. found: 215.9.

Step 5. 3-tert-butyl 6-methyl 4-chloro-7-(3-fluorophenyl)pyrazolo[1,5-a]pyridine-3,6-dicarboxylate

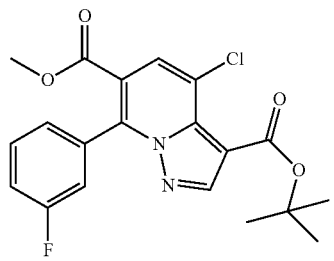 [SMILES: COC(=O)c1cc(Cl)c2c(C(=O)OC(C)(C)C)cnn2c1-c1cccc(F)c1]

The methyl 5-chloro-2-(3-fluorophenyl)nicotinate (1.00 g, 3.76 mmol) was combined with freshly prepared 2-[(aminooxy)sulfonyl]-1,3,5-trimethylbenzene (0.972 g, 4.52 mmol) ether solution in acetonitrile (20.0 mL) at room temperature. The reaction was stirred for 24 hours and became a tan colored slurry. The slurry was added portion wise to a vigorously stirring suspension of tert-butyl propiolate (1.55 mL, 11.3 mmol), N,N-dimethylformamide (20.0 mL, 258 mmol) and potassium carbonate (2.60 g, 18.8 mmol) open to the air. After stirring for 15 minutes, the reaction was a dark red brown suspension. This was allowed to stir for 5 hours at room temperature. The reaction was taken up in ethyl acetate and decanted from the solids. The organic layer was washed with water, brine, dried over magnesium sulfate and concentrated to give the crude product as a reddish brown oil. The product was purified on silica gel eluting hexane:ethyl acetate gradient to give 3-tert-butyl 6-methyl 4-chloro-7-(3-fluorophenyl)pyrazolo[1,5-a]pyridine-3,6-dicarboxylate (0.46 g, 30%) as a semi-solid residue. LCMS calculated for $C_{20}H_{19}ClFN_2O_4$ $(M+H)^+$: m/z=405.1. found: 404.9.

Step 6. Methyl 4-chloro-7-(3-fluorophenyl)pyrazolo[1,5-a]pyridine-6-carboxylate

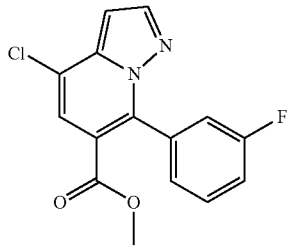 [SMILES: COC(=O)c1cc(Cl)c2ccnn2c1-c1cccc(F)c1]

The ester 3-tert-butyl 6-methyl 4-chloro-7-(3-fluorophenyl)pyrazolo[1,5-a]pyridine-3,6-dicarboxylate (0.450 g, 1.11 mmol) was dissolved in trifluoroacetic acid (15.0 mL) at room temperature. The reaction was heated to 60° C. and monitored by LCMS, after heating for 2 hours the reaction was complete. This was allowed to cool to room temperature and was concentrated in vacuo to give an amber oil. This was taken up in ethyl acetate, washed with water saturated sodium carbonate, brine, dried over magnesium sulfate and concentrated to give the crude product as an amber colored oil. The oil was purified on silica gel eluting hexane:ethyl acetate gradient to give methyl 4-chloro-7-(3-fluorophenyl)pyrazolo[1,5-a]pyridine-6-carboxylate (0.30 g, 89%) as a clear oil. LCMS calculated for $C_{15}H_{11}ClFN_2O_2$ (M+H)$^+$: m/z=305.0. found: 304.9.

Step 7. Chloro-7-(3-fluorophenyl)pyrazolo[1,5-a]pyridine-6-carboxylic acid

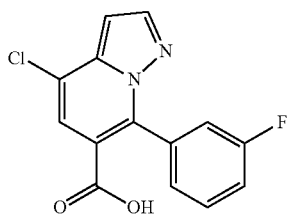 [SMILES: O=C(O)c1cc(Cl)c2ccnn2c1-c1cccc(F)c1]

The ester methyl 4-chloro-7-(3-fluorophenyl)pyrazolo[1,5-a]pyridine-6-carboxylate (0.30 g, 0.98 mmol) was dissolved in methanol (3.0 mL) and lithium hydroxide monohydrate (0.083 g, 2.0 mmol) in water (0.5 mL) was added. The reaction was stirred at room temperature overnight. The reaction was concentrated in vacuo and was neutralized with ammonium chloride. The aqueous layer was extracted with ethyl acetate ×3. The combined organic layer was washed with brine, dried over magnesium sulfate and concentrated in vacuo to give 4-chloro-7-(3-fluorophenyl)pyrazolo[1,5-a]pyridine-6-carboxylic acid (0.29 g, 100%) as a semi-solid. LCMS calculated for $C_{14}H_9ClFN_2O_2$ (M+H)$^+$: m/z=291.0. found: 290.8.

Step 8. 4-chloro-7-(3-fluorophenyl)-N-methoxy-N-methylpyrazolo[1,5-a]pyridine-6-carboxamide

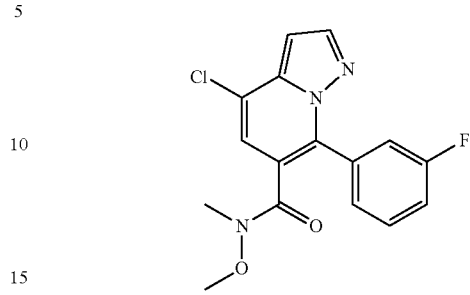

The N,N,N',N'-tetramethyl-O-(7-azabenzotriazol-1-yl)uronium hexafluorophosphate (0.46 g, 1.2 mmol) was added to a solution of 4-chloro-7-(3-fluorophenyl)pyrazolo[1,5-a]pyridine-6-carboxylic acid (0.29 g, 1.0 mmol) in N,N-dimethylformamide (3.0 mL) containing N,N-diisopropylethylamine (0.35 mL, 2.0 mmol) and N,O-dimethylhydroxylamine hydrochloride (0.14 g, 1.5 mmol) at room temperature. The reaction was complete after stirring for 2 hours. This was taken up in ethyl acetate, washed with water, brine, dried over magnesium sulfate and concentrated to give the crude amide. The product was purified on silica gel eluting hexane:ethyl acetate gradient to give 4-chloro-7-(3-fluorophenyl)-N-methoxy-N-methylpyrazolo[1,5-a]pyridine-6-carboxamide (0.29 g, 88%) as a glass. LCMS calculated for $C_{16}H_{14}ClFN_3O_2$ (M+H)$^+$: m/z=334.1. found: 333.9.

Step 9. 1-[4-chloro-7-(3-fluorophenyl)pyrazolo[1,5-a]-pyridin-6-yl]ethanone

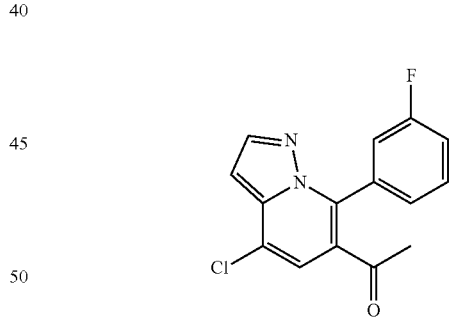

3.0 M Methylmagnesium bromide in tetrahydrofuran (0.87 mL) was added dropwise to a solution of 4-chloro-7-(3-fluorophenyl)-N-methoxy-N-methylpyrazolo[1,5-a]pyridine-6-carboxamide (0.25 g, 0.75 mmol) in tetrahydrofuran (3.038 mL) under $N_2$ cooled to 0° C. The solution was stirred at 0° C. for 30 minutes. The reaction solution was quenched at 0° C. with 1.0 M hydrogen chloride in water (2.996 mL), poured into 25 mL of water saturated sodium bicarbonate solution and was extracted into ethyl acetate. The organic layer was washed with brine, dried over magnesium sulfate and concentrated in vacuo to give 1-[4-chloro-7-(3-fluorophenyl)pyrazolo[1,5-a]pyridin-6-yl]ethanone (0.15 g, 68%) as an oil. LCMS calculated for $C_{15}H_{11}ClFN_2O$ (M+H)$^+$: m/z=289.1. found: 288.9.

Step 10. 1-[4-chloro-7-(3-fluorophenyl)pyrazolo[1,5-a]pyridin-6-yl]ethanamine

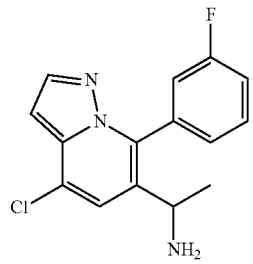 [SMILES: CC(N)c1cc(Cl)c2ccnn2c1-c1cccc(F)c1]

The mixture of 1-[4-chloro-7-(3-fluorophenyl)pyrazolo[1,5-a]pyridin-6-yl]ethanone (0.2 g, 0.7 mmol) in methanol (7.0 mL) and the ammonium acetate (0.5340 g, 6.928 mmol) was heated at 65° C. for 1 hour, all solids dissolved. The sodium cyanoborohydride (0.1306 g, 2.078 mmol) was added and the solution was heated at 65° C. overnight. The reaction was incomplete, additional ammonium acetate and sodium cyanoborohydride were added and the reaction was stirred for another 18 hours. This was allowed to cool to room temperature, concentrated in vacuo, taken up in ethyl acetate and washed with a small amount of water, brine, dried over magnesium sulfate and concentrated to give 1-[4-chloro-7-(3-fluorophenyl)pyrazolo[1,5-a]pyridin-6-yl]ethanamine (0.18 g, 90%) as a viscous oil. LCMS calculated for $C_{15}H_{14}ClFN_3$ $(M+H)^+$: m/z=290.1. found: 289.9.

Step 11. N-{1-[4-chloro-7-(3-fluorophenyl)pyrazolo[1,5-a]pyridin-6-yl]ethyl}-9H-purin-6-amine

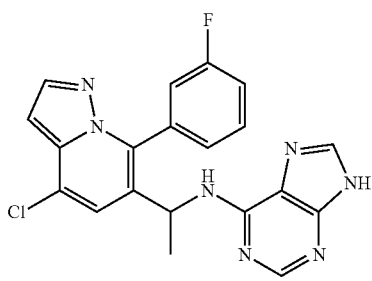 [SMILES: CC(Nc1ncnc2[nH]cnc12)c1cc(Cl)c2ccnn2c1-c1cccc(F)c1]

1-[4-Chloro-7-(3-fluorophenyl)pyrazolo[1,5-a]pyridin-6-yl]ethanamine (12 mg, 0.043 mmol) and 6-bromo-9-(tetrahydro-2H-pyran-2-yl)-9H-purine (0.018 g, 0.064 mmol) were stirred in ethanol (0.5 mL, 9 mmol) with N,N-diisopropylethylamine (37 μL, 0.21 mmol). The mixture was heated to 100° C. for 20 hours, the reaction was mostly complete. This was allowed to cool to room temperature and concentrated in vacuo to give a semi-solid residue. The residue was taken up in 4 M HCl in dioxane and stirred at room temperature for 1 hour. This was complete by LCMS and was concentrated to give a semi-solid residue. The product was purified by preparative HPLC on a C-18 column eluting acetonitrile: water gradient buffered with ammonia to pH 10 to give N-{1-[4-chloro-7-(3-fluorophenyl)pyrazolo[1,5-a]pyridin-6-yl]ethyl}-9H-purin-6-amine (8 mg, 47%) as a white amorphous solid. LCMS calculated for $C_{20}H_{16}ClFN_7$ $(M+H)^+$: m/z=408.1. found: 408.0. $^1$H NMR (400 MHz, DMSO-d$_6$/TFA): δ 8.52 (m, 1H), 8.42 (m, 1H), 7.98 (m, 1H), 7.69 (m, 1H), 7.63-7.51 (m, 2H), 7.45-7.31 (m, 2H), 6.77 (m, 1H), 5.1 (m, 1H), 1.55 (d, 3H).

Example 27

N-{1-[4-fluoro-7-(3-fluorophenyl)pyrazolo pyridin-6-yl]ethyl}-9H-purin-6-amine

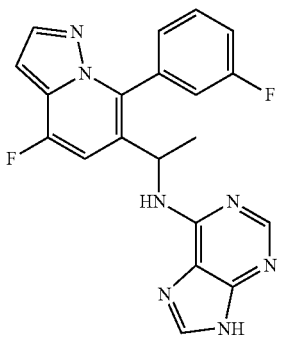 [SMILES: CC(Nc1ncnc2[nH]cnc12)c1cc(F)c2ccnn2c1-c1cccc(F)c1]

Using a procedure analogous to Example 1, but using 2-chloro-5-fluoronicotinic acid in Step 1, the title compound was prepared and was purified by preparative HPLC on a C-18 column eluting acetonitrile: water gradient buffered with ammonia to pH 10 to give N-{1-[4-fluoro-7-(3-fluorophenyl)pyrazolo[1,5-a]pyridin-6-yl]ethyl}-9H-purin-6-amine (10 mg, 50%) as a white amorphous solid. LCMS calculated for $C_{20}H_{16}F_2N_7$ $(M+H)^+$: m/z=392.1. found: 391.9. $^1$H NMR (400 MHz, CD$_3$OD): δ 8.14 (m, 1H), 8.06 (m, 1H), 7.86 (m, 1H), 7.63-7.56 (m, 2H), 7.31-7.23 (m, 3H), 6.74 (m, 1H), 5.25 (m, 1H), 1.55 (d, 3H).

Example 28

N-{1-[4-chloro-7-(3-methoxyphenyl)pyrazolo[1,5-a]pyridin-6-yl]ethyl}-9H-purin-6-amine

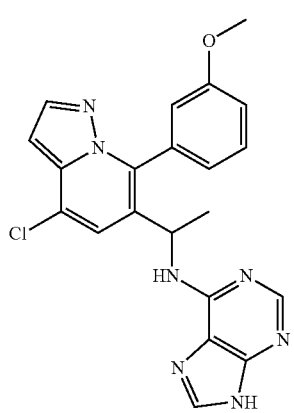 [SMILES: COc1cccc(-c2c(C(C)Nc3ncnc4[nH]cnc34)cc(Cl)c3ccnn23)c1]

Using a procedure analogous to Example 26, but using 3-methoxyphenylboronic acid in Step 2, the title compound was prepared and was purified by preparative HPLC on a C-18 column eluting acetonitrile: water gradient buffered with ammonia to pH 10 to give N-{1-[4-chloro-7-(3-methoxyphenyl)pyrazolo[1,5-a]pyridin-6-yl]ethyl}-9H-purin-6-

Example 29

N-{1-[8-Fluoro-5-(3-fluorophenyl)imidazo[1,5-a]pyridin-6-yl]ethyl}-9H-purin-6-amine

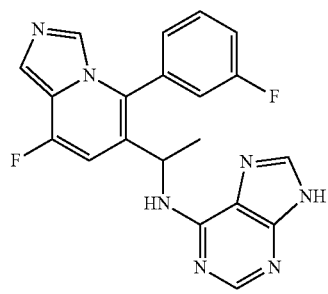 [SMILES: CC(Nc1ncnc2[nH]cnc12)c1cc(F)c2cncn2c1-c1cccc(F)c1]

amine (4 mg, 20%) as a white amorphous solid. LCMS calculated for $C_{21}H_{19}ClN_7O$ (M+H)$^+$: m/z=420.1. found: 419.9.

Step A: Methyl 2-chloro-5-fluoronicotinate hydrochloride

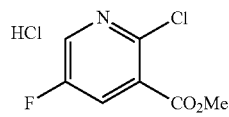

The desired compound was prepared according to the procedure of Example 1, step A, using 2-chloro-5-fluoronicotinic acid as the starting material (88% yield). LCMS for $C_7H_6ClFNO_2$ (M+H)$^+$: m/z=190.0. Found: 189.9.

Step B: Methyl 2-chloro-5-fluoronicotinate 1-oxide

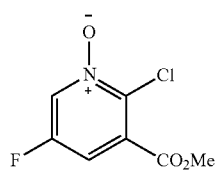 [SMILES: COC(=O)c1cc(F)c[n+]([O-])c1Cl]

The desired compound was prepared according to the procedure of Example 4, step A, using methyl 2-chloro-5-fluoronicotinate hydrochloride as the starting material (97% yield). LCMS for $C_7H_6ClFNO_3$ (M+H)$^+$: m/z=206.0. Found: 205.9.

Step C: Methyl 2-chloro-6-cyano-5-fluoronicotinate

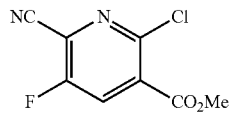 [SMILES: COC(=O)c1cc(F)c(C#N)nc1Cl]

The desired compound was prepared according to the procedure of Example 1, step D, using methyl 2-chloro-5-fluoronicotinate 1-oxide as the starting material (68% yield). LCMS for $C_8H_5ClFN_2O_2$ (M+H)$^+$: m/z=215.0. Found: 214.9.

Step D: Methyl 6-cyano-5-fluoro-2-(3-fluorophenyl)nicotinate

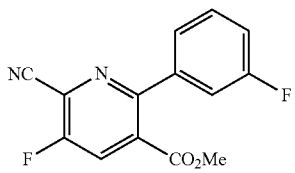 [SMILES: COC(=O)c1cc(F)c(C#N)nc1-c1cccc(F)c1]

The desired compound was prepared according to the procedure of Example 1, step B, using methyl 2-chloro-6-cyano-5-fluoronicotinate as the starting material (69% yield). LCMS for $C_{14}H_9F_2N_2O_2$ (M+H)$^+$: m/z=275.1. Found: 274.9.

Step E: Methyl 6-(aminomethyl)-5-fluoro-2-(3-fluorophenyl)nicotinate

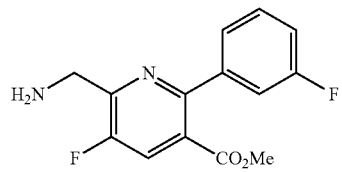 [SMILES: COC(=O)c1cc(F)c(CN)nc1-c1cccc(F)c1]

The desired compound was prepared according to the procedure of Example 1, step E, using methyl 6-cyano-5-fluoro-2-(3-fluorophenyl)nicotinate as the starting material (59% yield). LCMS for $C_{14}H_{13}F_2N_2O_2$ (M+H)$^+$: m/z=279.1. Found: 279.0.

Step F: Methyl 5-fluoro-2-(3-fluorophenyl)-6-[(formylamino)methyl]nicotinate

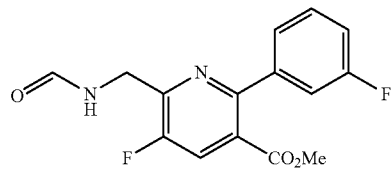 [SMILES: COC(=O)c1cc(F)c(CNC=O)nc1-c1cccc(F)c1]

The desired compound was prepared according to the procedure of Example 1, step F, using methyl 6-(aminomethyl)-5-fluoro-2-(3-fluorophenyl)nicotinate as the starting material. This material was used immediately in the next step without purification.

Step G: Methyl 8-fluoro-5-(3-fluorophenyl)imidazo[1,5-a]pyridine-6-carboxylate

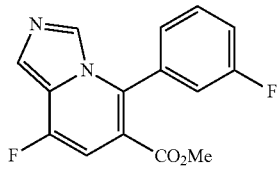

The desired compound was prepared according to the procedure of Example 1, step G, using methyl 5-fluoro-2-(3-fluorophenyl)-6-[(formylamino)methyl]nicotinate as the starting material (94% yield). LCMS for $C_{15}H_{11}F_2N_2O_2$ (M+H)$^+$: m/z=289.1. Found: 288.9.

Step H: 8-Fluoro-5-(3-fluorophenyl)imidazo[1,5-a]pyridine-6-carboxylic acid

The desired compound was prepared according to the procedure of Example 1, step H, using methyl 8-fluoro-5-(3-fluorophenyl)imidazo[1,5-a]pyridine-6-carboxylate as the starting material (95% yield). LCMS for $C_{14}H_9F_2N_2O_2$ (M+H)$^+$: m/z=275.1. Found: 274.9.

Step I: 8-Fluoro-5-(3-fluorophenyl)-N-methoxy-N-methylimidazo[1,5-a]pyridine-6-carboxamide

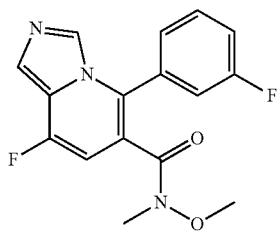 [SMILES: CON(C)C(=O)c1cc(F)c2cncn2c1-c1cccc(F)c1]

The desired compound was prepared according to the procedure of Example 1, step 1, using 8-fluoro-5-(3-fluorophenyl)imidazo[1,5-a]pyridine-6-carboxylic acid as the starting material (78% yield). LCMS for $C_{16}H_{14}F_2N_3O_2$ (M+H)$^+$: m/z=318.1. Found: 317.9.

Step J: 1-[8-Fluoro-5-(3-fluorophenyl)imidazol-[1,5-a]pyridin-6-yl]ethanone

The desired compound was prepared according to the procedure of Example 1, step J, using 8-fluoro-5-(3-fluorophenyl)-N-methoxy-N-methylimidazo[1,5-a]pyridine-6-carboxamide as the starting material (99% yield). LCMS for $C_{15}H_{11}F_2N_2O$ (M+H)$^+$: m/z=273.1. Found: 272.9.

Step K: 1-[8-Fluoro-5-(3-fluorophenyl)imidazo[1,5-a]-pyridin-6-yl]ethanamine

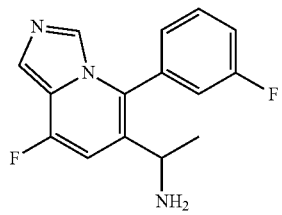 [SMILES: CC(N)c1cc(F)c2cncn2c1-c1cccc(F)c1]

The desired compound was prepared according to the procedure of Example 1, step K, using 1-[8-fluoro-5-(3-fluorophenyl)imidazo[1,5-a]pyridin-6-yl]ethanone as the starting material in 64% yield. LCMS for $C_{15}H_{14}F_2N_3$ (M+H)$^+$: m/z=274.1. Found: 274.0.

Step L: N-{1-[8-fluoro-5-(3-fluorophenyl)imidazo[1,5-a]pyridin-6-yl]ethyl}-9H-purin-6-amine The desired compound was prepared according to the procedure of Example 10, step B, using 1-[8-fluoro-5-(3-fluorophenyl)imidazo[1,5-a]pyridin-6-yl]ethanamine as the starting material (68% yield). The product was purified via preparative LCMS (XBridge C18 column, eluting with a gradient of acetonitrile/water containing 0.1% ammonium hydroxide, at flow rate of 60 mL/min). LCMS for $C_{20}H_{16}F_2N_7$ (M+H)$^+$: m/z=392.1. Found: 392.0. $^1$H NMR (300 MHz, DMSO-d$_6$): δ 12.89 (br s, 1H), 8.15-8.04 (m, 3H), 7.78-7.64 (m, 3H), 7.52-7.38 (m, 3H), 7.19-7.12 (m, 1H), 5.09-4.98 (m, 1H), 1.46-1.42 (m, 3H).

Example 30

N-{1-[5-(4-Acetylpiperazin-1-yl)-8-bromoimidazo[1,5-a]pyridin-6-yl]ethyl}-9H-purin-6-amine bis(trifluoroacetate)

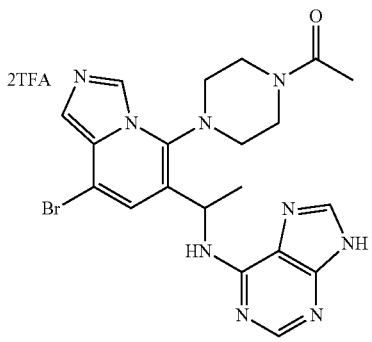 [SMILES: CC(=O)N1CCN(c2c(C(C)Nc3ncnc4[nH]cnc34)cc(Br)c3cncn23)CC1]

Step A: 2-Chloro-N-methoxy-N-methylnicotinamide

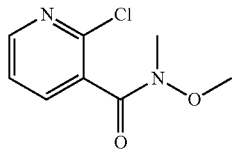

2-Chloronicotinoyl chloride (36 g, 0.20 mol) was dissolved in tetrahydrofuran (290 mL) and separately N,O-dimethylhydroxylamine hydrochloride (48 g, 0.49 mol) was stirred in 290 mL saturated bicarbonate solution until the degassing subsided. Then the bicarbonate solution was added to the acid chloride solution and the mixture was stirred at room temperature for 30 minutes. The reaction mixture was extracted with ethyl acetate (2×), dried over sodium sulfate, filtered and evaporated to give the desired product (34 g, 83%). LCMS for $C_8H_{10}ClN_2O_2$ (M+H)$^+$: m/z=201.0. Found: 200.9.

Step B: 2-Chloro-N-methoxy-N-methylnicotinamide 1-oxide

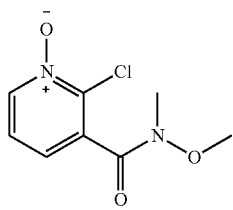

The desired compound was prepared according to the procedure of Example 4, step A, using methyl 2-chloro-N-methoxy-N-methylnicotinamide as the starting material (80% yield). LCMS for $C_8H_{10}ClN_2O_3$ (M+H)$^+$: m/z=217.0. Found: 216.9.

Step C: 2-Chloro-6-cyano-N-methoxy-N-methylnicotinamide

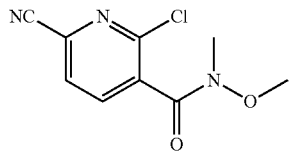

The desired compound was prepared according to the procedure of Example 1, step D, using 2-chloro-N-methoxy-N-methylnicotinamide 1-oxide as the starting material (86% yield). LCMS for $C_9H_9ClN_3O_2$ (M+H)$^+$: m/z=226.0. Found: 225.9.

Step D: tert-Butyl 4-(6-cyano-3-{[methoxy(methyl)amino]carbonyl}pyridin-2-yl)piperazine-1-carboxylate

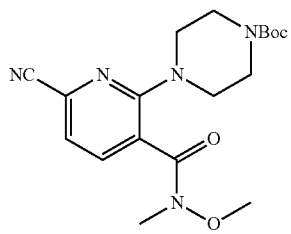 [SMILES: CON(C)C(=O)c1ccc(C#N)nc1N1CCN(C(=O)OC(C)(C)C)CC1]

The desired compound was prepared according to the procedure of Example 4, step C, using 2-chloro-6-cyano-N-methoxy-N-methylnicotinamide as the starting material (93% yield). LCMS for $C_{18}H_{25}N_5O_4Na$ (M+Na)$^+$: m/z=398.2. Found: 397.9.

Step E: tert-Butyl 4-(6-(aminomethyl)-3-{[methoxy(methyl)amino]carbonyl}pyridin-2-yl)piperazine-1-carboxylate

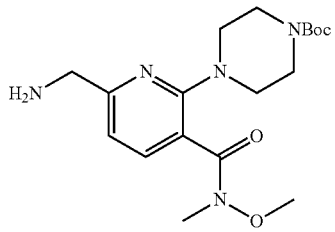 [SMILES: CON(C)C(=O)c1ccc(CN)nc1N1CCN(C(=O)OC(C)(C)C)CC1]

The desired compound was prepared according to the procedure of Example 1, step E, using tert-butyl 4-(6-cyano-3-{[methoxy(methyl)amino]carbonyl}pyridin-2-yl)piperazine-1-carboxylate as the starting material (72% yield). LCMS for $C_{18}H_{30}N_5O_4$ (M+H)$^+$: m/z=380.2. Found: 380.0.

Step F: tert-Butyl 4-(6-[(formylamino)methyl]-3-{[methoxy(methyl)amino]carbonyl}pyridin-2-yl)piperazine-1-carboxylate

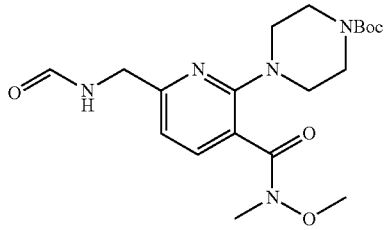 [SMILES: CON(C)C(=O)c1ccc(CNC=O)nc1N1CCN(C(=O)OC(C)(C)C)CC1]

The desired compound was prepared according to the procedure of Example 1, step F, using tert-butyl 4-(6-(aminomethyl)-3-{[methoxy(methyl)amino]carbonyl}pyridin-2-yl)piperazine-1-carboxylate as the starting material (94% yield). LCMS for $C_{19}H_{30}N_5O_5$ (M+H)$^+$: m/z=408.2. Found: 408.0.

Step G: tert-Butyl 4-(5-bromo-6-[(formylamino)methyl]-3-{[methoxy(methyl)amino]carbonyl}pyridin-2-yl)piperazine-1-carboxylate

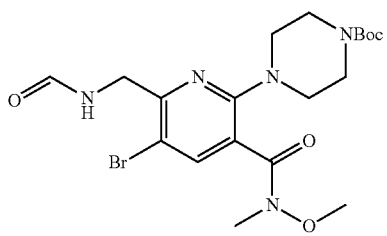

The desired compound was prepared according to the procedure of Example 4, step F, using tert-butyl 4-(6-[(formylamino)methyl]-3-{[methoxy(methyl)amino]carbonyl}pyridin-2-yl)piperazine-1-carboxylate as the starting material (96% yield). LCMS for $C_{19}H_{29}BrN_5O_5$ (M+H)$^+$: m/z=486.1, 488.1. Found: 486.0, 488.0.

Step H: 8-Bromo-N-methoxy-N-methyl-5-piperazin-1-ylimidazo[1,5-a]pyridine-6-carboxamide dihydrochloride

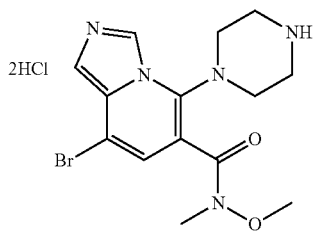 [SMILES: CON(C)C(=O)c1cc(Br)c2cncn2c1N1CCNCC1]

The desired compound was prepared according to the procedure of Example 1, step G, using tert-butyl 4-(5-bromo-6-[(formylamino)methyl]-3-{[methoxy(methyl)amino]carbonyl}pyridin-2-yl)piperazine-1-carboxylate as the starting material in quantitative yield. LCMS for $C_{14}H_{19}BrN_5O_2$ (M+H)$^+$: m/z=368.1, 370.1. Found: 367.9, 369.9.

Step I: 5-(4-Acetylpiperazin-1-yl)-8-bromo-N-methoxy-N-methylimidazo[1,5-a]pyridine-6-carboxamide

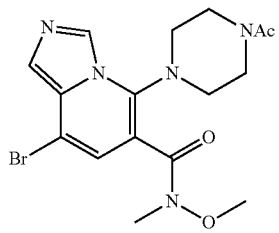

A solution of 8-bromo-N-methoxy-N-methyl-5-piperazin-1-ylimidazo[1,5-a]pyridine-6-carboxamide dihydrochloride (500 mg, 1.1 mmol) in N,N-dimethylformamide (5 mL) was treated with N,N-diisopropylethylamine (0.69 mL, 4.0 mmol), followed by 4-dimethylaminopyridine (5 mg, 0.04 mmol). The reaction mixture was treated with acetic anhydride (0.13 mL, 1.4 mmol) dropwise and stirred at 20° C. for 1 hour. The reaction mixture was diluted with ethyl acetate (200 mL), washed with saturated sodium bicarbonate, water (3×), and brine, dried over sodium sulfate, filtered and concentrated to give the desired product (0.41 g, 89%). This material was used without purification. LCMS for $C_{16}H_{21}BrN_5O_3$ (M+H)$^+$: m/z=410.1, 412.1. Found: 409.8, 411.8.

Step J: 1-[5-(4-Acetylpiperazin-1-yl)-8-bromoimidazo[1,5-a]pyridin-6-yl]ethanone

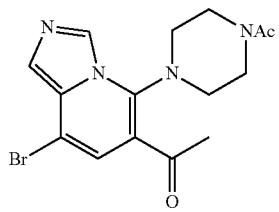

The desired compound was prepared according to the procedure of Example 1, step J, using 5-(4-acetylpiperazin-1-yl)-8-bromo-N-methoxy-N-methylimidazo[1,5-a]pyridine-6-carboxamide as the starting material (23% yield). LCMS for $C_{15}H_{18}BrN_4O_2$ (M+H)$^+$: m/z=365.1, 367.1. Found: 364.9, 366.9.

Step K: 1-[5-(4-Acetylpiperazin-1-yl)-8-bromoimidazo[1,5-a]pyridin-6-yl]ethanamine

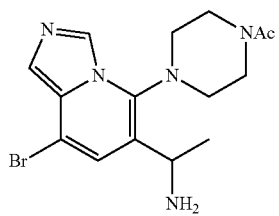

The desired compound was prepared according to the procedure of Example 1, step K, using 1-[5-(4-acetylpiperazin-1-yl)-8-bromoimidazo[1,5-a]pyridin-6-yl]ethanone as the starting material (24% yield). LCMS for $C_{15}H_{21}BrN_5O$ (M+H)+: m/z=366.1, 368.1. Found: 365.9, 367.9.

Step L: N-{1-[5-(4-Acetylpiperazin-1-yl)-8-bromoimidazo[1,5-a]pyridin-6-yl]ethyl}-9H-purin-6-amine bis(trifluoroacetate)

The desired compound was prepared according to the procedure of Example 1, step L, using 1-[5-(4-acetylpiperazin-1-yl)-8-bromoimidazo[1,5-a]pyridin-6-yl]ethanamine as the starting material in 34% yield. The product was purified via preparative LCMS (XBridge C18 column, eluting with a gradient of acetonitrile in water with 0.05% trifluoroacetic acid, at a flow rate of 30 mL/min). LCMS for $C_{20}H_{23}BrN_9O$ (M+H)+: m/z=484.1, 486.1. Found: 483.8, 485.8. $^1$H NMR (400 MHz, CD$_3$OD): δ 9.45 (s, 1H), 8.46 (s, 1H), 8.37 (s, 1H), 8.00 (s, 1H), 7.62-7.60 (m, 1H), 6.01-5.92 (m, 1H), 4.18-4.00 (m, 1H), 3.96-3.82 (m, 1H), 3.81-3.69 (m, 3H), 3.59-3.39 (m, 2H), 3.34 (s, 3H), 2.22-2.20 (m, 3H), 1.88-1.84 (m, 1H), 1.74-1.70 (m, 3H).

Example 31

5-(4-Acetylpiperazin-1-yl)-6-[1-(9H-purin-6-ylamino)ethyl]imidazo[1,5-a]pyridine-8-carbonitrile bis(trifluoroacetate)

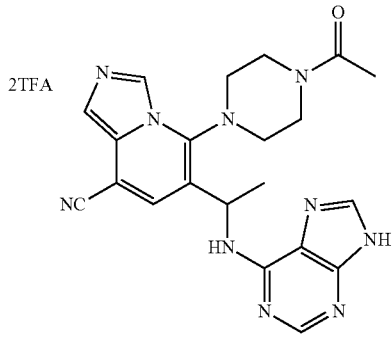 [SMILES: CC(=O)N1CCN(c2c(C(C)Nc3ncnc4[nH]cnc34)cc(C#N)c3cncn23)CC1]

Step A: tert-Butyl 4-(8-bromo-6-{[methoxy(methyl)amino]carbonyl}imidazo[1,5-a]-pyridin-5-yl)piperazine-1-carboxylate

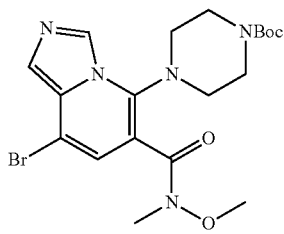

The desired compound was prepared according to the procedure of Example 4, step H, using 8-bromo-N-methoxy-N-methyl-5-piperazin-1-ylimidazo[1,5-a]pyridine-6-carboxamide dihydrochloride as the starting material (71% yield). LCMS for $C_{19}H_{27}BrN_5O_4$ (M+H)+: m/z=468.1, 470.1. Found: 467.9, 469.9.

Step B: tert-Butyl 4-(6-acetyl-8-bromoimidazo[1,5-a]-pyridin-5-yl)piperazine-1-carboxylate

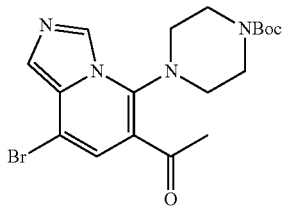 [SMILES: CC(=O)c1cc(Br)c2cncn2c1N1CCN(C(=O)OC(C)(C)C)CC1]

The desired compound was prepared according to the procedure of Example 1, step J, using tert-butyl 4-(8-bromo-6-{[methoxy(methyl)amino]carbonyl}imidazo[1,5-a]pyridin-5-yl)piperazine-1-carboxylate as the starting material (78% yield). LCMS for $C_{18}H_{24}BrN_4O_3$ (M+H)+: m/z=423.1, 425.1. Found: 422.8, 424.8.

Step C: tert-Butyl 4-[8-bromo-6-(1-hydroxyethyl)imidazol-[1,5-a]-pyridin-5-yl]piperazine-1-carboxylate

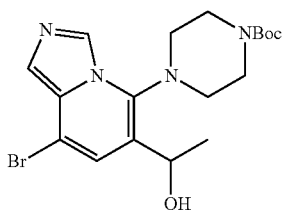 [SMILES: CC(O)c1cc(Br)c2cncn2c1N1CCN(C(=O)OC(C)(C)C)CC1]

A solution of tert-butyl 4-(6-acetyl-8-bromoimidazo[1,5-a]pyridin-5-yl)piperazine-1-carboxylate (0.55 g, 1.3 mmol) in methanol (8.1 mL) at 0° C. Sodium tetrahydroborate (98.3 mg, 2.60 mmol) was added in two portions to control bubbling. After complete addition, the solution was stirred for 30 minutes at 0° C. The reaction mixture was quenched by the addition of a small amount of acetic acid (0.2 mL) and concentrated. The residue was taken up in ethyl acetate (20 mL), washed with saturated sodium bicarbonate, water and brine, dried over sodium sulfate, filtered and concentrated to give the desired product (0.58 g, quantitative). This material was used without purification. LCMS for $C_{18}H_{26}BrN_4O_3$ (M+H)+: m/z=425.1, 427.1. Found: 424.9, 426.9.

Step D: tert-Butyl 4-[6-(1-azidoethyl)-8-bromoimidazo[1,5-a]pyridin-5-yl]piperazine-1-carboxylate

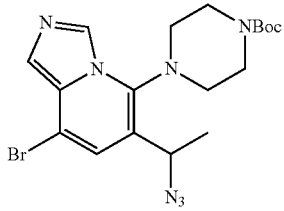

A solution of tert-butyl 4-[8-bromo-6-(1-hydroxyethyl)imidazo[1,5-a]pyridin-5-yl]piperazine-1-carboxylate (0.55 g, 1.3 mmol) in methylene chloride (5 mL, 78 mmol) at 0° C. was treated with N,N-diisopropylethylamine (0.90 mL, 5.2 mmol), followed by methanesulfonyl chloride (0.20 mL, 2.6 mmol) and stirred at 20° C. for 4 hours. The reaction mixture was diluted with water and extracted with ethyl acetate (2×).

The combined organic layers were washed with brine, dried over sodium sulfate, filtered and concentrated to give the crude mesylate which was used immediately without purification. A solution of the crude mesylate in N,N-dimethylformamide (5 mL) was treated with sodium azide (0.34 g, 5.2 mmol) and heated at 65° C. for 2 hours. The reaction mixture was diluted with ethyl acetate (25 mL), washed with water (2×15 mL) and brine, then dried over sodium sulfate, filtered and concentrated to give a residue. Purification by flash column chromatography using ethyl acetate in hexanes (0-50%) gave the desired product (250 mg, 32%). LCMS for $C_{18}H_{25}BrN_7O_2$ (M+H)$^+$: m/z=450.1, 452.1. Found: 449.9, 451.9.

Step E: 6-(1-Azidoethyl)-8-bromo-5-piperazin-1-ylimidazo[1,5-a]pyridine bis(trifluoroacetate)

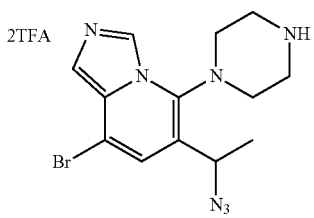 [SMILES: CC(N=[N+]=[N-])c1cc(Br)c2cncn2c1N1CCNCC1]

The desired compound was prepared according to the procedure of Example 4, step L, using tert-butyl 4-[6-(1-azidoethyl)-8-bromoimidazo[1,5-a]pyridin-5-yl]piperazine-1-carboxylate as the starting material (71% yield). LCMS for $C_{13}H_{17}BrN_7$ (M+H)$^+$: m/z=350.1, 352.1. Found: 349.9, 351.9.

Step F: 5-(4-Acetylpiperazin-1-yl)-6-(1-azidoethyl)-8-bromoimidazo[1,5-a]pyridine

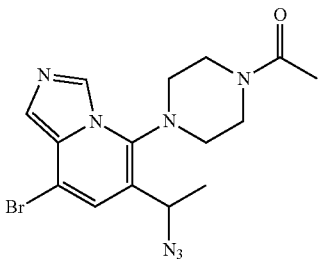

The desired compound was prepared according to the procedure of Example 30, step I, using 6-(1-azidoethyl)-8-bromo-5-piperazin-1-ylimidazo[1,5-a]pyridine bis(trifluoroacetate) as the starting material (89% yield). LCMS for $C_{15}H_{19}BrN_7O$ (M+H)$^+$: m/z=392.1, 394.1. Found: 391.9, 393.9.

Step G: 1-[5-(4-Acetylpiperazin-1-yl)-8-bromoimidazo[1,5-a]-pyridin-6-yl]ethanamine bis(trifluoroacetate)

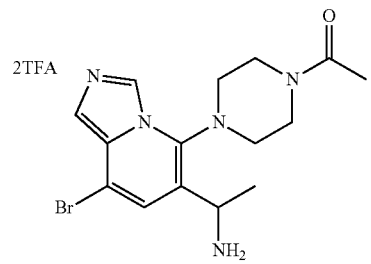 [SMILES: CC(=O)N1CCN(c2c(C(C)N)cc(Br)c3cncn23)CC1]

A solution of 5-(4-acetylpiperazin-1-yl)-6-(1-azidoethyl)-8-bromoimidazo[1,5-a]pyridine (55 mg, 0.14 mmol) in water (0.16 mL, 9.0 mmol) and tetrahydrofuran (0.81 mL) was treated with 1.0 M trimethylphosphine in tetrahydrofuran (0.17 mL, 0.17 mmol) and stirred at 20° C. for 1 hour. The reaction mixture was diluted with dichloromethane (10 mL) and washed with brine, dried with sodium sulfate, filtered, and concentrated to give a crude residue. Purification via preparative LCMS (XBridge C18 column, eluting with a gradient of acetonitrile in water with 0.05% trifluoroacetic acid, at a flow rate of 30 mL/min) gave the desired product (67 mg, 80%). LCMS for $C_{15}H_{21}BrN_5O$ (M+H)$^+$: m/z=366.1, 368.1. Found: 366.0, 367.9.

Step H: N-{1-[5-(4-Acetylpiperazin-1-yl)-8-bromoimidazo[1,5-a]pyridin-6-yl]ethyl}-9-(tetrahydro-2H-pyran-2-yl)-9H-purin-6-amine

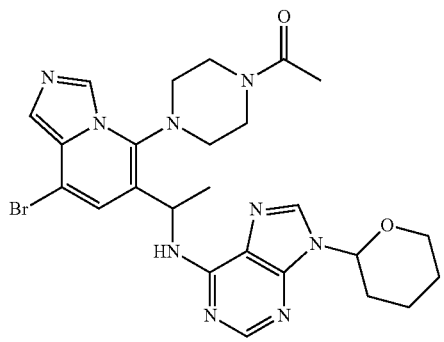 [SMILES: CC(=O)N1CCN(c2c(C(C)Nc3ncnc4c3ncn4C3CCCCO3)cc(Br)c3cncn23)CC1]

A solution of 1-[5-(4-acetylpiperazin-1-yl)-8-bromoimidazo[1,5-a]pyridin-6-yl]ethanamine bis(trifluoroacetate) (67 mg, 0.11 mmol), 6-bromo-9-(tetrahydro-2H-pyran-2-yl)-9H-purine (48 mg, 0.17 mmol), and N,N-diisopropylethylamine (98 mL, 0.56 mmol) in ethanol (0.87 mL) was heated at 95° C. overnight. Purification via preparative HPLC on a C-18 column eluting acetonitrile: water gradient buffered with ammonia to pH 10 gave the desired product (36 mg, 56%). LCMS for $C_{25}H_{31}BrN_9O_2$ (M+H)$^+$: m/z=568.2, 570.2. Found: 568.0, 570.0.

Step I: 5-(4-Acetylpiperazin-1-yl)-6-[1-(9H-purin-6-ylamino)ethyl]imidazo[1,5-a]pyridine-8-carbonitrile bis(trifluoroacetate)

A solution of N-{1-[5-(4-acetylpiperazin-1-yl)-8-bromo imidazo[1,5-a]pyridin-6-yl]ethyl}-9-(tetrahydro-2H-pyran- 2-yl)-9H-purin-6-amine (18 mg, 0.032 mmol) in N,N-dimethylformamide (0.59 mL) was treated with zinc cyanide (11 mg, 0.095 mmol) and tetrakis(triphenylphosphine)palladium (0) (7.3 mg, 0.006 mmol) and the solution was degassed. The reaction mixture was heated in the microwave at 130° C. for 3 minutes. The reaction mixture was diluted with methanol (2.5 mL) and 12.0 M hydrogen chloride in water (7.9 µL, 0.095 mmol) and stirred for 30 min. The reaction mixture was diluted with methanol, filtered, and purified via preparative LCMS (XBridge C18 column, eluting with a gradient of acetonitrile in water with 0.05% trifluoroacetic acid, at a flow rate of 30 mL/min) to give the desired product (6.0 mg, 44%). LCMS for $C_{21}H_{23}N_{10}O$ (M+H)$^+$: m/z=431.2. Found: 431.0. $^1$H NMR (300 MHz, DMSO-d$_6$): δ 8.78-8.70 (m, 2H), 8.36-8.32 (m, 2H), 7.92-7.90 (m, 1H), 7.69 (s, 1H), 5.88-5.76 (m, 1H), 3.98-3.20 (m, 9H), 2.10 (s, 3H), 1.61-1.58 (m, 3H).

Example 32

N-{1-[5-(4-Acetylpiperazin-1-yl)-8-methylimidazo[1,5-a]pyridin-6-yl]ethyl}-9H-purin-6-amine bis(trifluoroacetate)

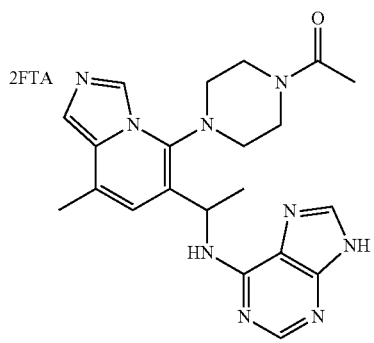 [SMILES: CC(=O)N1CCN(c2c(C(C)Nc3ncnc4[nH]cnc34)cc(C)c3cncn23)CC1]

Step A: 5-(4-Acetylpiperazin-1-yl)-6-(1-azidoethyl)-8-methylimidazo[1,5-a]pyridine trifluoroacetate

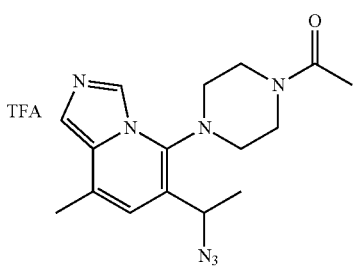 [SMILES: CC(=O)N1CCN(c2c(C(C)N=[N+]=[N-])cc(C)c3cncn23)CC1]

A solution of 5-(4-acetylpiperazin-1-yl)-6-(1-azidoethyl)-8-bromoimidazo[1,5-a]pyridine (50 mg, 0.13 mmol) in 1,4-dioxane (2.5 mL) was treated with 2.0 M dimethylzinc in toluene (0.13 mL, 0.26 mmol) and [1,1'-bis(diphenylphosphino)ferrocene]dichloropalladium(II), complex with dichloromethane (1:1) (21 mg, 0.026 mmol), degassed and heated in the microwave at 100° C. for 5 minutes. The reaction mixture was diluted slightly with methanol, filtered, and purified via preparative LCMS (XBridge C18 column, eluting with a gradient of acetonitrile in water with 0.05% trifluoroacetic acid, at a flow rate of 30 mL/min) to give the desired product (45 mg, 80%). LCMS for $C_{16}H_{22}N_7O$ (M+H)$^+$: m/z=328.2. Found: 328.0.

Step B: 1-[5-(4-acetylpiperazin-1-yl)-8-methylimidazol-[1,5-a]pyridin-6-yl]ethanamine

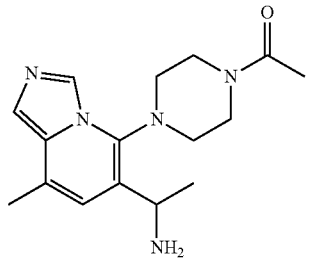 [SMILES: CC(=O)N1CCN(c2c(C(C)N)cc(C)c3cncn23)CC1]

The desired compound was prepared according to the procedure of Example 31, step G, using 5-(4-acetylpiperazin-1-yl)-6-(1-azidoethyl)-8-methylimidazo[1,5-a]pyridine trifluoroacetate as the starting material in 98% yield. LCMS for $C_{16}H_{24}N_5O$ (M+H)$^+$: m/z=302.2. Found: 302.0.

Step C: N-{1-[5-(4-Acetylpiperazin-1-yl)-8-methylimidazo[1,5-a]pyridin-6-yl]ethyl}-9H-purin-6-amine bis(trifluoroacetate The desired compound was prepared according to the procedure of Example 10, step B, using 1-[5-(4-acetylpiperazin-1-yl)-8-methylimidazo[1,5-a]pyridin-6-yl]ethanamine as the starting material in 23% yield. The product was purified via preparative LCMS (XBridge C18 column, eluting with a gradient of acetonitrile in water with 0.05% trifluoroacetic acid, at a flow rate of 60 mL/min) LCMS for $C_{21}H_{26}N_9O$ (M+H)$^+$: m/z=420.2. Found: 420.0. $^1$H NMR (300 MHz, DMSO-d$_6$): δ 9.55 (s, 1H), 8.74-8.66 (m, 1H), 8.30-8.26 (m, 2H), 8.16 (s, 1H), 7.27-7.23 (m, 1H), 5.96-5.80 (m, 1H), 3.95-3.06 (m, 8H), 2.38 (s, 3H), 2.10 (s, 3H), 1.58-1.55 (m, 3H).

Example A

PI3Kδ Scintillation Proximity Assay

Materials:
[γ-33P] ATP (10 mCi/mL) was purchased from Perkin-Elmer (Waltham, Mass.). Lipid kinase substrate, D-myo-Phosphatidylinositol-4,5-bisphosphate (PtdIns(4,5)P2)D(+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

Assay:
The kinase reaction was conducted in polystyrene 384-well matrix white plate from Thermo Fisher Scientific in a final volume of 25 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 µM PIP2, 20 µM ATP, 0.2 µCi [γ-$^{33}$P] ATP, 4 nM PI3Kδ. Reactions were incubated for 210 minutes and terminated by the addition of 40 µL SPA beads suspended in quench buffer: 150 mM potassium phosphate pH 8.0, 20% glycerol. 25 mM EDTA, 400 µM ATP. The final concentration of SPA beads is 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. Table 1 shows PI3Kδ scintillation proximity assay data for certain compounds described herein.

TABLE 1

IC$_{50}$ data for PI3Kδ scintillation proximity assay (assay A)

| Example | IC$_{50}$[a] |
|---|---|
| 1 | + |
| 1, isomer 1 | + |
| 1, isomer 2 | ++ |
| 2 | + |
| 3 | +++ |
| 4 | + |
| 5 | ++ |
| 6 | ++ |
| 7 | + |
| 8 | + |
| 9 | + |
| 10 | + |
| 11 | + |
| 12 | +++ |
| 13 | ++ |
| 14 | ++ |
| 15 | ++ |
| 16 | +++ |
| 17 | +++ |
| 18 | + |
| 19 | + |
| 20 | + |
| 21 | + |
| 22 | + |
| 23 | ++ |
| 24 | + |
| 25 | + |
| 26 | + |
| 27 | + |
| 28 | + |
| 29 | + |
| 30 | + |
| 31 | +++ |
| 32 | + |

[a] 50 nM or less (+); >50 nM to 200 nM (++); >200 nM to 750 nM (+++); and >750 nM (++++)

Example B

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells (2×10$^5$/well/200 µL) are cultured in 96-well ultra-low binding plates (Corning, Corning, N.Y.) in RPMI1640, 10% FBS and goat F(ab')2 anti-human IgM (10 µg/ml) (Invitrogen, Carlsbad, Calif.), in the presence of different amount of test compounds, for three days. [$^3$H]-thymidine (1 µCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience).

Example C

Pfeiffer Cell Proliferation Assay

Pfeiffer cell line (diffuse large B cell lymphoma) was purchased from ATCC (Manassas, Va.) and maintained in the culture medium recommended (RPMI and 10% FBS). To measure the anti-proliferation activity of the compounds, the Pfeiffer cells were plated with the culture medium (2×10$^3$ cells/well/per 200 µl) into 96-well ultra-low binding plates (Corning, Corning, N.Y.), in the presence or absence of a concentration range of test compounds. After 3-4 days, [$^3$H]-thymidine (1 µCi/well) (PerkinElmer, Boston, Mass.) in PBS was then added to the cell culture for an additional 12 hours before the incorporated radioactivity was separated by filtration with water through GF/B filters (Packard Bioscience, Meridenj, Conn.) and measured by liquid scintillation counting with a TopCount (Packard Bioscience). Table 2 shows Pfeiffer cell proliferation data for certain compounds described herein.

TABLE 2

IC$_{50}$ data for Pfeiffer cell proliferation assay*
Table 2. IC$_{50}$ data for Pfeiffer cell proliferation assay

| Example | Pfeiffer Cell Assay IC$_{50}$ (nM)[b] |
|---|---|
| 1 | + |
| 1, isomer 1 | + |
| 1, isomer 2 | Not tested |
| 3 | ++++ |
| 4 | +++ |
| 5 | +++++ |
| 6 | +++++ |
| 7 | ++ |
| 8 | +++++ |
| 9 | + |
| 10 | +++++ |
| 11 | +++++ |
| 12 | ++ |
| 13 | +++ |
| 14 | + |
| 15 | + |
| 16 | ++ |
| 17 | ++ |
| 18 | ++ |
| 19 | + |
| 20 | ++ |
| 21 | + |
| 22 | + |
| 23 | + |
| 24 | + |
| 25 | +++ |
| 26 | + |
| 27 | + |
| 28 | + |
| 29 | +++ |
| 30 | ++ |
| 31 | +++++ |
| 32 | +++++ |

[b] 100 nM or less (+); >100 nM to 500 nM (++); >500 nM to 1000 nM (+++); >1000 nM to 3000 nM (++++); and >3000 nM (+++++)

Example D

Akt Phosphorylation Assay

Ramos cells (B lymphocyte from Burkitts lymphoma) are obtained from ATCC (Manassas, Va.) and maintained in RPMI1640 and 10% FBS. The cells ($3 \times 10^7$ cells/tube/3 mL in RPMI) are incubated with different amounts of test compounds for 2 hours at 37° C. and then stimulated with goat F(ab')2 anti-human IgM (5 µg/mL) (Invitrogen) for 17 minutes, in a 37° C. water bath. The stimulated cells are spun down at 4° C. with centrifugation and whole cell extracts are prepared using 300 µL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacture's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula Ia:

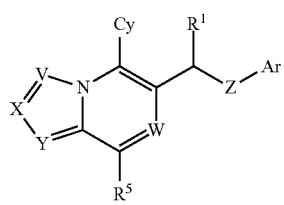

or a pharmaceutically acceptable salt thereof; wherein:
V is $CR^2$ or N;
X is $CR^3$ or N;
Y is $CR^4$ or N;
provided that at least two of V, X, and Y are other than N;
W is CH;
Z is O, S, or $NR^A$;
Cy is cycloalkyl, heterocycloalkyl, aryl or heteroaryl, each optionally substituted with 1, 2, 3, 4, or 5 independently selected $R^C$ groups;
each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, arylalkyl, heteroarylalkyl, cycloalkylalkyl, heterocycloalkylalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, heteroarylalkyl, cycloalkylalkyl, and heterocycloalkylalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)$ $R^{b2}$, $OC(O)NR^{c2}R^{d2}$, $C(=NR^g)NR^{c2}R^{d2}$, $NR^{c2}C(=NR^g)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^1$ is independently selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{1-6}$ haloalkyl, $C_{2-6}$ alkenyl, and $C_{2-6}$ alkynyl are each optionally substituted with 1, 2, 3 or 4 substituents independently selected from halo, OH, CN, $NR^{11}R^{12}$, $C_{1-6}$ alkoxy, $C_{1-6}$ haloalkoxy, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
each $R^{11}$ and $R^{12}$ is independently selected from H and $C_{1-6}$ alkyl;
or any $R^{11}$ and $R^{12}$ together with the N atom to which they are attached form a 3-, 4-, 5-, 6-, or 7-membered heterocycloalkyl group, which is optionally substituted with 1, 2, 3, or 4 substituents independently selected from $C_{1-6}$ alkyl;
$R^2$, $R^3$, $R^4$, or $R^5$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
Ar is heteroaryl, substituted with n independently selected $R^D$ groups;
each $R^D$ is independently selected from —($C_{1-4}$ alkyl)$_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)$ $R^{b1}$, $C(O)NR^{c1}R^{d1}$, $C(O)OR^{a1}$, $OC(O)R^{b1}$, $OC(O)$ $NR^{c1}R^{d1}$, $C(=NR^e)NR^{c1}R^{d1}$, $NR^{c1}C(=NR^e)$ $NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2$ $R^{b1}$, and $S(O)_2NR^{c1}R^{d1}$;
$R^A$ is selected from H, $C_{1-6}$ alkyl, $C_{2-6}$ alkenyl, and $C_{2-6}$ alkynyl;
each $Cy^1$ is, independently, aryl, heteroaryl, cycloalkyl, or heterocycloalkyl, each optionally substituted by 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, C$_{1-6}$ alkylaminocarbonylamino, and di(C$_{1-6}$ alkyl)aminocarbonylamino;

each R$^a$, R$^c$, and R$^d$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^b$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^c$ and R$^d$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^e$, R$^f$, and R$^g$ is independently selected from H, C$_{1-6}$ alkyl, CN, OR$^{a5}$, SR$^{b5}$, S(O)$_2$R$^{b5}$, C(O)R$^{b5}$, S(O)$_2$NR$^{c5}$R$^{d5}$, and C(O)NR$^{c5}$R$^{d5}$;

each R$^{a1}$, R$^{c1}$, and R$^{d1}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b1}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c1}$ and R$^{d1}$ together with the N atom to which they are attached form a 3-, 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, amino sulfonylamino, C$_{1-6}$ alkylaminosulfonylamino, di(C$_{1-6}$ alkyl)aminosulfonylamino, amino carbonylamino, C$_{1-6}$ alkylaminocarbonylamino, and di(C$_{1-6}$ alkyl)aminocarbonylamino;

each R$^{a2}$, R$^{c2}$, and R$^{d2}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{b2}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c2}$ and R$^{d2}$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{a5}$, R$^{c5}$, and R$^{d5}$ is independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, thio, C$_{1-6}$ alkylthio, C$_{1-6}$ alkylamino, di(C$_{1-6}$ alkyl)amino, C$_{1-6}$ haloalkyl, C$_{1-6}$ haloalkoxy, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b5}$ is independently selected from C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, thio, C$_{1-6}$ alkylthio, C$_{1-6}$ alkylamino, di(C$_{1-6}$ alkyl)amino, C$_{1-6}$ haloalkyl, C$_{1-6}$ haloalkoxy, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c5}$ and R$^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, C$_{1-6}$ alkyl, C$_{1-6}$ alkoxy, C$_{1-6}$ alkylthio, C$_{1-6}$ alkylamino, di(C$_{1-6}$ alkyl)amino, C$_{1-6}$ haloalkyl, and C$_{1-6}$ haloalkoxy;

n is 0, 1, 2, 3, 4, or 5; and r is 0 or 1.

2. The compound of claim 1, or a pharmaceutically acceptable salt thereof, wherein Z is NR$^A$.

3. The compound of claim 1, or a pharmaceutically acceptable salt thereof, wherein Cy is heterocycloalkyl, optionally substituted with 1, 2, 3, 4, or 5 independently selected R$^C$ groups.

4. The compound of claim 1, or a pharmaceutically acceptable salt thereof, wherein Cy is heteroaryl, optionally substituted with 1, 2, 3, 4, or 5 independently selected R$^C$ groups.

5. The compound of claim 1, or a pharmaceutically acceptable salt thereof, wherein Cy is a phenyl ring, which is optionally substituted with 1, 2, 3, 4, or 5 independently selected R$^C$ groups.

6. The compound of claim 1, or a pharmaceutically acceptable salt thereof, wherein each R$^C$ is independently halo.

7. The compound of claim 1, or a pharmaceutically acceptable salt thereof, wherein Ar is a moiety of formula:

wherein n is 0 or 1.

8. The compound of claim 1, or a pharmaceutically acceptable salt thereof, wherein n is 0.

9. The compound of claim 1, or a pharmaceutically acceptable salt thereof, wherein R$^1$ is methyl.

10. The compound of claim 1, or a pharmaceutically acceptable salt thereof, wherein R$^A$ is H.

11. The compound of claim 1, or a pharmaceutically acceptable salt thereof, wherein R$^2$, R$^3$, R$^4$, and R$^5$ are independently selected from H, OH, C$_{1-6}$ alkoxy, C$_{1-6}$ haloalkoxy, CN, halo, C$_{1-6}$ alkyl, and C$_{1-6}$ haloalkyl.

12. A compound of claim 1, or a pharmaceutically acceptable salt thereof, wherein:

Z is NH;

Cy is cycloalkyl, heterocycloalkyl, aryl or heteroaryl, each optionally substituted with 1, 2, 3, 4, or 5 independently selected R$^C$ groups;

each R$^C$ is independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-6}$ haloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O) R$^{b2}$, OC(O)NR$^{c2}$R$^{d2}$, C(=NR$^g$)NR$^{c2}$R$^{d2}$, NR$^{c2}$C(=NR$^g$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

Ar is a bicyclic azaheteroaryl group, substituted with n independently selected R$^D$ groups; wherein n is 0, 1, 2, 3, or 4;

each $R^D$ is independently selected from $NR^{c1}R^{d1}$;

$R^1$ is $C_{1-6}$ alkyl; and $R^2$, $R^3$, $R^4$, and $R^5$ are independently selected from H, OH, halo, CN, $C_{1-6}$ alkyl, $C_{1-6}$ alkoxy, $C_{1-6}$ haloalkoxy, amino, $C_{1-6}$ alkylamino, di($C_{1-6}$-alkyl)amino, carboxy, $C_{1-6}$ alkylcarbonyl, $C_{1-6}$ alkoxycarbonyl, carbamyl, $C_{1-6}$ alkylcarbamyl, di($C_{1-6}$-alkyl)carbamyl, $C_{1-6}$ alkylcarbonylamino, $C_{1-6}$ alkylthio, $C_{1-6}$ alkylsulfinyl, and $C_{1-6}$ alkylsulfonyl.

13. A compound of claim 1, or a pharmaceutically acceptable salt thereof, wherein:

Z is NH;

Cy is aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein said $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a moiety of formula:

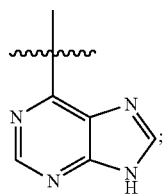 [SMILES: *c1ncnc2[nH]cnc12]

$R^1$ is $C_{1-6}$ alkyl; and $R^2$, $R^3$, $R^4$, and $R^5$ are each independently selected from H, OH, $C_{1-6}$ alkoxy, $C_{1-6}$ haloalkoxy, halo, CN, $C_{1-6}$ alkyl, and $C_{1-6}$ haloalkyl.

14. A compound of claim 1, or a pharmaceutically acceptable salt thereof, wherein:

Z is NH;

Cy is aryl, optionally substituted with 1, 2, 3, 4, or 5 independently selected $R^C$ groups;

each $R^C$ is independently selected from halo;

Ar is a moiety of formula:

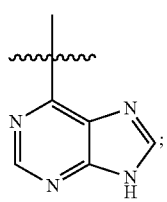 [SMILES: *c1ncnc2[nH]cnc12]

$R^1$ is $C_{1-6}$ alkyl; and $R^2$, $R^3$, $R^4$, and $R^5$ are each independently selected from H, halo, CN, $C_{1-6}$ alkyl, and $C_{1-6}$ haloalkyl.

15. A compound of claim 1, or a pharmaceutically acceptable salt thereof, wherein:

Z is NH;

Cy is phenyl, 5-membered or 6-membered heterocycloalkyl, each optionally substituted with 1, 2, 3, 4, or 5 independently selected $R^C$ groups;

each $R^C$ is independently selected from halo, $C_{1-6}$ alkyl, $C_{1-6}$ haloalkyl, cycloalkyl, heterocycloalkyl, cycloalkylalkyl, heterocycloalkylalkyl, CN, $OR^a$, $C(O)R^b$, and $S(O)_2R^b$; wherein said $C_{1-6}$ alkyl, $C_{1-6}$ haloalkyl, cycloalkyl, heterocycloalkyl, cycloalkylalkyl, heterocycloalkylalkyl are each optionally substituted with 1, 2, or 3 substituents independently selected from halo, $C_{1-6}$ alkyl, CN, and $OR^{a2}$;

each $R^a$ is selected from H, $C_{1-6}$ alkyl, aryl, cycloalkyl, heteroaryl, and heterocycloalkyl;

wherein said $C_{1-6}$ alkyl, aryl, cycloalkyl, heteroaryl, heterocycloalkyl are each optionally substituted with 1, 2, 3, 4, or 5 substituents independently selected from $C_{1-6}$ alkyl, $C_{1-6}$ haloalkyl, halo, CN, and $OR^{a5}$;

each $R^b$ is independently selected from $C_{1-6}$ alkyl, aryl, cycloalkyl, heteroaryl, and heterocycloalkyl; each of which is optionally substituted with 1, 2, 3, 4, or 5 substituents independently selected from $C_{1-6}$ alkyl, $C_{1-6}$ haloalkyl, halo, CN, and $OR^{a5}$;

each $R^{a2}$ and $R^{a5}$ is independently selected from H and $C_{1-4}$ alkyl;

Ar is a moiety of formula:

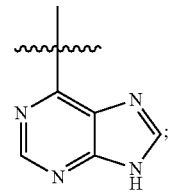 [SMILES: *c1ncnc2[nH]cnc12]

$R^1$ is $C_{1-6}$ alkyl; and $R^2$, $R^3$, $R^4$, and $R^5$ are each independently selected from H, halo, CN, $C_{1-6}$ alkyl, and $C_{1-6}$ haloalkyl.

16. A compound of Formula IIa:

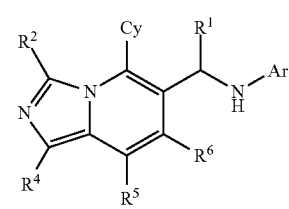

or a pharmaceutically acceptable salt thereof, wherein:

Cy is cycloalkyl, heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, arylalkyl, heteroarylalkyl, cycloalkylalkyl, heterocycloalkylalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and S(O)$_2$NR$^c$R$^d$; wherein said C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, heteroarylalkyl, cycloalkylalkyl, and heterocycloalkylalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^g$)NR$^{c2}$R$^{d2}$, NR$^{c2}$C(=NR$^g$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^1$ is independently selected from H, C$_{1-6}$ alkyl, C$_{1-6}$ haloalkyl, C$_{2-6}$ alkenyl, and C$_{2-6}$ alkynyl; wherein said C$_{1-6}$ alkyl, C$_{1-6}$ haloalkyl, C$_{2-6}$ alkenyl, and C$_{2-6}$ alkynyl are each optionally substituted with 1, 2, 3 or 4 substituents independently selected from halo, OH, CN, NR$^{11}$R$^{12}$, C$_{1-6}$ alkoxy, C$_{1-6}$ haloalkoxy, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{11}$ and R$^{12}$ is independently selected from H and C$_{1-6}$ alkyl;

or any R$^{11}$ and R$^{12}$ together with the N atom to which they are attached form a 3-, 4-, 5-, 6-, or 7-membered heterocycloalkyl group, which is optionally substituted with 1, 2, 3, or 4 substituents independently selected from C$_{1-6}$ alkyl;

R$^2$, R$^4$, or R$^5$ are each independently selected from H, OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

Ar is heteroaryl, substituted with n independently selected R$^D$ groups;

each R$^D$ is independently selected from —(C$_{1-4}$ alkyl)$_r$-Cy$^1$, halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^e$)NR$^{c1}$R$^{d1}$, NR$^{c1}$C(=NR$^e$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$ S(O)R$^{b1}$, NR$^{c1}$ S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

each R$^a$, R$^c$, and R$^d$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^b$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^c$ and R$^d$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^e$, R$^f$, and R$^g$ is independently selected from H, C$_{1-6}$ alkyl, CN, OR$^{a5}$, SR$^{b5}$, S(O)$_2$R$^{b5}$, C(O)R$^{b5}$, S(O)$_2$NR$^{c5}$R$^{d5}$, and C(O)NR$^{c5}$R$^{d5}$;

each R$^{a1}$, R$^{c1}$, and R$^{d1}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b1}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c1}$ and R$^{d1}$ together with the N atom to which they are attached form a 3-, 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, amino carbonylamino, C$_{1-6}$ alkylaminocarbonylamino, and di(C$_{1-6}$ alkyl)aminocarbonylamino;

each R$^{a2}$, R$^{c2}$, and R$^{d2}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{b2}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c2}$ and R$^{d2}$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{a5}$, R$^{c5}$, and R$^{d5}$ is independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, thio, C$_{1-6}$ alkylthio, C$_{1-6}$ alkylamino, di(C$_{1-6}$ alkyl)amino, C$_{1-6}$ haloalkyl, C$_{1-6}$ haloalkoxy, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b5}$ is independently selected from C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, thio, C$_{1-6}$ alkylthio, C$_{1-6}$ alkylamino, di(C$_{1-6}$ alkyl)amino, C$_{1-6}$ haloalkyl, C$_{1-6}$ haloalkoxy, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c5}$ and R$^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, C$_{1-6}$ alkyl, C$_{1-6}$ alkoxy, C$_{1-6}$ alkylthio, C$_{1-6}$ alkylamino, di(C$_{1-6}$ alkyl)amino, C$_{1-6}$ haloalkyl, and C$_{1-6}$ haloalkoxy;

n is 0, 1, 2, 3, 4, or 5; and r is 0 or 1.

17. The compound of claim 1, having Formula IIIa:

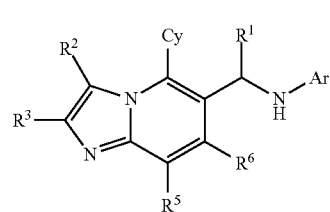

or a pharmaceutically acceptable salt thereof.

18. The compound of claim 1, having Formula IVa:

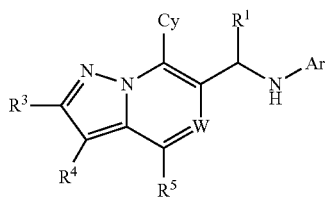

or a pharmaceutically acceptable salt thereof.

19. The compound according to claim 1, selected from:
N-{1-[8-Chloro-5-(3-fluorophenyl)imidazo[1,2-a]pyridin-6-yl]ethyl}-9H-purin-6-amine;
N-{1-[8-Chloro-5-(3-fluorophenyl)-3-methylimidazo[1,5-a]pyridin-6-yl]ethyl}-9H-purin-6-amine; and
N-{1-[8-chloro-5-(3-fluorophenyl)imidazo[1,5-a]pyridin-6-yl]ethyl}-9H-purin-6-amine;
or a pharmaceutically acceptable salt of any of the aforementioned.

20. The compound according to claim 1, selected from:
N-{1-[5-(4-Acetylpiperazin-1-yl)-8-chloroimidazo[1,5-a]pyridin-6-yl]ethyl}-9H-purin-6-amine;
N-(1-{8-chloro-5-[4-(methylsulfonyl)piperazin-1-yl]imidazo[1,5-a]pyridin-6-yl}ethyl)-9H-purin-6-amine;
tert-Butyl 4-{8-chloro-6-[1-(9H-purin-6-ylamino)ethyl]imidazo[1,5-a]pyridin-5-yl}piperazine-1-carboxylate;
N-(1-{8-Chloro-5-[4-(cyclopropylcarbonyl)piperazin-1-yl]imidazo[1,5-a]pyridin-6-yl}ethyl)-9H-purin-6-amine;
N-(1-{8-chloro-5-[4-(methoxyacetyl)piperazin-1-yl]imidazo[1,5-a]pyridin-6-yl}ethyl)-9H-purin-6-amine;
N-[1-(8-Chloro-5-piperazin-1-ylimidazo[1,5-a]pyridin-6-yl)ethyl]-9H-purin-6-amine dihydrochloride;
3-(4-{8-Chloro-6-[1-(9H-purin-6-ylamino)ethyl]imidazo[1,5-a]pyridin-5-yl}piperazin-1-yl)-3-oxopropanenitrile;
N-[1-(8-Chloro-5-{4-[(1-methyl-1H-pyrazol-4-yl)carbonyl]piperazin-1-yl}imidazo[1,5-a]pyridin-6-yl)ethyl]-9H-purin-6-amine;
N-(1-{8-Chloro-5-[4-(2-methoxyethyl)piperazin-1-yl]imidazo[1,5-a]pyridin-6-yl}ethyl)-9H-purin-6-amine;
(4-{8-Chloro-6-[1-(9H-purin-6-ylamino)ethyl]imidazo[1,5-a]pyridin-5-yl}piperazin-1-yl)acetonitrile;
N-(1-{8-Chloro-5-[4-(4,4,4-trifluorobutyl)piperazin-1-yl]imidazo[1,5-a]pyridin-6-yl}ethyl)-9H-purin-6-amine;
N-{1-[8-Chloro-5-(4-cyclobutylpiperazin-1-yl)imidazo[1,5-a]pyridin-6-yl]ethyl}-9H-purin-6-amine;
N-(1-{8-Chloro-5-[4-(tetrahydrofuran-2-ylmethyl)piperazin-1-yl]imidazo[1,5-a]pyridin-6-yl}ethyl)-9H-purin-6-amine;
N-(1-{8-Chloro-5-[4-(cyclopropylmethyl)piperazin-1-yl]imidazo[1,5-a]pyridin-6-yl}ethyl)-9H-purin-6-amine;
N-{1-[8-Chloro-5-(3-fluorophenyl)imidazo[1,5-a]pyridin-6-yl]propyl}-9H-purin-6-amine;
N-{1-[8-Chloro-5-(3,5-difluorophenyl)-3-methylimidazo[1,5-a]pyridin-6-yl]ethyl}-9H-purin-6-amine;
N-{1-[8-Chloro-5-(3,5-difluorophenyl)-3-methylimidazo[1,5-a]pyridin-6-yl]propyl}-9H-purin-6-amine;
N-(1-{8-Chloro-5-[(3R)-3-methoxypyrrolidin-1-yl]imidazo[1,5-a]pyridin-6-yl}ethyl)-9H-purin-6-amine;
N-(1-{8-Chloro-5-[(3S)-3-methoxypyrrolidin-1-yl]imidazo[1,5-a]pyridin-6-yl}ethyl)-9H-purin-6-amine;
(3R)-1-{8-Chloro-6-[1-(9H-purin-6-ylamino)ethyl]imidazo[1,5-a]pyridin-5-yl}pyrrolidin-3-ol;
(3S)-1-{8-Chloro-6-[1-(9H-purin-6-ylamino)ethyl]imidazo[1,5-a]pyridin-5-yl}pyrrolidin-3-ol;
N-{1-[8-Chloro-5-(diethylamino)-3-methylimidazo[1,5-a]pyridin-6-yl]ethyl}-9H-purin-6-amine;
N-{1-[4-chloro-7-(3-fluorophenyl)pyrazolo[1,5-a]pyridin-6-yl]ethyl}-9H-purin-6-amine;
N-{1-[4-fluoro-7-(3-fluorophenyl)pyrazolo[1,5-a]pyridin-6-yl]ethyl}-9H-purin-6-amine; and
N-{1-[4-chloro-7-(3-methoxyphenyl)pyrazolo[1,5-a]pyridin-6-yl]ethyl}-9H-purin-6-amine;
or a pharmaceutically acceptable salt of any of the aforementioned.

21. A compound according to claim 1, selected from:
N-{1-[8-Fluoro-5-(3-fluorophenyl)imidazo[1,5-a]pyridin-6-yl]ethyl}-9H-purin-6-amine;
N-{1-[5-(4-Acetylpiperazin-1-yl)-8-bromoimidazo[1,5-a]pyridin-6-yl]ethyl}-9H-purin-6-amine;
5-(4-Acetylpiperazin-1-yl)-6-[1-(9H-purin-6-ylamino)ethyl]imidazo[1,5-a]pyridine-8-carbonitrile; and
N-{1-[5-(4-Acetylpiperazin-1-yl)-8-methylimidazo[1,5-a]pyridin-6-yl]ethyl}-9H-purin-6-amine;
or a pharmaceutically acceptable salt of any of the aforementioned.

22. A composition comprising a compound of claim 1, or a pharmaceutically acceptable salt thereof, and at least one pharmaceutically acceptable carrier.

23. A method of inhibiting an activity of a PI3K kinase, comprising contacting the kinase with a compound of claim 1, or a pharmaceutically acceptable salt thereof.

24. The method of claim 23, wherein the PI3K is selected from the group consisting of PI3Kα, PI3Kβ, PI3Kγ, and PI3Kδ.

25. The method of claim 23, wherein said compound is a selective inhibitor for PI3Kδ over one or more of PI3Kγ, PI3Kβ, and PI3Kγ.

26. The compound of claim 16, or a pharmaceutically acceptable salt thereof, wherein:

Cy is phenyl, 5-membered or 6-membered heterocycloalkyl, each optionally substituted with 1, 2, 3, 4, or 5 independently selected $R^C$ groups;

each $R^C$ is independently selected from halo, $C_{1-6}$ alkyl, $C_{1-6}$ haloalkyl, cycloalkyl, heterocycloalkyl, cycloalkylalkyl, heterocycloalkylalkyl, CN, $OR^a$, $C(O)R^b$, and $S(O)_2R^b$; wherein said $C_{1-6}$ alkyl, $C_{1-6}$ haloalkyl, cycloalkyl, heterocycloalkyl, cycloalkylalkyl, heterocycloalkylalkyl are each optionally substituted with 1, 2, or 3 substituents independently selected from halo, $C_{1-6}$ alkyl, CN, and $OR^{a2}$;

each $R^a$ is selected from H, $C_{1-6}$ alkyl, aryl, cycloalkyl, heteroaryl, and heterocycloalkyl;

wherein said $C_{1-6}$ alkyl, aryl, cycloalkyl, heteroaryl, heterocycloalkyl are each optionally substituted with 1, 2, 3, 4, or 5 substituents independently selected from $C_{1-6}$ alkyl, $C_{1-6}$ haloalkyl, halo, CN, and $OR^{a5}$;

each $R^b$ is independently selected from $C_{1-6}$ alkyl, aryl, cycloalkyl, heteroaryl, and heterocycloalkyl; each of which is optionally substituted with 1, 2, 3, 4, or 5 substituents independently selected from $C_{1-6}$ alkyl, $C_{1-6}$ haloalkyl, halo, CN, and $OR^{a5}$;

each $R^{a2}$ and $R^{a5}$ is independently selected from H and $C_{1-4}$ alkyl;

Ar is a moiety of formula:

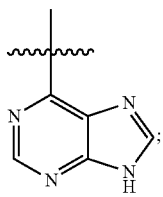 [SMILES: *c1ncnc2[nH]cnc12]

$R^1$ is $C_{1-6}$ alkyl; and
$R^2$, $R^4$, and $R^5$ are each independently selected from H, halo, CN, $C_{1-6}$ alkyl, and $C_{1-6}$ haloalkyl.

27. The compound of claim 17, or a pharmaceutically acceptable salt thereof, wherein:
Cy is phenyl, 5-membered or 6-membered heterocycloalkyl, each optionally substituted with 1, 2, 3, 4, or 5 independently selected $R^C$ groups;
each $R^C$ is independently selected from halo, $C_{1-6}$ alkyl, $C_{1-6}$ haloalkyl, cycloalkyl, heterocycloalkyl, cycloalkylalkyl, heterocycloalkylalkyl, CN, $OR^a$, $C(O)R^b$, and $S(O)_2R^b$; wherein said $C_{1-6}$ alkyl, $C_{1-6}$ haloalkyl, cycloalkyl, heterocycloalkyl, cycloalkylalkyl, heterocycloalkylalkyl are each optionally substituted with 1, 2, or 3 substituents independently selected from halo, $C_{1-6}$ alkyl, CN, and $OR^{a2}$;
each $R^a$ is selected from H, $C_{1-6}$ alkyl, aryl, cycloalkyl, heteroaryl, and heterocycloalkyl; wherein said $C_{1-6}$ alkyl, aryl, cycloalkyl, heteroaryl, heterocycloalkyl are each optionally substituted with 1, 2, 3, 4, or 5 substituents independently selected from $C_{1-6}$ alkyl, $C_{1-6}$ haloalkyl, halo, CN, and $OR^{a5}$;
each $R^b$ is independently selected from $C_{1-6}$ alkyl, aryl, cycloalkyl, heteroaryl, and heterocycloalkyl; each of which is optionally substituted with 1, 2, 3, 4, or 5 substituents independently selected from $C_{1-6}$ alkyl, $C_{1-6}$ haloalkyl, halo, CN, and $OR^{a5}$;
each $R^{a2}$ and $R^{a5}$ is independently selected from H and $C_{1-4}$ alkyl;
Ar is a moiety of formula:

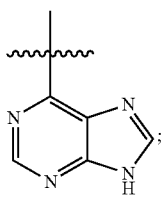 [SMILES: *c1ncnc2[nH]cnc12]

$R^1$ is $C_{1-6}$ alkyl; and
$R^2$, $R^3$, and $R^5$ are each independently selected from H, halo, CN, $C_{1-6}$ alkyl, and $C_{1-6}$ haloalkyl.

28. The compound of claim 18, or a pharmaceutically acceptable salt thereof, wherein:
Cy is phenyl, 5-membered or 6-membered heterocycloalkyl, each optionally substituted with 1, 2, 3, 4, or 5 independently selected $R^c$ groups;
each $R^C$ is independently selected from halo, $C_{1-6}$ alkyl, $C_{1-6}$ haloalkyl, cycloalkyl, heterocycloalkyl, cycloalkylalkyl, heterocycloalkylalkyl, CN, $OR^a$, $C(O)R^b$, and $S(O)_2R^b$; wherein said $C_{1-6}$ alkyl, $C_{1-6}$ haloalkyl, cycloalkyl, heterocycloalkyl, cycloalkylalkyl, heterocycloalkylalkyl are each optionally substituted with 1, 2, or 3 substituents independently selected from halo, $C_{1-6}$ alkyl, CN, and $OR^{a2}$;
each $R^a$ is selected from H, $C_{1-6}$ alkyl, aryl, cycloalkyl, heteroaryl, and heterocycloalkyl; wherein said $C_{1-6}$ alkyl, aryl, cycloalkyl, heteroaryl, heterocycloalkyl are each optionally substituted with 1, 2, 3, 4, or 5 substituents independently selected from $C_{1-6}$ alkyl, $C_{1-6}$ haloalkyl, halo, CN, and $OR^{a5}$;
each $R^b$ is independently selected from $C_{1-6}$ alkyl, aryl, cycloalkyl, heteroaryl, and heterocycloalkyl; each of which is optionally substituted with 1, 2, 3, 4, or 5 substituents independently selected from $C_{1-6}$ alkyl, $C_{1-6}$ haloalkyl, halo, CN, and $OR^{a5}$;
each $R^{a2}$ and $R^{a5}$ is independently selected from H and $C_{1-4}$ alkyl;
Ar is a moiety of formula:

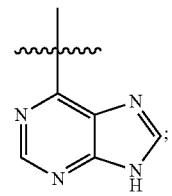 [SMILES: *c1ncnc2[nH]cnc12]

$R^1$ is $C_{1-6}$ alkyl; and
$R^3$, $R^4$, and $R^5$ are each independently selected from H, halo, CN, $C_{1-6}$ alkyl, and $C_{1-6}$ haloalkyl.

29. A method of treating arthritis in a patient, comprising administering to said patient a therapeutically effective amount of a compound of claim 1, or a pharmaceutically acceptable salt thereof, wherein said treating refers to inhibiting or ameliorating.

30. A method of treating myasthenia gravis in a patient, comprising administering to said patient a therapeutically effective amount of a compound of claim 1, or a pharmaceutically acceptable salt thereof, wherein said treating refers to inhibiting or ameliorating.

31. A method of treating Sjöegren's syndrome in a patient, comprising administering to said patient a therapeutically effective amount of a compound of claim 1, or a pharmaceutically acceptable salt thereof, wherein said treating refers to inhibiting or ameliorating.

32. A method of treating multiple sclerosis in a patient, comprising administering to said patient a therapeutically effective amount of a compound of claim 1, or a pharmaceutically acceptable salt thereof, wherein said treating refers to inhibiting or ameliorating.

33. A method of treating rheumatoid arthritis in a patient, comprising administering to said patient a therapeutically effective amount of a compound of claim 1, or a pharmaceutically acceptable salt thereof, wherein said treating refers to inhibiting or ameliorating.

34. A method of treating glomerulonephritis in a patient, comprising administering to said patient a therapeutically effective amount of a compound of claim 1, or a pharmaceutically acceptable salt thereof, wherein said treating refers to inhibiting or ameliorating.

35. A method of treating lupus in a patient, comprising administering to said patient a therapeutically effective amount of a compound of claim 1, or a pharmaceutically acceptable salt thereof, wherein said treating refers to inhibiting or ameliorating.

36. A method of treating diffuse large B cell lymphoma in a patient, comprising administering to said patient a therapeutically effective amount of a compound of claim 1, or a pharmaceutically acceptable salt thereof, wherein said treating refers to inhibiting or ameliorating.

37. A method of treating acute myeloblastic leukemia in a patient, comprising administering to said patient a therapeutically effective amount of a compound of claim 1, or a pharmaceutically acceptable salt thereof, wherein said treating refers to inhibiting or ameliorating.

38. A method of treating B cell lymphoma in a patient, comprising administering to said patient a therapeutically effective amount of a compound of claim 1, or a pharmaceutically acceptable salt thereof, wherein said treating refers to inhibiting or ameliorating.

39. A method of treating chronic myeloid leukemia in a patient, comprising administering to said patient a therapeutically effective amount of a compound of claim 1, or a pharmaceutically acceptable salt thereof, wherein said treating refers to inhibiting or ameliorating.

* * * * *

UNITED STATES PATENT AND TRADEMARK OFFICE
CERTIFICATE OF CORRECTION

PATENT NO. : 9,193,721 B2  
APPLICATION NO. : 13/085643  
DATED : November 24, 2015  
INVENTOR(S) : Combs et al.

Page 1 of 1

It is certified that error appears in the above-identified patent and that said Letters Patent is hereby corrected as shown below:

In the Claims

Col. 120, Line 43, Claim 31, delete "Sjöegren's" and insert -- Sjögren's --.

Signed and Sealed this
Seventh Day of June, 2016

Michelle K. Lee
*Director of the United States Patent and Trademark Office*